US006548538B2

(12) United States Patent
Urbahns et al.

(10) Patent No.: US 6,548,538 B2
(45) Date of Patent: Apr. 15, 2003

(54) PROPIONIC ACID DERIVATIVES

(75) Inventors: Klaus Urbahns, Kobe (JP); Michael Woltering, Wuppertal (DE); Susanne Nikolic, Wuppertal (DE); Josef Pernerstorfer, Wuppertal (DE); Berthold Hinzen, Velbert (DE); Elke Dittrich-Wengenroth, Wuppertal (DE); Hilmar Bischoff, Wuppertal (DE); Claudia Hirth-Dietrich, Wuppertal (DE); Klemens Lustig, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/973,753

(22) Filed: Oct. 9, 2001

(65) Prior Publication Data
US 2003/0032671 A1 Feb. 13, 2003

(30) Foreign Application Priority Data
May 22, 2001 (DE) .......................... 101 24 905

(51) Int. Cl.⁷ ..................... A61K 31/341; C07D 307/54
(52) U.S. Cl. ........................ 514/471; 549/494
(58) Field of Search ........................... 549/494; 514/471

(56) References Cited
U.S. PATENT DOCUMENTS 3,912,756 A  10/1975  Wolff et al. ................ 260/326
5,422,373 A  6/1995   Franzmann ................. 514/598
5,658,944 A  8/1997   Chapman, Jr. et al. ..... 514/478

FOREIGN PATENT DOCUMENTS

| DE | 2614045 | 6/1977 |
| WO | 9210468 | 6/1992 |
| WO | 9946232 | 9/1999 |
| WO | 0023407 | 4/2000 |

OTHER PUBLICATIONS

Brown, P., Winegar, D., Plunket, K., Moore, L., Lewis, M., Wilson, J., Sundseth, S., Koble, C., Wu, Z., Chapman, J., Lehmann, J., Kliewer, S., Willson, T., "A Ureido–Thioisobutyric Acid (GW9578) Is a Subtype–Selective PPARα Agonist with Potent Lipid–Lowering Activity", *J. Med. Chem.* 42:3785–3788 (1999).

Issemann, I., Green, S., "Activation of a member of the steroid hormone receptor superfamily by peroxisome proliferators", *Nature*, 347: 645–650 (Oct. 1990).

*Primary Examiner*—Joseph K. McKane
*Assistant Examiner*—Rebecca Anderson
(74) *Attorney, Agent, or Firm*—Susan M. Pellegrino

(57) ABSTRACT

The present application relates to novel potent PPAR-alpha-activating compounds for treating, for example, coronary heart disease, and to their preparation.

12 Claims, No Drawings

PROPIONIC ACID DERIVATIVES

The present invention relates to novel potent PPAR-alpha-activating compounds for treating, for example, coronary heart disease, and to their preparation.

In spite of many successful therapies, coronary heart disease (CHD) remains a serious public health problem. Treatment with statins, which inhibit HMG-CoA reductase, successfully lowers both LDL cholesterol plasma concentrations and the mortality of patients at risk; however, convincing treatment strategies for the therapy of patients having an unfavourable HDL/LDL cholesterol ratio or hypertriglyceridaemia are still not available to date.

Currently, fibrates are the only therapy option for patients of these risk groups. They act as weak agonists of the peroxisome-proliferator-activated receptor (PPAR)-alpha (*Nature* 1990, 347, 645–50). A disadvantage of the fibrates which have hitherto been approved is that their interaction with the receptor is only weak, requiring high daily doses and causing considerable side-effects.

WO 00/23407 describes PPAR modulators for treating obesity, atherosclerosis and/or diabetes.

It was an object of the present invention to provide novel compounds which can be used as PPAR-alpha modulators.

It has now been found that this object is achieved by compounds of the general formula (I)

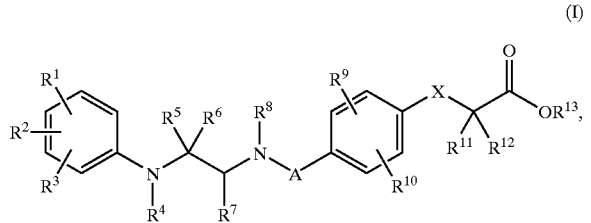

(I)

in which

A represents a bond or represents a —CH$_2$— or —CH$_2$CH$_2$— group,

X represents O, S or CH$_2$, $R^1$, $R^2$ and $R^3$ are identical or different and independently of one another each represents hydrogen, (C$_1$–C$_6$)-alkyl, (C$_3$–C$_7$)-cycloalkyl, hydroxyl, (C$_1$–C$_6$)-alkoxy, (C$_6$–C$_{10}$)-aryloxy, halogen, trifluoromethyl, trifluoromethoxy, (C$_1$–C$_6$)-alkylaminosulphonyl, nitro or cyano, or $R^1$ and $R^2$ are attached to two adjacent carbon atoms and together with these form a fused cyclohexane or benzene ring, the latter optionally being substituted by a (C$_1$–C$_4$)-alkylsulphonylmethyl group, and $R^3$ is as defined above, $R^4$ represents hydrogen or (C$_1$–C$_4$)-alkyl, $R^5$ and $R^6$ represent hydrogen or together with the carbon atom to which they are attached form a carbonyl group, $R^7$ represents hydrogen, (C$_1$–C$_6$)-alkyl, phenyl or benzyl, where the aromatic radicals mentioned for their part may in each case be mono- to trisubstituted by identical or different substituents from the group consisting of (C$_1$–C$_6$)-alkyl, (C$_1$–C$_6$)-alkoxy, hydroxyl and halogen, $R^8$ represents hydrogen, (C$_6$–C$_{10}$)-aryl or represents (C$_1$–C$_4$)-alkyl which for its part may be substituted by hydroxyl, trifluoromethoxy, (C$_1$–C$_4$)-alkoxy or phenoxy, which for their part are optionally mono- or disubstituted by trifluoromethyl, or by (C$_6$–C$_{10}$)-aryl or 5- or 6-membered heteroaryl having up to three heteroatoms from the group consisting of N, O and S, where all aryl and hetaroaryl rings mentioned may for their part in each case be mono- to trisubstituted by identical or different substituents from the group consisting of halogen, hydroxyl, (C$_1$–C$_6$)-alkyl, (C$_1$–C$_6$)-alkoxy, trifluoromethyl, trifluoromethoxy, cyano, nitro and amino, $R^9$ and $R^{10}$ are identical or different and independently of one another each represents hydrogen, (C$_1$–C$_6$)-alkyl, (C$_1$–C$_6$)-alkoxy, trifluoromethyl, trifluoromethoxy or halogen, $R^{11}$ and $R^{12}$ are identical or different and independently of one another each represents hydrogen or (C$_1$–C$_6$)-alkyl or together with the carbon atom to which they are attached form a (C$_4$–C$_7$)-cycloalkyl ring, and $R^{13}$ represents hydrogen or represents a group which can hydrolysed and degraded to the corresponding carboxylic acid, and their pharmaceutically acceptable salts, hydrates and solvates, which have pharmacological action and can be used as medicaments or for preparing medicament formulations.

In the context of the invention, a hydrolysable group in the definition of $R^{13}$ is a group which, in particular in the body, leads to a conversion of the —C(O)OR$^{13}$ grouping into the corresponding carboxylic acid ($R^{13}$=hydrogen). Such groups are, by way of example and by way of preference: benzyl, (C$_1$–C$_6$)-alkyl or (C$_3$–C$_8$)-cycloalkyl which are in each case optionally mono- or polysubstituted by identical or different substituents from the group consisting of halogen, hydroxyl, amino, (C$_1$–C$_6$)-alkoxy, carboxyl, (C$_1$–C$_6$)-alkoxycarbonyl, (C$_1$–C$_6$)-alkoxycarbonylamino and (C$_1$–C$_6$)-alkanoyloxy, and in particular (C$_1$–C$_4$)-alkyl which is optionally mono- or polysubstituted by identical or different substituents from the group consisting of halogen, hydroxyl, amino, (C$_1$–C$_4$)-alkoxy, carboxyl, (C$_1$–C$_4$)-alkoxycarbonyl, (C$_1$–C$_4$)-alkoxycarbonylamino and (C$_1$–C$_4$)-alkanoyloxy.

In the context of the invention, (C$_1$–C$_6$)-alkyl and (C$_1$–C$_4$)-alkyl represent a straight-chain or branched alkyl radical having 1 to 6 or 1 to 4 carbon atoms, respectively. Preference is given to a straight-chain or branched alkyl radical having 1 to 4 carbon atoms. The following radicals may be mentioned by way of example and by way of preference: methyl, ethyl, n-propyl, isopropyl and tert-butyl.

In the context of the invention, (C$_6$–C$_{10}$)-aryl represents an aromatic radical having 6 to 10 carbon atoms. A preferred example is the aryl radical phenyl.

In the context of the invention, (C$_3$–C$_8$)-cycloalkyl and (C$_4$–C$_7$)-cycloalkyl represent a cycloalkyl group having 3 to 8 and 4 to 7 carbon atoms, respectively. The following radicals may be mentioned by way of example and by way of preference: cyclobutyl, cyclopentyl and cyclohexyl.

In the context of the invention, (C$_1$–C$_6$)-alkoxy represents a straight-chain or branched alkoxy radical having 1 to 6 carbon atoms. Preference is given to a straight-chain or branched alkoxy radical having 1 to 4 carbon atoms. The following radicals may be mentioned by way of example and by way of preference: methoxy, ethoxy, n-propoxy, isopropoxy, tert-butoxy, n-pentoxy and n-hexoxy.

In the context of the invention, (C$_6$–C$_{10}$)-aryloxy represents an aromatic radical having 6 to 10 carbon atoms which is attached via an oxygen atom. A preferred example is the aryloxy radical phenoxy.

In the context of the invention, (C$_1$–C$_6$)-alkoxycarbonyl represents a straight-chain or branched alkoxy radical having 1 to 6 carbon atoms which is attached via a carbonyl group. Preference is given to a straight-chain or branched alkoxycarbonyl radical having 1 to 4 carbon atoms. The following radicals may be mentioned by way of example and by way of preference: methoxycarbonyl, ethoxycarbonyl, n-propoxycarbonyl, isopropoxycarbonyl and tert-butoxycarbonyl.

In the context of the invention, $(C_1-C_6)$-alkoxycarbonylamino represents an amino group having a straight-chain or branched alkoxycarbonyl substituent which has 1 to 6 carbon atoms in the alkoxy radical and is attached via the carbonyl group. Preference is given to an alkoxycarbonylamino radical having 1 to 4 carbon atoms. The following radicals may be mentioned by way of example and by way of preference: methoxycarbonylamino, ethoxycarbonylamino, n-propoxycarbonylamino, isopropoxycarbonylamino and tert-butoxycarbonylamino.

In the context of the invention, $(C_1-C_6)$-alkanoyloxy represents a straight-chain or branched alkyl radical having 1 to 6 carbon atoms which carries a doubly attached oxygen atom in the 1-position and is attached in the 1-position via a further oxygen atom. The following radicals may be mentioned by way of example and by way of preference: acetoxy, propionoxy, n-butyroxy, i-butyroxy, pivaloyloxy, n-hexanoyloxy.

In the context of the invention, $(C_1-C_6)$-alkylaminosulphonyl represents an amino group which is attached via a sulphonyl group and has a straight-chain or branched alkyl substituent having 1 to 6 carbon atoms. Preference is given to an alkylaminosulphonyl radical having 1 to 4 carbon atoms. The following radicals may be mentioned by way of example and by way of preference: methylaminosulphonyl, ethylaminosulphonyl, n-propylaminosulphonyl, isopropylaminosulphonyl and tert-butylaminosulphonyl.

In the context of the invention, halogen represents fluorine, chlorine, bromine and iodine. Preference is given to chlorine or fluorine.

In the context of the invention, 5- or 6-membered heteroaryl having up to 3 heteroatoms selected from the group consisting of S, N and O generally represents a monocyclic heteroaromatic radical which is attached via a ring carbon atom of the heteroaromatic radical, or, if appropriate, via a ring nitrogen atom of the heteroaromatic radical. The following radicals may be mentioned by way of example and by way of preference: furanyl, pyrrolyl, thienyl, thiazolyl, oxazolyl, imidazolyl, triazolyl, pyridyl, pyrimidyl, pyridazinyl. Preference is given to furanyl, thienyl and oxazolyl.

Depending on the substitution pattern, the compounds according to the invention can exist in stereoisomeric forms which are either like image and mirror image (enantiomers) or which are not like image and mirror image (diastereomers). The invention relates both to the enantiomers or diastereomers and to their respective mixtures. The racemic forms, like the diastereomers, can be separated in a known manner into the stereoisomerically uniform components.

Furthermore, certain compounds may be present in tautomeric forms. This is known to the person skilled in the art, and such compounds are likewise included within the scope of the invention.

The compounds according to the invention can also be present as salts. In the context of the invention, preference is given to physiologically acceptable salts.

Physiologically acceptable salts can be salts of the compounds according to the invention with inorganic or organic acids. Preference is given to salts with organic acids such as, for example, hydrochloric acid, hydrobromic acid, phosphoric acid or sulphuric acid or to salts with organic carboxylic or sulphonic acids such as, for example, acetic acid, propionic acid, maleic acid, fumaric acid, malic acid, citric acid, tartaric acid, lactic acid, benzoic acid, or methanesulphonic acid, ethanesulphonic acid, benzenesulphonic acid, toluenesulphonic acid or naphthalene-disulphonic acid.

Physiologically acceptable salts can also be salts of the compounds according to the invention with bases, such as, for example, metal or ammonium salts. Preferred examples are alkali metal salts (for example sodium salts or potassium salts), alkaline earth metal salts (for example magnesium salts or calcium salts), and also ammonium salts which are derived from ammonia or organic amines, such as, for example, ethylamine, di- or triethylamine, ethyldiisopropylamine, monoethanolamine, di- or triethanolamine, dicyclohexylamine, dimethylaminoethanol, dibenzylamine, N-methylmorpholine, dihydroabietylamine, 1-ephenamine, methylpiperidine, arginine, lysine, ethylenediamine or 2-phenylethylamine.

The compounds according to the invention can also be present in the form of their solvates, in particular in the form of their hydrates.

Preference is given to compounds of the general formula (I),
in which
  A represents a bond or represents a —CH$_2$— or —CH$_2$CH$_2$— group,
  X represents O, S or CH$_2$,
  $R^1$, $R^2$ and $R^3$ are identical or different and independently of one another each represents hydrogen, $(C_1-C_6)$-alkyl, $(C_1-C_6)$-alkoxy, hydroxyl, halogen, trifluoromethyl, trifluoromethoxy, nitro or cyano,
  $R^4$ represents hydrogen or $(C_1-C_4)$-alkyl,
  $R^5$ and $R^6$ each represents hydrogen or together with the carbon atom to which they are attached form a carbonyl group,
  $R^7$ represents hydrogen, $(C_1-C_6)$-alkyl, phenyl or benzyl, in which the aromatic radicals mentioned for their part may in each case be mono- to trisubstituted by identical or different substituents from the group consisting of $(C_1-C_6)$-alkyl, $(C_1-C_6)$-alkoxy, hydroxyl or halogen,
  $R^8$ represents hydrogen, $(C_6-C_{10})$-aryl or $(C_1-C_4)$-alkyl, which for its part is optionally substituted by $(C_6-C_{10})$-aryl or 5- or 6-membered heteroaryl having up to three heteroatoms from the group consisting of N, O and S, where all of the ring systems mentioned may for their part in each case be mono- to trisubstituted by identical or different substituents from the group consisting of halogen, hydroxyl, $(C_1-C_6)$-alkyl, $(C_1-C_6)$-alkoxy, trifluoromethyl, trifluoromethoxy, cyano, nitro and amino,
  $R^9$ and $R^{10}$ are identical or different and independently of one another each represents hydrogen, $(C_1-C_6)$-alkyl, $(C_1-C_6)$-alkoxy, trifluoromethyl, trifluoromethoxy or halogen,
  $R^{11}$ and $R^{12}$ are identical or different and independently of one another each represents hydrogen or $(C_1-C_6)$-alkyl, or together with the carbon atom to which they are attached they form a $(C_4-C_7)$-cycloalkyl ring, and
  $R^{13}$ represents hydrogen or a group that can be hydrolysed and degraded to the corresponding carboxylic acid,
and their pharmaceutically acceptable salts, hydrates and solvates.

Particular preference is given to compounds of the general formula (I), in which
A represents a —CH$_2$— or —CH$_2$CH$_2$— group,
X represents O, S or CH$_2$,
R$^1$, R$^2$ and R$^3$ are identical or different and independently of one another each represents hydrogen, (C$_1$–C$_4$)-alkyl, (C$_1$–C$_4$)-alkoxy, chlorine, fluorine, trifluoromethyl, trifluoromethoxy, nitro or cyano,
R$^4$ represents hydrogen or methyl,
R$^5$ and R$^6$ each represent hydrogen or together with the carbon atom to which they are attached form a carbonyl group,
R$^7$ represents hydrogen, (C$_1$–C$_4$)-alkyl or benzyl,
R$^8$ represents hydrogen, phenyl, benzyl or 5-membered heteroarylmethyl having up to two heteroatoms from the group consisting of N, O and S, where the aromatic ring systems mentioned for their part may in each case be mono- to trisubstituted by identical or different substituents from the group consisting of chlorine, fluorine, bromine, hydroxyl, (C$_1$–C$_4$)-alkyl, (C$_1$–C$_4$)-alkoxy, trifluoromethyl and amino,
R$^9$ and R$^{10}$ are identical or different and independently of one another each represents hydrogen, (C$_1$–C$_3$)-alkyl, (C$_1$–C$_3$)-alkoxy, trifluoromethyl, fluorine or chlorine,
R$^{11}$ and R$^{12}$ are identical or different and independently of one another each represents hydrogen, methyl or ethyl, or together with the carbon atom to which they are attached they form a cyclopentyl or cyclohexyl ring, and
R$^{13}$ represents hydrogen or represents a group that can be hydrolysed and degraded to the corresponding carboxylic acid,
and their pharmaceutically acceptable salts, hydrates and solvates.

Very particular preference is given to compounds of the general formula (I),
in which
A represents a —CH$_2$— or —CH$_2$CH$_2$— group,
X represents O, S or CH$_2$,
R$^1$ represents hydrogen, methyl or methoxy,
R$^2$ and R$^3$ are identical or different and independently of one another each represents methyl, trifluoromethyl, methoxy, trifluoromethoxy, chlorine or fluorine,
R$^4$ represents hydrogen,
R$^5$ and R$^6$ together with the carbon atom to which they are attached form a carbonyl group,
R$^7$ represents methyl, ethyl, n-propyl or, in particular, hydrogen,
R$^8$ represents phenyl, furanylmethyl or thienylmethyl, where the ring systems mentioned for their part may in each case be mono- or disubstituted by identical or different substituents from the group consisting of methyl and ethyl,
R$^9$ and R$^{10}$ are identical or different and each represents hydrogen or methyl in particular hydrogen,
R$^{11}$ and R$^{12}$ are identical or different and each represents hydrogen or methyl in particular methyl, and
R$^{13}$ represents a group which can be hydrolysed and degraded to the corresponding carboxylic acid, or, in particular, represents hydrogen,
and their pharmaceutically acceptable salts, hydrates and solvates.

The general or preferred radical definitions listed above apply both to the end products of the formula (I) and, correspondingly, to the starting materials and intermediates required in each case for the preparation.

The individual radical definitions given in the respective combinations or preferred combinations of radicals are, independently of the respective given combination of radicals, also replaced by any radical definitions of other combinations.

Of particular importance are compounds of the formula (I) in which R$^4$ is hydrogen.

Of particular importance are compounds of the formula (I) in which R$^5$ and R$^6$ together with the carbon atom to which they are attached form a carbonyl group.

Of particular importance are compounds of the formula (I) in which
R$^1$ represents hydrogen, methyl or methoxy, and
R$^2$ and R$^3$ are identical or different and independently of one another each represents methyl, isopropyl, tert-butyl, cyclohexyl, trifluoromethyl, methoxy, trifluoromethoxy, chlorine or fluorine.

Of particular importance are compounds of the formula (I) in which
R$^8$ represents phenyl, furanylmethyl, thienylmethyl or oxazolylmethyl, where the ring systems mentioned for their part may in each case be mono- or disubstituted by methyl, or represents 2-methoxyethyl.

Of very particular importance are compounds of the formula (IA)

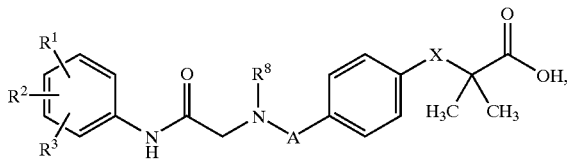

(IA)

in which
A represents a —CH$_2$— or —CH$_2$CH$_2$— group,
X represents O or S,
R$^1$ represents hydrogen, methyl or methoxy,
R$^2$ and R$^3$ are identical or different and independently of one another each represents methyl, isopropyl, tert-butyl, cyclohexyl, trifluoromethyl, methoxy, trifluoromethoxy, chlorine or fluorine, and
R$^8$ represents phenyl, furanylmethyl, thienylmethyl or oxazolylmethyl, where the ring systems mentioned for their part may in each case be mono- or disubstituted by methyl, or represents 2-methoxyethyl.

Moreover, we have found a process for preparing the compounds of the general formula (I) according to the invention, characterized in that
[A] compounds of the general formula (II)

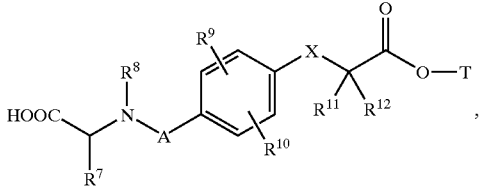

(II)

in which
A, X, R$^7$, R$^8$, R$^9$, R$^{10}$, R$^{11}$ and R$^{12}$ are each as defined above and T represents benzyl, $(C_1-C_6)$-alkyl or a polymeric support suitable for solid-phase synthesis, are initially, with activation of the carboxylic acid group in (II), reacted with compounds of the general formula (III)

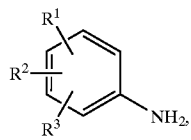
(III)

in which
R$^1$, R$^2$ and R$^3$ are each as defined above, to give compounds of the general formula (Ia)

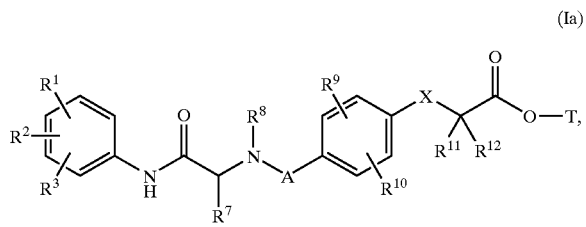
(Ia)

in which
A, X, T, R$^1$, R$^2$, R$^3$, R$^7$, R$^8$, R$^9$, R$^{10}$, R$^{11}$ and R$^{12}$ are each as defined above, or

[B] compounds of the general formula (IV)

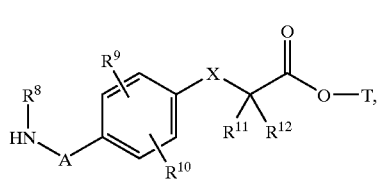
(IV)

in which
A, X, T, R$^8$, R$^9$, R$^{10}$, R$^{11}$ and R$^{12}$ are each as defined above, are, in the presence of a base, reacted with compounds of the general formula (V)

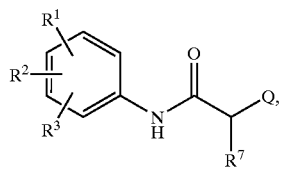
(V)

in which
R$^1$, R$^2$, R$^3$ and R$^7$ are each as defined above and
Q is a suitable leaving group, for example halogen, mesylate or tosylate, preferably bromine or iodine, likewise to compounds of the general formula (Ia)

the compounds of the general formula (Ia) are, if appropriate according to known methods for amide alkylation or amide reduction, converted into compounds of the general formula (Ib)

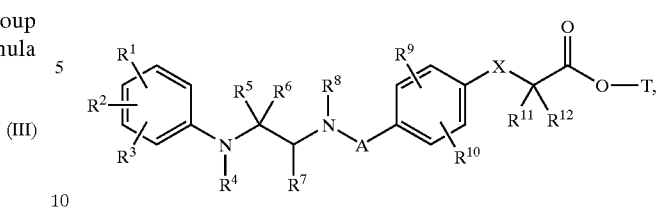
(Ib)

in which
A, X, T, R$^1$, R$^2$, R$^3$, R$^4$, R$^5$, R$^6$, R$^7$, R$^8$, R$^9$, R$^{10}$, R$^{11}$ and R$^{12}$ are each as defined above then converted with acids or bases into the corresponding carboxylic acids of the general formula (Ic)

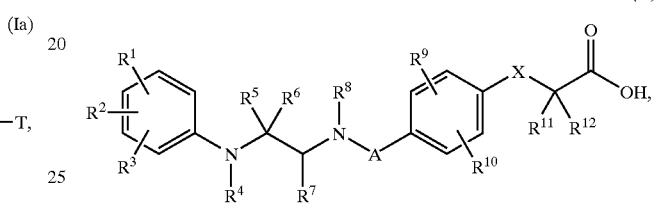
(Ic)

in which
A, X, R$^1$, R$^2$, R$^3$, R$^4$, R$^5$, R$^6$, R$^7$, R$^8$, R$^9$, R$^{10}$, R$^{11}$ and R$^{12}$ are each as defined above, and these are, if appropriate according to known methods for esterification, modified further by reaction with compounds of the general formula (VI)

$R^{13}-Z$ (VI), in which
R$^{13}$ is as defined above and
Z represents a suitable leaving group for example halogen, mesylate or tosylate or represents a hydroxyl group.

The process according to the invention is generally carried out at atmospheric pressure. However, it is also possible to carry out the process under elevated pressure or under reduced pressure (for example in a range of from 0.5 to 5 bar).

Solvents which are suitable for the process are customary organic solvents which do not change under the reaction conditions. These include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorobenzene, or ethyl acetate, pyridine, dimethyl sulphoxide, dimethylformamide, N,N'-dimethylpropyleneurea (DMPU), N-methylpyrrolidone (NMP), acetonitrile, acetone or nitromethane. It is also possible to use mixtures of the solvents mentioned.

Solvents which are preferred for process step (II)+(III)→(Ia) are dichloromethane and dimethylformamide. For process step (IV)+(V)→(Ia), preference is given to dimethylformamide.

The process step (II)+(III)→(Ia) according to the invention is generally carried out in a temperature range of from 0° C. to +100° C., preferably from 0° C. to +40° C. The process step (IV)+(V)→(Ia) is generally carried out in a temperature range of from 0° C. to +120° C., preferably from +50° C. to +100° C.

The auxiliaries used for the amide formation in process step (II)+(III)→(Ia) are preferably customary condensing agents, such as carbodiimides, for example, N,N'-diethyl-, N,N'-dipropyl-, N,N'-diisopropyl-, N,N'-dicyclohexylcarbodiimide (DCC), N-(3-dimethylaminoisopropyl)-N'-ethylcarbodiimide hydrochloride (EDC), or carbonyl compounds, such as carbonyldiimidazole, or 1,2-oxazolium compounds, such as 2-ethyl-5-phenyl-1,2-oxazolium 3-sulphate or 2-tert-butyl-5-methyl-isoxa-zolium perchlorate, or acylamino compounds, such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride or benzotriazolyloxy-tris(dimethylamino)phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), if appropriate in combination with further auxiliaries such as 1-hydroxybenzotriazole or N-hydroxysuccinimide, and the bases used are preferably alkali metal carbonates, for example sodium carbonate or bicarbonate or potassium carbonate or bicarbonate, or organic bases, such as trialkylamines, for example triethylamine, N-methyl-morpholine, N-methylpiperidine or diisopropylethylamine. Particular preference is given to the combination of EDC, N-methylmorpholine and 1-hydroxybenzotriazole, of EDC, triethylamine and 1-hydroxybenzotriazole and of HATU and diisopropylethyl amine.

Suitable bases for the reaction (IV)+(V)→(Ia) are the customary inorganic bases, such as alkali metal alkoxides, such as, for example, lithium hydroxide, sodium hydroxide or potassium hydroxide, alkali metal carbonates or alkaline earth metal carbonates, such as sodium carbonate, potassium carbonate, calcium carbonate or cesium carbonate, or sodium bicarbonate or potassium bicarbonate, or organic bases, such as trialkylamines, for example triethylamine, N-methylmorpholine, N-methyl-piperidine or diisopropyl-ethylamine. Preference is given to sodium bicarbonate.

The hydrolysis of the carboxylic acid esters in the process step (Ia) or (Ib)→(Ic) is carried out by customary methods by treating the esters in inert solvents with bases, the salts that are initially formed being converted by treatment with acid into the free carboxylic acids. In the case of the tert-butyl esters, the hydrolysis is preferably carried out using acids.

Suitable solvents for the hydrolysis of the carboxylic acid esters are water or the organic solvents which are customary for ester cleavage. These preferably include alcohols, such as methanol, ethanol, propanol, isopropanol or butanol, or ethers, such as tetrahydrofuran or dioxane, dimethylformamide, dichloromethane or dimethyl sulphoxide. It is also possible to use mixtures of the solvents mentioned. Preference is given to water/tetrahydrofuran and, in the case of the reaction with trifluoroacetic acid, to dichloromethane and, in the case of hydrogen chloride, to tetrahydrofuran, diethyl ether, dioxane or water.

Bases suitable for the hydrolysis are the customary inorganic bases. These preferably include alkali metal hydroxide or alkaline earth metal hydroxide, such as, for example, sodium hydroxide, lithium hydroxide, potassium hydroxide or barium hydroxide, or alkali metal carbonates, such as sodium carbonate or potassium carbonate, or sodium bicarbonate. Particular preference is given to using sodium hydroxide or lithium hydroxide.

Suitable acids are, in general, trifluoroacetic acid, sulphuric acid, hydrogen chloride, hydrogen bromide and acetic acid, or mixtures thereof, if appropriate with addition of water. Preference is given to hydrogen chloride or trifluoroacetic acid in the case of the tert-butyl esters and to hydrochloric acid in the case of the methyl esters.

In the case of compounds of the general formula (Ia) or (Ib) prepared by solid-phase synthesis and attached to a polymeric support via the carboxylic acid group, the cleavage from the resin to give the compounds of the general formula (Ic) is likewise carried out by the above-described customary methods for carboxylic acid ester hydrolysis. Here, preference is given to using trifluoroacetic acid.

When carrying out the hydrolysis, the base or the acid is generally employed in an amount of from 1 to 100 mol, preferably from 1.5 to 40 mol, based on 1 mole of the ester.

The hydrolysis is generally carried out in a temperature range of from 0° C. to +100° C., preferably from 0° C. to +50° C.

The compounds of the general formula (II) are novel, and they can be prepared by initially

[a] reacting compounds of the general formula (VII)

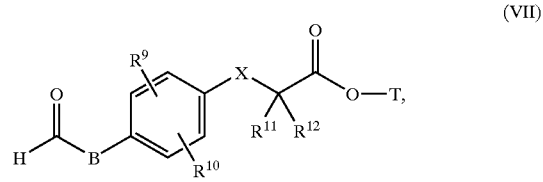

(VII)

in which

X, T, $R^9$, $R^{10}$, $R^{11}$ and $R^{12}$ are each as defined above and

B represents a bond or a methylene group in the presence of a suitable reducing agent with compounds of the general formula (VIII)

$R^{14}$—$NH_2$ (VIII), in which $R^{14}$ [a-1] has the meaning of $R^8$ given above or

[a-2] represents a group of the formula

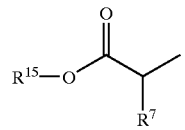

in which $R^7$ is as defined above and $R^{15}$ represents ($C_1$–$C_4$)-alkyl or trimethylsilyl, to give compounds of the general formula (IX)

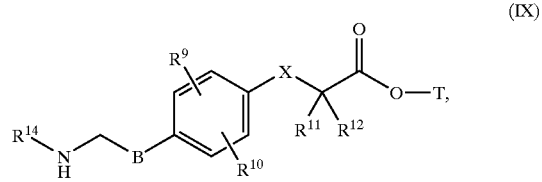

(IX)

in which
B, X, T, $R^9$, $R^{10}$, $R^{11}$, $R^{12}$ and $R^{14}$ are each as defined above,
then reacting these compounds in the presence of a base with compounds of the general formula (X)

 (X), in which
$R^{16}$ in the case of process variant [a-1] represents a group of the formula

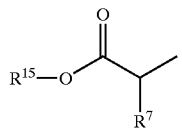

in which $R^7$ and $R^{15}$ are each as defined above or, in the case of process variant [a-2] has the meaning of $R^8$ given above and
Y represents a suitable leaving group, such as, for example halogen, mesylate or tosylate, preferably bromine or iodine,
to give compounds of the general formula (XI)

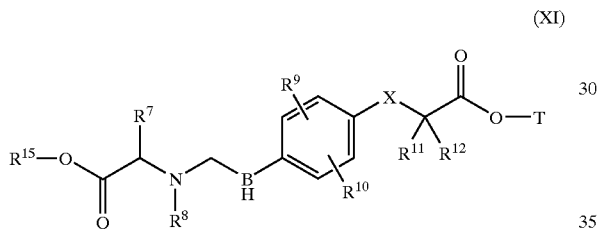 (XI)

in which
B, X, T, $R^7$, $R^8$, $R^9$, $R^{10}$, $R^{11}$, $R^{12}$ and $R^{15}$ are each as defined above,
and finally selectively hydrolysing the carboxylic acid ester grouping —COOR$^{15}$ in these compounds to the carboxylic acid, or

[b] reacting compounds of the general formula (XII)

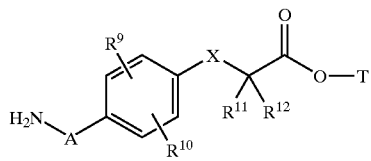 (XII)

in which
A, X, T, $R^9$, $R^{10}$, $R^{11}$ and $R^{12}$ are each as defined above
in the presence of a suitable reducing agent with compounds of the general formula (XIII)

 (XIII), in which
$R^{17}$ represents hydrogen, $(C_6-C_{10})$-aryl, 5- or 6-membered heteroaryl having up to three heteroatoms selected from the group consisting of N, O and S, or represents $(C_1-C_3)$-alkyl which for its part may be substituted by hydroxyl, trifluoromethoxy, $(C_1-C_4)$-alkoxy or phenoxy, which for their part are optionally mono- or disubstituted by trifluoromethyl, or by $(C_6-C_{10})$-aryl or 5- to 6-membered heteroaryl having up to three heteroatoms from the group consisting of N, O and S, where all aryl and heteroaryl rings mentioned may for their part in each case be mono- to trisubstituted by identical or different substituents from the group consisting of halogen, hydroxyl, $(C_1-C_6)$-alkyl, $(C_1-C_6)$-alkoxy, trifluoromethyl, trifluoromethoxy, cyano, nitro and amino,
to give compounds of the general formula (XIV)

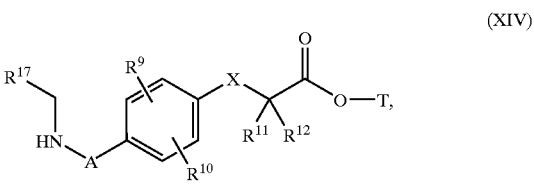 (XIV)

in which
A, X, T, $R^9$, $R^{10}$, $R^{11}$, $R^{12}$ and $R^{17}$ are each as defined above,
then reacting these compounds in the presence of a base with compounds of the general formula (XV)

 (XV)

in which
$R^7$, $R^{15}$ and Y are each as defined above
to give compounds of the general formula (XVI)

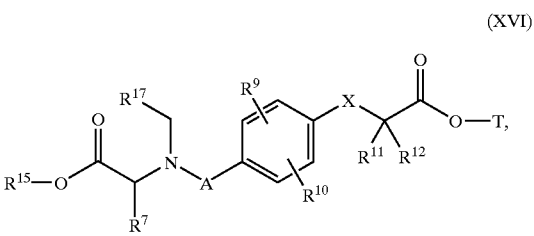 (XVI)

in which
A, X, T, R, $R^7$, $R^9$, $R^{10}$, $R^{11}$, $R^{12}$, $R^{15}$ and $R^{17}$ are each as defined above,
and finally selectively hydrolysing the carboxylic acid ester grouping —COOR$^{15}$ in these compounds to the carboxylic acid.

The entire process can also be carried out as solid-phase synthesis. In this case, the compounds of the general formula (VII) or (XII) are attached as carboxylic acid esters to a suitable support resin, the further reactions are carried out on solid phase and the target compound is finally cleaved off from the resin. Solid-phase synthesis and the attachment and the cleavage from the resin are customary standard techniques. To mention but one example from the extensive literature, reference is made to the publication "Linkers for Solid Phase Organic Synthesis", Ian W. James, *Tetrahedron* 55, 4855–4946 (1999).

The reaction (VII)+(VIII)→(IX) or (XII)+(XIII)→(XIV) is carried out in the solvents which are customary for reductive amination and inert under the reaction conditions, if appropriate in the presence of an acid. The solvents include, for example, water, dimethylformamide, tetrahydrofuran, dichloromethane, dichloro-ethane, or alcohols such as methanol, ethanol, propanol, isopropanol or butanol; it is also possible to use mixtures of the solvents mentioned. Preference is given to methanol and ethanol in each case with addition of acetic acid.

Suitable reducing agents for the reaction (VII)+(VIII)→(IX) or (XII)+(XIII)→(XIV) are complex aluminium hydrides or boron hydrides, such as, for example, diisobutylaluminium hydride, sodium borohydride, sodium triacetoxyborohydride, sodium cyanoborohydride or tetrabutylammonium borohydride, or else catalytic hydrogenation in the presence of transition metal catalysts such as, for example, palladium, platinum, rhodium or Raney nickel. Preferred reducing agents are sodium cyanoborohydride, sodium triacetoxyborohydride and tetrabutylammonium borohydride.

The reaction (VII)+(VIII)→(IX) or (XII)+(XIII)→(XIV) is generally carried out in a temperature range of from 0° C. to +40° C.

The reaction (IX)+(X)→(XI) or (XIV)+(XV)→(XVI) is carried out in the customary solvents which are inert under the reaction conditions. Preference is given to dimethylformamide, tetrahydrofuran and dioxane.

Suitable bases for the reaction (IX)+(X)→(XI) or (XIV)+(XV)→(XVI) are the customary inorganic or organic bases. Preference is given to triethylamine.

The reaction (IX)+(X)→(XI) or (XIV)+(XV)→(XVI) is generally carried out in a temperature range of from 0° C. to +100° C.

The reaction (XI)→(II) or (XVI)→(II) is carried out in the solvents which are customary for ester cleavage and inert under the reaction conditions. In the case of the ester hydrolysis, these are preferably tetrahydrofuran, dioxane and alcohols, such as methanol and ethanol, in each case in a mixture with water. In the case of the cleavage of silyl esters, preference is given to using dioxane or tetrahydrofuran.

Suitable bases for the reaction (XI)→(II) or (XVI)→(II) are, in the case of the hydrolysis, the customary inorganic bases. Preference is given to lithium hydroxide, sodium hydroxide and potassium hydroxide. In the case of the cleavage of silyl esters, preference is given to using tetrabutylammonium fluoride.

The reaction (XI)→(II) or (XVI)→(II) is generally carried out in a temperature range of from 0° C. to +100° C.

The compounds of the general formula (IV) correspond to the compounds of the general formula (IX) or (XIV) and can be prepared as described above.

The compounds of the general formulae (III), (V), (VI), (VII), (VIII), (X), (XII), (XIII) and (XV) are commercially available, known or can be prepared by customary methods [cf., for example, P. J. Brown et al., *J. Med. Chem.* 42, 3785–88 (1999)].

The compounds of the formula (I) according to the invention have a surprising and useful spectrum of pharmacological activity and can therefore be used as versatile medicaments. In particular, they are suitable for treating coronary heart diseases, for the prophylaxis of myocardial infarction and for the treatment of restenosis after coronary angioplasty or stenting. The compounds of the formula (I) according to the invention are preferably suitable for treating arteriosclerosis and hypercholesterolaemia, for increasing pathogenically low HDL levels and for lowering elevated triglyceride, fibrinogen and LDL levels. In addition, they can be used for treating obesity, diabetes, for treating the metabolic syndrome (glucose intolerance, hyperinsulinaemia, dyslipidaemia and high blood pressure owing to insulin resistance), hepatic fibrosis and cancer.

The activity of the compounds according to the invention can be examined, for example, in vitro by the transactivation assay described in the experimental section.

The activity of the compounds according to the invention in vivo can be examined, for example, by the tests described in the experimental section.

Suitable administration forms for administering the compounds of the general formula (I) are all customary administration forms, i.e. oral, parenteral, inhalative, nasal, sublingual, rectal or external, for example transdermal, preferably oral or parenteral, administration forms. In the case of parenteral administration, particular mention has to be made of intravenous, intramuscular and subcutaneous administration, for example as a subcutaneous depot. Very particular preference is given to oral administration.

Here, the active compounds can be administered on their own or in the form of preparations. Preparations suitable for oral administration are, inter alia, tablets, capsules, pellets, sugar-coated tablets, pills, granules, solid and liquid aerosols, syrups, emulsions, suspensions and solutions. Here, the active compound has to be present in such an amount that a therapeutic effect is obtained. In general, the active compound can be present in a concentration of from 0.1 to 100% by weight, in particular from 0.5 to 90% by weight, preferably from 5 to 80% by weight. In particular, the concentration of active compound should be 0.5–90% by weight, i.e. the active compound should be present in amounts sufficient to reach the dosage range stated.

To this end, the active compounds can be converted in a manner known per se into the customary preparations. This is carried out using inert non-toxic pharmaceutically suitable excipients, auxiliaries, solvents, vehicles, emulsifiers and/or dispersants.

Auxiliaries which may be mentioned are, for example: water, non-toxic organic solvents, such as, for example, paraffins, vegetable oils (for example sesame oil), alcohols (for example ethanol, glycerol), glycols (for example polyethylene glycol), solid carriers, such as natural or synthetic ground minerals (for example talc or silicates), sugar (for example lactose), emulsifiers, dispersants (for example polyvinylpyrrolidone) and glidants (for example magnesium sulphate).

In the case of oral administration, the tablets may, of course, also contain additives such as sodium citrate, together with additives such as starch, gelatine and the like. Aqueous preparations for oral administration may furthermore comprise flavour improvers or colorants.

In the case of oral administration, preference is given to administering dosages of from 0.001 to 5 mg/kg, preferably from 0.005 to 3 mg/kg, of body weight per 24 hours.

The embodiments below illustrate the invention. The invention is not limited to the examples.

The following abbreviations used represent:

| | |
|---|---|
| Ac | Acetyl |
| Bu | Butyl |
| TLC | Thin-layer chromatography |
| DCI | Direct chemical ionization (in MS) |
| DCM | Dichloromethane |
| DIC | Diisopropylcarbodiimide |
| DMAP | 4-N,N-Dimethylaminopyridine |

-continued

| | |
|---|---|
| DMF | N,N-Dimethylformamide |
| DMSO | Dimethyl sulphoxide |
| EDC | N'-(3-Dimethylaminopropyl)-N-ethlylcarbodiimide × HCl |
| EI | Electron impact ionization (in MS) |
| ESI | Electron spray ionization (in MS) |
| Et | Ethyl |
| sat. | Saturated |
| HATU | O-(7-Azabenzotriazol-1-yl)-N,N,N',N'-tetramethyluronium hexafluorophosphate |
| HOBt | 1-Hydroxy-1H-benzotriazole × H$_2$O |
| HPLC | High-pressure, high-performance liquid chromatography |
| LC-MS | Liquid chromatography-coupled mass spectroscopy |
| Me | Methyl |
| MS | Mass spectroscopy |
| NMR | Nuclear magnetic resonance spectroscopy |
| RF | Reflux |
| R$_f$ | Retention index (in TLC) |
| RT | Room temperature |
| R$_t$ | Retention time (in HPLC) |
| TBAF | Tetrabutylammonium fluoride |
| TBAI | Tetrabutylammonium iodide |
| TFA | Trifluoroacetic acid |
| THF | Tetrahydrofuran |

STARTING MATERIALS I

Example I-1 tert-Butyl 2-methylpropionate

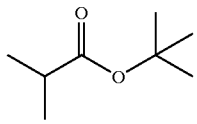

With ice-cooling, a solution of 73.0 g (0.985 mol) of tert-butanol, 190 g (1.877 mol) of triethylamine and 0.573 g (0.0047 mol) of DMAP in 750 ml of dichloromethane is treated with a solution of 100 g (0.939 mmol) of isobutyryl chloride in 150 ml of dichloromethane, and the mixture is then stirred overnight. 500 ml of 2 M hydrochloric acid are then added, the aqueous phase is extracted with dichloromethane and the combined organic phases are washed with water, sat. NaHCO$_3$ solution and sat. NaCl solution, dried over sodium sulphate and concentrated. Distillative purification of the crude product gives 65.5 g (48%) of tert-butyl 2-methylpropionate.

$^1$H-NMR (200 MHz, CDCl$_3$): δ=1.11 (d, 6H); 1.44 (s, 9H); 2.42 (sept., 1H).

Example I-2 tert-Butyl 3-(4-bromophenyl)-2,2-dimethylpropionate

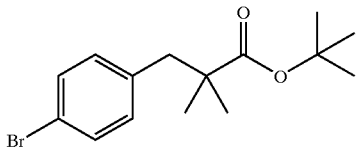

At −78° C., 34.7 ml (69.4 mmol) of a 2 M lithium diisopropylamide solution are slowly added dropwise to a solution of 10.0 g (69.34 mmol) of tert-butyl 2-methylpropionate (Example I-1) in 100 ml of tetrahydrofuran. After the addition has ended, the mixture is stirred at −78° C. for 1 h, and a solution of 15.76 g (63.04 mmol) of 4-bromobenzyl bromide in 10 ml of tetrahydrofuran is then added and the mixture is stirred at −78° C. for 1 h. The reaction is then warmed to room temperature and poured into 100 ml of 1 N hydrochloric acid, the phases are separated and the aqueous phase is extracted 3× with diethyl ether. The combined organic phases are washed with NaHCO$_3$ solution, dried over sodium sulphate and freed from the solvent under reduced pressure. Distillative purification of the residue under oil pump vacuum gives 16.75 g (85%) of tert-butyl 3-(4-bromophenyl)-2,2-dimethylpropionate.

$^1$H-NMR (200 MHz, DMSO): δ=1.06 (s, 6H); 1.38 (s, 9H); 2.74 (s, 2H); 7.10 (d, 2H); 7.47 (d, 2H).

Example I-3 tert-Butyl 3-(4-formylphenyl)-2,2-dimethylpropionate

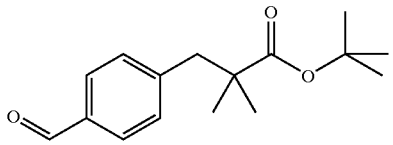

At −75° C., 13.5 ml (22.98 mmol) of a 1.7 M tert-butyllithium solution in pentane are slowly added to a solution of 6.00 g (19.16 mmol) of tert-butyl 3-(4-bromophenyl)-2,2-dimethylpropionate (Example I-2) in 80 ml of tetrahydrofuran, the temperature being kept below −60° C. The mixture is stirred for 15 min, and 1.82 g (24.90 mmol) of N,N-dimethylformamide are then added and the mixture is stirred at −75° C. for a further 4 h. The mixture is slowly warmed to −20° C. and, with vigorous stirring, admixed with 20 ml of water, and then warmed to room temperature. The aqueous phase is extracted 3× with diethyl ether and the combined organic phases are dried over sodium sulphate/sodium carbonate and freed from the solvent under reduced pressure. Distillation of the residue under oilpump vacuum gives 2.54 g (51%) of tert-butyl 3-(4-formylphenyl)-2,2-dimethylpropionate.

$^1$H-NMR (300 MHz, CDCl$_3$): δ=1.16 (s, 6H); 1.42 (s, 9H); 2.90 (s, 2H); 7.32 (d, 2H); 7.78 (d, 2H); 9.98 (s, 1H).

Example I-4 tert-Butyl 2-(4-formylphenoxy)-2-methylpropionate

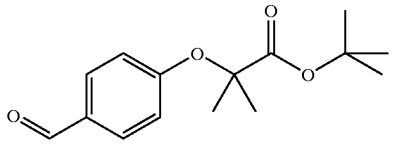

A solution of 24.4 g (200 mmol) of 4-hydroxybenzaldehyde in 100 ml of dimethylformamide is treated with 97.75 g (300 mmol) of caesium carbonate and stirred at 90° C. for 1 h. A solution of 66.93 g (300 mmol) of tert-butyl 2-bromisobutyrate in 100 ml of dimethylformamide is then added dropwise, and the mixture is stirred at 90° C. overnight. The dimethylformamide is distilled off under reduced pressure and the residue is then taken up in ethyl acetate, washed 2× with water, 2× with 1 N aqueous sodium hydroxide solution and 1× with sat. NaCl solution, dried over sodium sulphate and freed from the solvent under reduced pressure. This gives 16.6 g (31%) of tert-butyl 2-(4-formylphenoxy)-2-methylpropionate.

$^1$H-NMR (200 MHz, CDCl$_3$): δ=1.40 (s, 9H); 1.63 (s, 6H); 6.90 (d, 2H); 7.78 (d, 2H); 9.88 (s, 1H).

Example I-5 tert-Butyl 3-(4-{[(2-furylmethyl)amino] methyl}phenyl)-2,2-dimethylpropionate

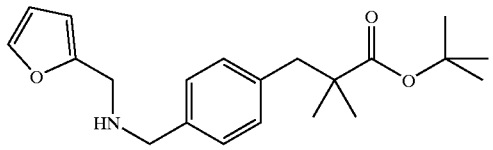

At room temperature, a solution of 1.00 g (3.81 mmol) of tert-butyl 3-(4-formylphenyl)-2,2-dimethylpropionate (Example I-3) and 0.37 g (3.81 mmol) of furfurylamine in 10 ml of dichloroethane is stirred for 30 min, 1.21 g (5.72 mmol) of sodium triacetoxyborohydride are added and the mixture is then stirred at room temperature for 22 h. 6 ml of sat. NaHCO$_3$ solution and 10 ml of ethyl acetate are then added, the phases are separated, the aqueous phase is extracted 2× with ethyl acetate and the combined organic phases are dried over sodium sulphate. The solvent is removed under reduced pressure, and chromatographic purification on silica gel (cyclohexane→cyclohexane/ethyl acetate 10:1→2:1) then gives 720 mg (55%) of tert-butyl 3-{(4-[(2-furylmethyl)amino]methyl}phenyl)-2,2-dimethylpropionate.

$^1$H-NMR (300 MHz, CDCl$_3$): δ=1.11 (s, 6H); 1.42 (s, 9H); 1.62 (broad s, 1H); 2.70 (s, 2H); 3.76 (s, 2H); 3.80 (s, 2H); 6.18 (d, 1H); 6.32 (dd, 1H); 7.10 (d, 2H); 7.20 (d, 2H); 7.35 (d, 1H).

Example I-6 tert-Butyl 3-[4-(anilinomethyl)phenyl]-2,2-dimethylpropionate

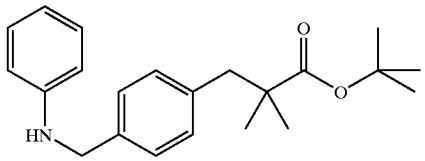

Similarly to the procedure of Example I-5, 200 mg (0.762 mmol) of tert-butyl 3-(4-formylphenyl)-2,2-dimethylpropionate (Example I-3), 71 mg (0.762 mmol) of aniline and 210 mg (0.991 mmol) of sodium triacetoxyborohydride in 2 ml of dichloroethane are converted into 223 mg (86%) of tert-butyl 3-[4-(anilinomethyl)phenyl]-2,2-dimethylpropionate.

$^1$H-NMR (400 MHz, CDCl$_3$): δ=1.11 (s, 6H); 1.42 (s, 9H); 2.81 (s, 2H); 3.98 (broad s, 1H); 4.29 (s, 2H); 6.64 (d, 2H); 6.71 (t, 1H); 7.12 (d, 2H); 7.17 (t, 2H); 7.25 (d, 2H).

Example I-7 tert-Butyl 2,2-dimethyl-3-(4-{[(4-methylphenyl) amino]methyl}phenyl)propionate

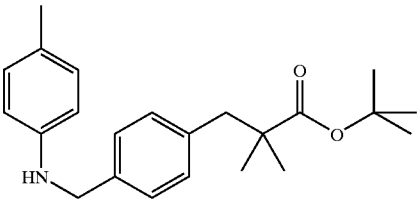

Similarly to the procedure of Example I-5, 200 mg (0.762 mmol) of tert-butyl 3-(4-formylphenyl)-2,2-dimethylpropionate (Example I-3), 82 mg (0.762 mmol) of toluidine and 210 mg (0.991 mmol) of sodium triacetoxyborohydride in 2 ml of dichloroethane are converted into 206 mg (76%) of tert-butyl 2,2-dimethyl-3-(4-{[(4-methylphenyl)amino]methyl}-phenyl)propionate.

$^1$H-NMR (400 MHz, CDCl$_3$): δ=1.11 (s, 6H); 1.42 (s, 9H); 2.23 (s, 3H); 2.81 (s, 2H); 3.87 (broad s, 1H); 4.27 (s, 2H); 6.57 (d, 2H); 6.98 (d, 2H); 7.12 (d, 2H); 7.25 (d, 2H).

Example I-8

Methyl 2-{[4-(2-tert-butoxy-1,1-dimethyl-2-oxoethoxy)benzyl]amino}butyrate

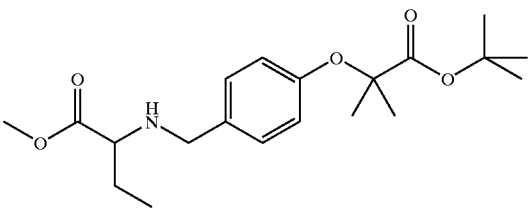

Similarly to the procedure of Example I-5, 1.20 g (4.54 mmol) of tert-butyl 2-(4-formylphenoxy)-2-methylpropionate (Example I-4) and 0.70 g (4.54 mmol) of methyl DL-2-aminobutyrate are reacted at room temperature with 0.92 g (9.08 mmol) of triethylamine and 1.44 g (6.81 mmol) of sodium triacetoxyborohydride in 10 ml of dichloroethane. A further 0.9 g (4.25 mmol) of sodium triacetoxyborohydride and 0.35 g (2.27 mmol) of methyl DL-2-aminobutyrate are added and the mixture is heated at 40° C. for 3 h, giving 1.47 g (89%) of methyl 2-{[4-(2-tert-butoxy-1,1-dimethyl-2-oxoethoxy)benzyl]amino}butyrate.

$^1$H-NMR (300 MHz, DMSO): δ=0.84 (t, 3H); 1.38 (s, 9H); 1.47 (s, 6H); 1.57 (dt, 2H); 2.29 (broad s, 1H); 3.08 (t, 1H); 3.47 (d, 1H); 3.62 (s, 3H); 3.65 (d, 2H); 6.73 (d, 2H); 7.18 (d, 2H).

Example I-9 tert-Butyl 3-(4-{[(2-ethoxy-2-oxoethyl)(2-furylmethyl)amino]methyl}phenyl)-2,2-dimethylpropionate

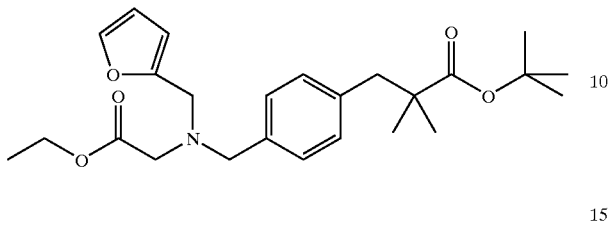

A solution of 600 mg (1.75 mmol) of tert-butyl 3-(4-{[(2-furylmethyl)amino]-methyl}phenyl)-2,2-dimethylpropionate (Example I-5), 323 mg (0.87 mmol) of tetra-n-butylammonium iodide and 265 mg (2.62 mmol) of triethylamine in 10 ml of THF is treated with 438 mg (2.62 mmol) of ethyl bromoacetate and heated at reflux overnight. After cooling, the mixture is concentrated under reduced pressure, the residue is taken up in water and ethyl acetate, the aqueous phase is extracted 2× with ethyl acetate and the combined organic phases are washed with NaCl solution and dried over sodium sulphate. The solvent is removed under reduced pressure, and chromatographic purification on silica gel (cyclohexane→cyclohexane/ethyl acetate 10:1) then gives 702 mg (94%) of tert-butyl 3-(4-{[(2-ethoxy-2-oxoethyl)(2-furylmethyl)amino]methyl}phenyl)-2,2-di methylpropionate.

$^1$H-NMR (400 MHz, CDCl$_3$): δ=1.11 (s, 6H); 1.27 (t, 3H); 1.42 (s, 9H); 2.80 (s, 2H); 3.31 (s, 2H); 3.76 (s, 2H); 3.84 (s, 2H); 4.17 (q, 2H); 6.20 (d, 1H); 6.32 (dd, 1H); 7.10 (d, 2H); 7.25 (d, 2H); 7.38 (d, 1H).

Example I-10 tert-Butyl 3-(4-{[N-(2-ethoxy-2-oxo)ethyl-N-phenylamino]methyl}phenyl)-2,2-dimethylpropionate

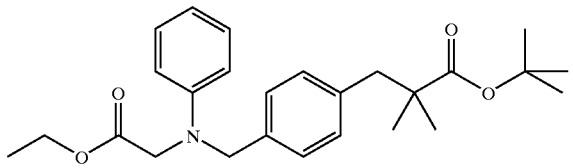

Similarly to the procedure of Example I-9, 198 mg (0.583 mmol) of tert-butyl 3-[4-(anilinomethyl)phenyl]-2,2-dimethylpropionate (Example I-6), 108 mg (0.292 mmol) of tetra-n-butylammonium iodide, two portions of in each case 89 mg (0.875 mmol) of triethylamine and three portions of in each case 146 mg (0.875 mmol) of ethyl bromoacetate in 2 ml of tetrahydrofuran and 2 ml of dimethylformamide give 191 mg (77%) of tert-butyl 3-(4-{[(2-ethoxy-2-oxoethyl)(2-phenyl)amino]methyl}phenyl)-2,2-dimethylpropionate.

$^1$H-NMR (200 MHz, CDCl$_3$): δ=1.11 (s, 6H); 1.25 (t, 3H); 1.42 (s, 9H); 2.70 (s, 2H); 4.05 (s, 2H); 4.20 (q, 2H); 4.62 (s, 2H); 6.69 (d, 2H); 6.73 (t, 1H); 7.07–7.25 (m, 6H).

Example I-11 tert-Butyl 3-(4-{[N-(2-ethoxy-2-oxo)ethyl-N-(4-methylphenyl)amino]methyl}-phenyl)-2,2-dimethylpropionate

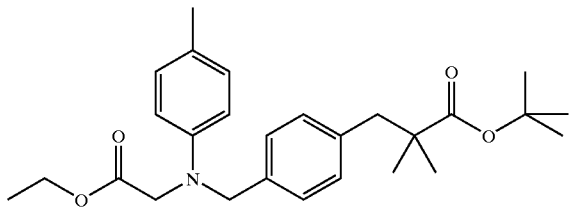

Similarly to the procedure of Example I-9, 181 mg (0.512 mmol) of tert-butyl 2,2-dimethyl-3-(4-{[(4-methylphenyl)amino]methyl}phenyl)propionate (Example I-7), 95 mg (0.256 mmol) of tetra-n-butylammonium iodide, two portions of in each case 78 mg (0.768 mmol) of triethylamine and three portions of in each case 128 mg (0.768 mmol) of ethyl bromoacetate in 2 ml of tetrahydrofuran and 2 ml of dimethylformamide give 176 mg (78%) of tert-butyl 3-(4-{[N-(2-ethoxy-2-oxo)ethyl-N-(4-methylphenyl)-amino]methyl}phenyl)-2,2-dimethylpropionate.

$^1$H-NMR (200 MHz, CDCl$_3$): 1.11 (s, 6H); 1.25 (t, 3H); 1.42 (s, 9H); 2.22 (s, 3H); 2.80 (s, 2H); 4.02 (s, 2H); 4.19 (q, 2H); 4.59 (s, 2H); 6.60 (d, 2H); 7.00 (d, 2H); 7.10 (d, 2H); 7.17 (d, 2H).

Example I-12

N-[4-(3-tert-Butoxy 2,2-dimethyl-3-oxopropyl)benzyl]-N-(2-furylmethyl)glycine

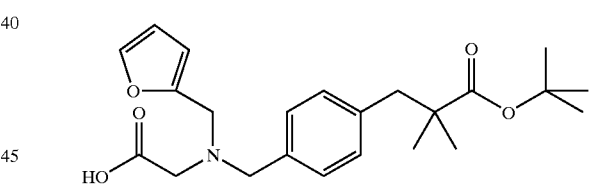

A solution of 785 mg (1.83 mmol) of tert-butyl 3-(4-{[(2-ethoxy-2-oxoethyl)(2-furylmethyl)amino]methyl}phenyl)-2,2-dimethylpropionate (Example I-9) in 15 ml of ethanol is admixed with 5.5 ml (5.5 mmol) of 1 N aqueous sodium hydroxide solution and heated at 80° C. for 1 h. After cooling, the mixture is concentrated under reduced pressure and the residue is taken up in a little water, acidified with 1 N hydrochloric acid and extracted 3× with ethyl acetate. The combined organic extracts are washed 2× with sat. NaCl solution, dried over sodium sulphate and freed from the solvent under reduced pressure. This gives 728 mg (99%) of N-[4-(3-tert-butoxy-2,2-dimethyl-3-oxopropyl)benzyl]-N-(2-furylmethyl)glycine.

$^1$H-NMR (200 MHz, DMSO): δ=1.06 (s, 6H); 1.37 (s, 9H); 2.74 (s, 2H); 3.24 (s, 2H); 3.76 (s, 2H); 3.84 (s, 2H); 6.32 (m, 1H); 6.41 (m, 1H); 7.11 (d, 2H); 7.26 (d, 2H); 7.63 (d, 1H); 12.20 (broad s, 1H).

Example I-13

N-[4-(3-tert-Butoxy-2,2-dimethyl-3-oxopropyl)benzyl]-N-phenylglycine

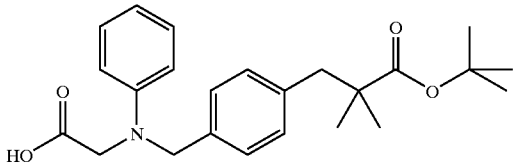

Similarly to the procedure of Example I-12, 175 mg (0.411 mmol) of tert-butyl 3-(4-{[(2-ethoxy-2-oxoethyl)(2-phenyl)amino]methyl}phenyl)-2,2-dimethylpropionate (Example I-10) and 1.23 ml (1.23 mmol) of 1 N aqueous sodium hydroxide solution in 3 ml of ethanol give 162 mg (99%) of N-[4-(3-tert-butoxy-2,2-dimethyl-3-oxopropyl)benzyl]-N-phenylglycine.

$^1$H-NMR (300 MHz, DMSO): δ=1.04 (s, 6H); 1.36 (s, 9H); 2.73 (s, 2H); 4.12 (s, 2H); 4.56 (s, 2H); 6.56 (d, 2H); 6.61 (t, 1H); 7.07 (d, 2H); 7.11 (d, 2H); 7.19 (d, 1H); 12.53 (broad s, 1H).

Example I-14

N-[4-(3-tert-Butoxy-2,2-dimethyl-3-oxopropyl)benzyl]-N-(4-methylphenyl)glycine

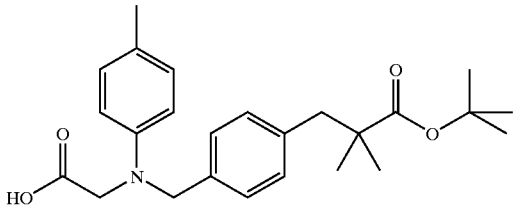

Similarly to the procedure of Example I-12, 153 mg (0.348 mmol) of tert-butyl 3-(4-{[N-(2-ethoxy-2-oxo)ethyl-N-(4-methylphenyl)amino]methyl}phenyl)-2,2-dimethylpropionate (Example I-11) and 1.23 ml (1.23 mmol) of 1 N aqueous sodium hydroxide solution in 3 ml of ethanol give 141 mg (99%) of N-[4-(3-tert-butoxy-2,2-dimethyl-3-oxopropyl)benzyl]-N-(4-methylphenyl)glycine.

$^1$H-NMR (300 MHz, DMSO): δ=1.04 (s, 6H); 1.36 (s, 9H); 2.14 (s, 3H); 2.72 (s, 2H); 4.08 (s, 2H); 4.52 (s, 2H); 6.48 (d, 2H); 6.90 (d, 2H); 7.08 (d, 2H); 7.18 (d, 2H); 12.48 (broad s, 1H).

Example I-15

2-{[4-(2-tert-Butoxy-1,1-dimethyl-2-oxoethoxy)benzyl]amino}butyric acid

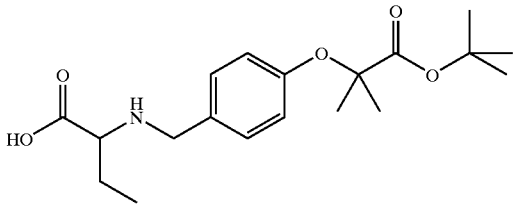

Similarly to the procedure of Example I-12, 750 mg (2.05 mmol) of methyl 2-{[4-(2-tert-butoxy-1,1-dimethyl-2-oxoethoxy)benzyl]amino}butyrate (Example I-8) and 6.20 ml (6.20 mmol) of 1 N aqueous sodium hydroxide solution in 6 ml of ethanol give 640 mg (89%) of 2-{[4-(2-tert-butoxy-1,1-dimethyl-2-oxoethoxy)benzyl]-amino}butyric acid.

$^1$H-NMR (300 MHz, DMSO): δ=0.91 (t, 3H); 1.40 (s, 9H); 1.51 (s, 6H); 1.84 (m, 2H); 3.25 (broad s, 1H); 3.57 (t, 1H); 3.99 (s, 2H); 6.81 (d, 2H); 7.38 (d, 2H).

WORKING EXAMPLES 1

Example I-1 tert-Butyl 3-(4-{[(2-(2,4-dimethylphenyl)amino-2-oxoethyl)(2-furylmethyl)amino]-methyl}phenyl)-2,2-dimethylpropionate

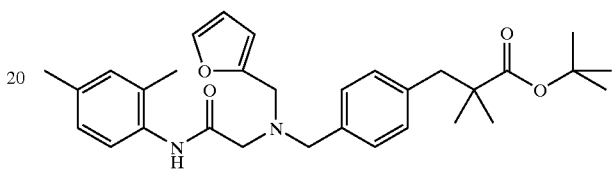

At 0° C., 88 mg (0.648 mmol) of 1-hydroxy-1H-benzotriazole, 124 mg (0.648 mmol) of 1-ethyl-3-(3-dimethylamino)propylcarbodiimide hydrochloride, 151 mg (1.494 mmol) of N-methylmorpholine and 3 mg (0.025 mmol) of 4-dimethylaminopyridine are added to a solution of 200 mg (0.498 mmol) of N-[4-(3-tert-butoxy-2,2-dimethyl-3-oxopropyl)benzyl]-N-(2-furylmethyl)glycine (Example I-12) and 91 mg (0.747 mmol) of 2,4-dimethylaniline in 8 ml of dimethylformamide, and the solution is stirred at this temperature for 1 h. The mixture is then stirred at room temperature for 9 h and then admixed with 10 ml of water. The aqueous phase is extracted 2× with ethyl acetate and the combined organic phases are washed with 1 N hydrochloric acid, sat. NaHCO$_3$ solution and sat. NaCl solution, dried over sodium sulphate and freed from the solvent under reduced pressure. Chromatographic purification of the residue on silica gel (cyclohexane/ethyl acetate 10:1→3:1) gives 228 mg (91%) of tert-butyl 3-(4-{[(2-(2,4-dimethylphenyl)amino-2-oxoethyl)(2-furylmethyl)amino]methyl}phenyl)-2,2-dimethylpropionate.

$^1$H-NMR (200 MHz, CDCl$_3$): δ=1.10 (s, 6H); 1.40 (s, 9H); 2.26 (s, 3H); 2.28 (s, 3H); 2.80 (s, 2H); 3.29 (s, 2H); 3.71 (s, 2H); 3.74 (s, 2H); 6.25 (d, 1H); 6.32 (dd, 1H); 6.99 (m, 2H); 7.11 (d, 2H); 7.23 (d, 2H); 7.37 (d, 1H); 7.84 (d, 1H) 9.12 (broad s, 1H).

Example 1-2 tert-Butyl 3-(4-{[(2-(4-methoxy-2,5-dimethylphenyl)amino-2-oxoethyl)(2-furylmethyl)amino]methyl}phenyl)-2,2-dimethylpropionate

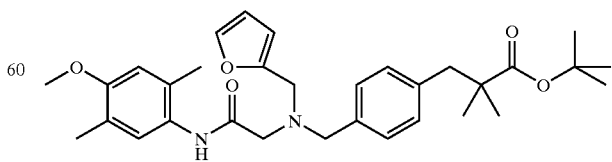

Similarly to the procedure of Example 1-1, 200 mg (0.498 mmol) of N-[4-(3-tert-butoxy-2,2-dimethyl-3-oxopropyl)

benzyl]-N-(2-furylmethyl)glycine (Example I-12), 113 mg (0.747 mmol) of 4-methoxy-2,5-dimethylaniline, 88 mg (0.648 mmol) of 1-hydroxy-1H-benzotriazole, 124 mg (0.648 mmol) of 1-ethyl-3-(3-dimethylamino) propylcarbodiimide hydrochloride, 151 mg (1.494 mmol) of N-methylmorpholine and 3 mg (0.025 mmol) of 4-dimethylaminopyridine in 8 ml of dimethylformamide are converted into 241 mg (90%) of tert-butyl 3-(4-{[(2-(4-methoxy-2,5-dimethylphenyl)amino-2-oxoethyl)(2-furylmethyl)amino]methyl}phenyl)-2,2-dimethylpropionate.

¹H-NMR (200 MHz, DMSO): δ=1.05 (s, 6H); 1.35 (s, 9H); 2.08 (s, 3H); 2.14 (s, 3H); 2.75 (s, 2H); 3.18 (s, 2H); 3.69 (s, 2H); 3.74 (s, 3H); 3.76 (s, 2H); 6.35 (d, 1H); 6.41 (dd, 1H); 6.75 (s, 1H); 7.11 (d, 2H); 7.28 (d, 2H); 7.31 (s, 1H); 7.61 (d, 1H); 9.02 (broad s, 1H).

Example 1-3 tert-Butyl 3-(4-{[N-(2-(2,4-dimethylphenyl)amino-2-oxo)ethyl-N-phenylamino]-methyl}phenyl)-2,2-dimethylpropionate

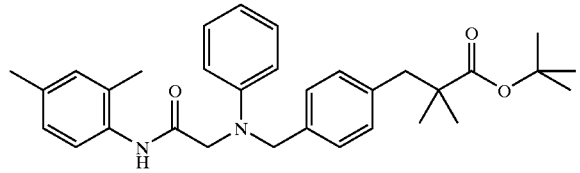

Similarly to the procedure of Example 1-1, 65 mg (0.164 mmol) of N-[4-(3-tert-butoxy-2,2-dimethyl-3-oxopropyl)benzyl]-N-phenylglycine (Example I-13), 30 mg (0.245 mmol) of 2,4-dimethylaniline, 29 mg (0.213 mmol) of 1-hydroxy-1H-benzotriazole, 41 mg (0.213 mmol) of 1-ethyl-3-(3-dimethylamino)propylcarbodiimide hydrochloride, 50 mg (0.491 mmol) of N-methylmorpholine and 0.2 mg (0.002 mmol) of 4-dimethylaminopyridine in 2 ml of dimethylformamide are converted into 65 mg (79%) of tert-butyl 3-(4-{[N-(2-(2,4-dimethylphenyl)amino-2-oxo)ethyl-N-phenylamino]methyl}phenyl)-2,2-dimethylpropionate.

¹H-NMR (200 MHz, CDCl₃): δ=1.10 (s, 6H); 1.41 (s, 9H); 1.90 (s, 3H); 2.26 (s, 3H); 2.79 (s, 2H); 4.09 (s, 2H); 4.66 (s, 2H); 6.80–6.95 (m, 4H); 6.98 (d, 1H); 7.12 (s, 4H); 7.27 (m, 2H); 7.67 (d, 1H); 8.11 broad s, 1H).

Example 1-4 tert-Butyl 3-(4-{[N-(2-(4-methoxy-2,5-dimethylphenyl)amino-2-oxo)ethyl-N-phenylamino]methyl}phenyl)-2,2-dimethylpropionate

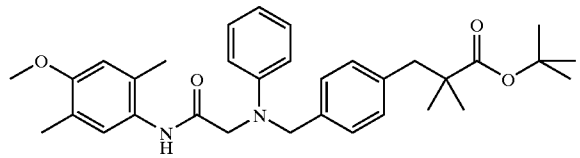

Similarly to the procedure of Example 1-1, 65 mg (0.164 mmol) of N-[4-(3-tert-butoxy-2,2-dimethyl-3-oxopropyl)benzyl]-N-phenylglycine (Example I-13), 37 mg (0.245 mmol) of 4-methoxy-2,5-dimethylaniline, 29 mg (0.213 mmol) of 1-hydroxy-1H-benzotriazole, 41 mg (0.213 mmol) of 1-ethyl-3-(3-dimethylamino)propylcarbodiimide hydrochloride, 50 mg (0.491 mmol) of N-methylmorpholine and 0.2 mg (0.002 mmol) of 4-dimethylaminopyridine in 2 ml of dimethylformamide are converted into 78 mg (90%) of tert-butyl 3-(4-{[N-(2-(4-methoxy-2,5-dimethylphenyl)amino-2-oxo)ethyl-N-phenylamino]methyl}phenyl)-2,2-dimethylpropionate.

¹H-NMR (200 MHz, CDCl₃): δ=1.11 (s, 6H); 1.42 (s, 9H); 1.96 (s, 3H); 2.16 (s, 3H); 2.80 (s, 2H); 3.77 (s, 3H); 4.09 (s, 2H); 4.67 (s, 2H); 6.57 (s, 1H); 6.83 (dd, 1H); 6.89 (d, 2H); 7.13 (s, 4H); 7.24 (d, 2H); 7.34 (m, 1H); 7.94 (broad s, 1H).

Example 1-5 tert-Butyl 3-(4-{[N-(2-(2,4-dimethylphenyl)amino-2-oxo)ethyl-N-(4-methylphenyl)amino]methyl}phenyl)-2,2-dimethylpropionate

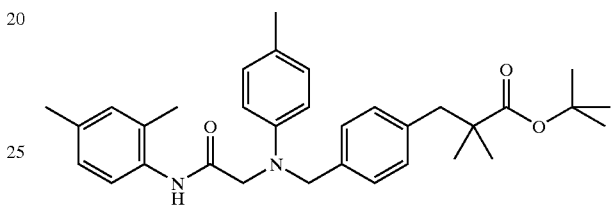

Similarly to the procedure of Example 1-1, 50 mg (0.121 mmol) of N-[4-(3-tert-butoxy-2,2-dimethyl-3-oxopropyl)benzyl]-N-(4-methylphenyl)glycine (Example I-14), 22 mg (0.182 mmol) of 2,4-dimethylaniline, 21 mg (0.158 mmol) of 1-hydroxy-1H-benzotriazole, 30 mg (0.158 mmol) of 1-ethyl-3-(3-dimethylamino)propylcarbodiimide hydrochloride, 37 mg (0.364 mmol) of N-methylmorpholine and 0.1 mg (0.001 mmol) of 4-dimethylaminopyridine in 2 ml of dimethylformamide are converted into 40 mg (64%) of tert-butyl-3-(4-{[N-(2-(2,4-dimethylphenyl)amino-2-oxo)ethyl-N-(4-methylphenyl)amino]methyl}phenyl)-2,2-dimethylpropionate.

¹H-NMR (300 MHz, CDCl₃): δ=1.10 (s, 6H); 1.40 (s, 9H); 1.92 (s, 3H); 2.27 (s, 6H); 2.79 (s, 2H); 4.02 (s, 2H); 4.58 (s, 2H); 6.80 (d, 2H); 6.91 (s, 1H); 6.98 (d, 1H); 7.06 (d, 2H); 7.11 (d, 2H); 7.13 (d, 2H); 7.67 (d, 1H); 8.18 (broad s, 1H).

Example 1-6 tert-Butyl 3-(4-{[N-(2-(4-methoxy-2,5-dimethylphenyl)amino-2-oxo)ethyl-N-(4-methylphenyl)amino]methyl}phenyl)-2,2-dimethylpropionate

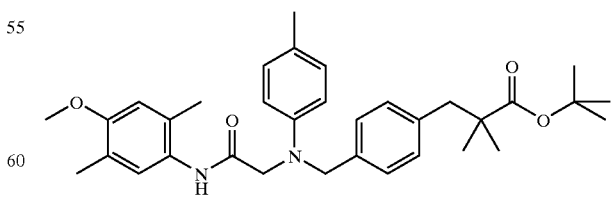

Similarly to the procedure of Example 1-1, 50 mg (0.121 mmol) of N-[4-(3-tert-butoxy-2,2-dimethyl-3-oxopropyl)benzyl]-N-(4-methylphenyl)glycine (Example I-14), 28 mg (0.182 mmol) of 4-methoxy-2,5-dimethylaniline, 21 mg (0.158 mmol) of 1-hydroxy-1H-benzotriazole, 30 mg (0.158 mmol) of 1-ethyl-3-(3-dimethylamino)propylcarbodiimide hydrochloride, 37 mg (0.364 mmol) of N-methylmorpholine and 0.1 mg (0.001 mmol) of 4-dimethylaminopyridine in 2 ml of dimethylformamide are converted into 58 mg (88%) of tert-butyl-3-(4-{[N-(2-(4-methoxy-2,5-dimethylphenyl)amino-2-oxo)ethyl-N-(4-methylphenyl)amino]-methyl}phenyl)-2,2-dimethylpropionate.

$^1$H-NMR (300 MHz, CDCl$_3$): δ=1.10 (s, 6H); 1.41 (s, 9H); 1.96 (s, 3H); 2.15 (s, 3H); 2.26 (s, 3H); 2.79 (s, 2H); 3.77 (s, 3H); 4.02 (s, 2H); 4.60 (s, 2H); 6.57 (s, 1H); 6.80 (d, 2H); 7.07 (d, 2H); 7.10 (d, 2H); 7.13 (d, 2H); 7.37 (s, 1H); 8.01 (broad s, 1H).

Example 1-7 tert-Butyl 2-(4-{[(1-{[(2,4-dimethylphenyl)amino]carbonyl}propyl)-amino]methyl}-phenoxy)-2-methylpropionate

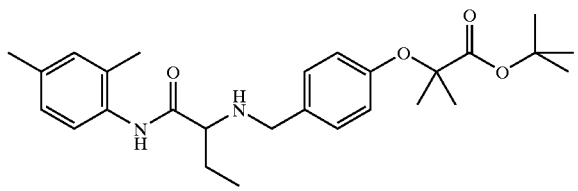

Similarly to the procedure of Example 1-1, 320 mg (0.90 mmol) of 2-{[4-(2-tert-butoxy-1,1-dimethyl-2-oxoethoxy)benzyl]amino}butyric acid (Example I-15), 160 mg (1.36 mmol) of 2,4-dimethylaniline, 160 mg (1.18 mmol) of 1-hydroxy-1H-benzotriazole, 230 mg (1.18 mmol) of 1-ethyl-3-(3-dimethylamino)propylcarbodiimide hydrochloride, 270 mg (2.71 mmol) of N-methylmorpholine and 1 mg (0.01 mmol) of 4-dimethylaminopyridine in 5 ml of dimethylformamide are converted into 190 mg (46%) of tert-butyl 2-(4-{[(1-{[(2,4-dimethylphenyl)-amino]carbonyl}propyl)amino]methyl}phenoxy)-2-methylpropionate.

$^1$H-NMR (200 MHz, CDCl$_3$): δ=0.99 (t, 3H); 1.43 (s, 9H); 1.56 (s, 6H); 1.74 (m, 2H); 2.21 (s, 3H); 2.28 (s, 3H); 3.22 (dd, 1H); 3.69 (d, 1H); 3.82 (d, 1H); 6.83 (d, 2H); 6.98 (s, 1H); 7.02 (d, 1H); 7.18 (d, 2H); 7.93 (d, 1H); 9.32 (broad s, 1H).

Example 1-8 tert-Butyl 2-(4-{[(1-{[(4-methoxy-2,5-dimethylphenyl)amino]carbonyl}propyl)-amino]methyl}phenoxy)-2-methylpropionate

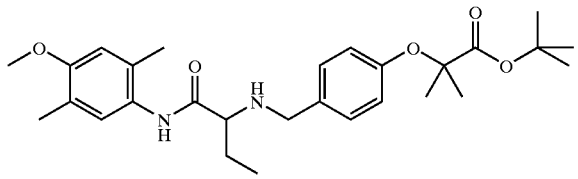

Similarly to the procedure of Example 1-1, 320 mg (0.90 mmol) of 2-{[4-(2-tert-butoxy-1,1-dimethyl-2-oxoethoxy)benzyl]amino}butyric acid (Example I-15), 210 mg (1.36 mmol) of 4-methoxy-2,5-dimethylaniline, 160 mg (1.18 mmol) of 1-hydroxy-1H-benzotriazole, 230 mg (1.18 mmol) of 1-ethyl-3-(3-dimethylamino)propylcarbodiimide hydrochloride, 270 mg (2.71 mmol) of N-methylmorpholine and 1 mg (0.01 mmol) of 4-dimethylaminopyridine in 5 ml of dimethylformamide are converted into 130 mg (30%) of tert-butyl 2-(4-{[(1-{[(4-methoxy-2,5-dimethylphenyl)amino]carbonyl}propyl)amino]methyl}phenoxy)-2-methylpropionate.

$^1$H-NMR (200 MHz, CDCl$_3$): δ=0.99 (t, 3H); 1.44 (s, 9H); 1.56 (s, 6H); 1.74 (m, 2H); 2.19 (s, 3H); 2.22 (s, 3H); 3.22 (dd, 1H); 3.71 (d, 1H); 3.80 (s, 3H); 3.82 (d, 1H); 6.64 (s, 1H); 6.83 (d, 2H); 7.19 (d, 2H); 7.65 (s, 1H); 9.13 (broad s, 1H).

Example 1-9

3-(4-{[(2-(2,4-Dimethylphenyl)amino-2-oxoethyl)(2-furylmethyl)amino]methyl}phenyl)-2,2-dimethylpropionic acid

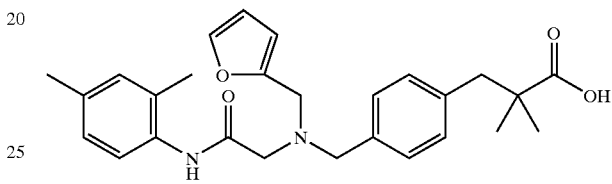

A solution of 192 mg (0.380 mmol) of tert-butyl 3-(4-{[(2-(2,4-dimethylphenyl)-amino-2-oxoethyl)(2-furylmethyl)amino]methyl}phenyl)-2,2-dimethylpropionate (Example 1-1) in 1 ml of dichloromethane is treated with 1 ml of trifluoroacetic acid and stirred at room temperature for 2 h. The mixture is then concentrated under reduced pressure, the residue is taken up in ethyl acetate and the organic phase is washed 2× with water, 1× with 20% strength sodium acetate solution, 1× with water and 1× with sat. NaCl solution, dried over sodium sulphate and freed from the solvent under reduced pressure. Chromatographic purification of the residue on silica gel (dichloromethane→dichloromethane/methanol 20:1) gives 150 mg (88%) of 3-(4-{[(2-(2,4-dimethylphenyl)amino-2-oxoethyl)(2-furylmethyl)amino]methyl}-phenyl)-2,2-dimethylpropionic acid.

$^1$H-NMR (200 MHz, CDCl$_3$): δ=1.16 (s, 6H); 2.26 (s, 3H); 2.28 (s, 3H); 2.87 (s, 2H); 3.30 (s, 2H); 3.71 (s, 2H); 3.74 (s, 2H); 6.26 (d, 1H); 6.32 (dd, 1H); 6.99 (m, 2H); 7.12 (d, 2H); 7.24 (d, 2H); 7.37 (d, 1H); 7.83 (d, 1H); 9.12 (broad s, 1H).

Example 1-10

3-(4-{[(2-(4-Methoxy-2,5-dimethylphenyl)amino-2-oxoethyl)(2-furylmethyl)amino]methyl}phenyl)-2,2-dimethylpropionic acid

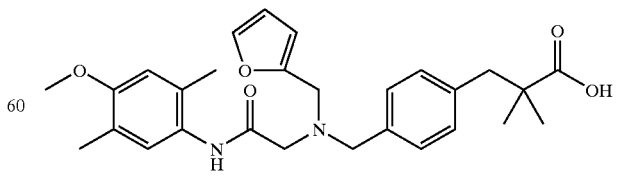

Similarly to the procedure of Example 1-9, 170 mg (0.318 mmol) of tert-butyl 3-(4-{[(2-(4-methoxy-2,5-dimethylphenyl)amino-2-oxoethyl)(2-furylmethyl)amino]

methyl}phenyl)-2,2-dimethylpropionate (Example 1-2) are reacted with 1 ml of trifluoroacetic acid in 1 ml of dichloromethane to give 133 mg (87%) of 3-(4-{[(2-(4-methoxy-2,5-dimethylphenyl)amino-2-oxoethyl)(2-furylmethyl)amino]methyl}phenyl)-2,2-dimethylpropionic acid.

¹H-NMR (200 MHz, DMSO): δ=1.04 (s, 6H); 2.07 (s, 3H); 2.13 (s, 3H); 2.76 (s, 2H); 3.18 (s, 2H); 3.70 (s, 2H); 3.74 (s, 3H); 3.76 (s, 2H); 6.39 (d, 2H); 6.87 (s, 1H); 7.12 (d, 2H); 7.28 (d, 2H); 7.30 (s, 1H); 7.61 (s, 1H); 9.02 (broad s, 1H); 12.18 (broad s, 1H).

Example 1-11

3-(4-{[N-(2-(2,4-Dimethylphenyl)amino-2-oxo)ethyl-N-phenylamino]methyl}phenyl)-2,2-dimethylpropionic acid

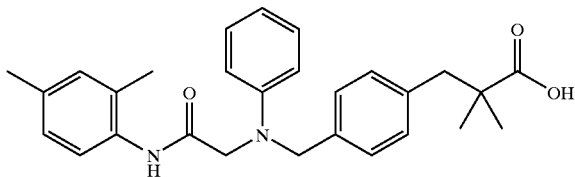

Similarly to the procedure of Example 1-9, 48 mg (0.096 mmol) of tert-butyl 3-(4-{[N-(2-(2,4-dimethylphenyl)amino-2-oxo)ethyl-N-phenylamino]methyl}phenyl)-2,2-dimethylpropionate (Example 1-3) are reacted with 1 ml of trifluoroacetic acid in 2 ml of dichlormethane to give 36 mg (85%) of 3-(4-{[N-(2-(2,4-dimethylphenyl)amino-2-oxo)ethyl-N-phenylamino]methyl}phenyl)-2,2-dimethylpropionic acid.

¹H-NMR (200 MHz, CDCl₃): δ=1.19 (s, 6H); 1.90 (s, 3H); 2.26 (s, 3H); 2.87 (s, 2H); 4.08 (s, 2H); 4.66 (s, 2H); 6.80–6.95 (m, 4H); 6.98 (d, 1H); 7.14 (s, 4H) 7.27 (m, 2H); 7.67 (d, 1H); 8.08 (broad s, 1H).

Example 1-12

3-(4-{[N-(2-(4-Methoxy-2,5-dimethylphenyl)amino-2-oxo)ethyl-N-phenylamino]methyl}phenyl)-2,2-dimethylpropionic acid

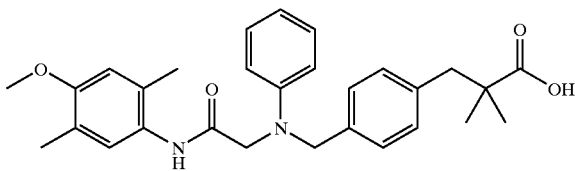

Similarly to the procedure of Example 1-9, 61 mg (0.115 mmol) of tert-butyl 3-(4-{[N-(2-(4-methoxy-2,5-dimethylphenyl)amino-2-oxo)ethyl-N-phenylamino]methyl}phenyl)-2,2-dimethylpropionate (Example 1-4) are reacted with 1 ml of trifluoroacetic acid in 2 ml of dichloromethane to give 46 mg (85%) of 3-(4-{[N-(2-(4-methoxy-2,5-dimethylphenyl)amino-2-oxo)ethyl-N-phenylamino]methyl}phenyl)-2,2-dimethylpropionic acid.

¹H-NMR (200 MHz, CDCl₃): δ=1.19 (s, 6H); 1.94 (s, 3H); 2.15 (s, 3H); 2.86 (s, 2H); 3.77 (s, 3H); 4.08 (s, 2H); 4.66 (s, 2H); 6.56 (s, 1H); 6.83 (dd, 1H); 6.88 (d, 2H); 7.13 (s, 4H); 7.24 (d, 2H); 7.34 (m, 1H); 7.93 (broad s, 1H).

Example 1-13

3-(4-{[N-(2-(2,4-Dimethylphenyl)amino-2-oxo)ethyl-N-(4-methylphenyl)amino]methyl}phenyl)-2,2-dimethylpropionic acid

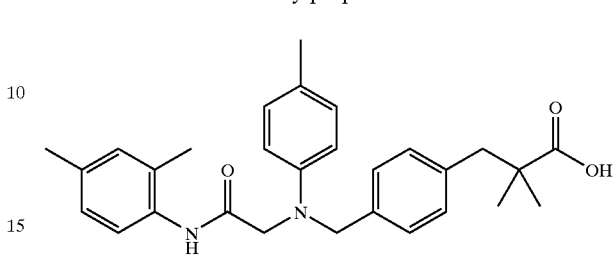

Similarly to the procedure of Example 1-9, 23 mg (0.049 mmol) of tert-butyl 3-(4-{[N-(2-(2,4-dimethylphenyl)amino-2-oxo)ethyl-N-(4-methylphenyl)amino]methyl}phenyl)-2,2-dimethylpropionate (Example 1-5) are reacted with 1 ml of trifluoroacetic acid in 2 ml of dichloromethane to give 20 mg (91%) of 3-(4-{[N-(2-(2,4-dimethylphenyl)amino-2-oxo)ethyl-N-(4-methylphenyl)amino]methyl}phenyl)-20 2,2-dimethylpropionic acid.

¹H-NMR (200 MHz, CDCl₃): δ=1.17 (s, 6H); 1.92 (s, 3H); 2.25 (s, 6H); 2.86 (s, 2H); 4.02 (s, 2H); 4.60 (s, 2H); 6.79 (d, 2H); 6.91 (s, 1H); 6.98 (d, 1H); 7.06 (d, 2H); 7.13 (s, 2H); 7.17 (d, 2H); 7.68 (d, 1H); 8.19 (broad s, 1H).

Example 1-14

3-(4-{[N-(2-(4-Methoxy-2,5-dimethylphenyl)amino-2-oxo)ethyl-N-(4-methylphenyl)amino]methyl}phenyl)-2,2-dimethylpropionic acid

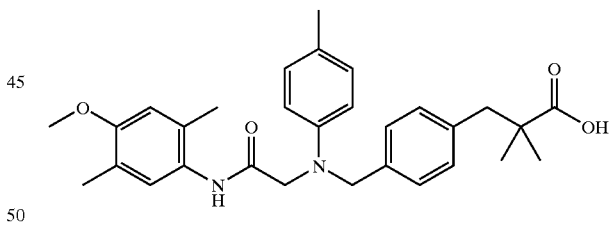

Similarly to the procedure of Example 1-9, 40 mg (0.073 mmol) of tert-butyl 3-(4-{[N-(2-(4-methoxy-2,5-dimethylphenyl)amino-2-oxo)ethyl-N-(4-methylphenyl)-amino]methyl}phenyl)-2,2-dimethylpropionate (Example 1-6) are reacted with 1 ml of trifluoroacetic acid in 2 ml of dichloromethane to give 33 mg (93%) of 3-(4-{[N-(2-(4-methoxy-2,5-dimethylphenyl)amino-2-oxo)ethyl-N-(4-methylphenyl)amino]methyl}phenyl)-2,2-dimethylpropionic acid.

¹H-NMR (200 MHz, CDCl₃): δ=1.18 (s, 6H); 1.96 (s, 3H); 2.15 (s, 3H); 2.26 (s, 3H); 2.86 (s, 2H); 3.76 (s, 3H); 4.03 (s, 2H); 4.61 (s, 2H); 6.57 (s, 1H); 6.80 (dd, 2H); 7.07 (d, 2H); 7.14 (s, 4H); 7.36 (s, 1H); 8.02 (broad s, 1H).

Example 1-15

2-(4-{[(1-{[(2,4-Dimethylphenyl)amino]
carbonyl}propyl)amino]methyl}phenoxy)-2-
methylpropionic acid

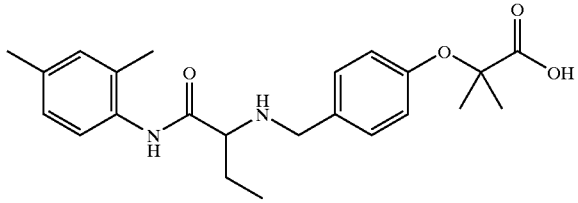

Similarly to the procedure of Example 1-9, 170 mg (0.374 mmol) of tert-butyl 2-(4-{[(1-{[(2,4-dimethylphenyl)amino]carbonyl}propyl)amino]methyl}phenoxy)-2-methylpropionate (Example 1-7) are reacted with 0.72 ml (9.35 mmol) of trifluoroacetic acid in 3 ml of dichloromethane to give 113 mg (72%) of 2-(4-{[(1-{[(2,4-dimethylphenyl)amino]carbonyl}propyl)amino]methyl}phenoxy)-2-methyl-propionic acid.

$^1$H-NMR (300 MHz, CDCl$_3$): δ=1.01 (t, 3H); 1.53 (d, 6H); 1.95 (m, 2H); 2.10 (s, 3H); 2.23 (s, 3H); 3.67 (broad s, 1H); 4.02 (m, 1H); 4.55 (m, 1H); 6.61 (d, 2H); 6.82 (d, 1H); 6.89 (s, 1H); 7.10 (d, 2H); 7.11 (s, 1H); 9.53 (broad s, 1H).

Example 1-16

2-(4-{[(1-{[(4-Methoxy-2,5-dimethylphenyl)amino]
carbonyl}propyl)amino]methyl}phenoxy)-2-
methylpropionic acid

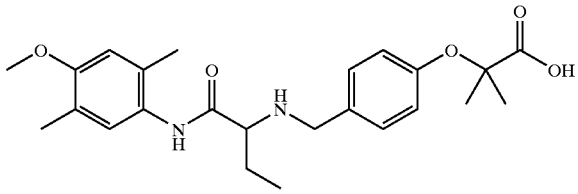

Similarly to the procedure of Example 1-9, 115 mg (0.237 mmol) of tert-butyl 2-(4-{[(1-{[(4-methoxy-2,5-dimethylphenyl)amino]carbonyl}propyl)amino]methyl}phenoxy)-2-methylpropionate (Example 1-8) are reacted with 0.46 ml (5.93 mmol) of trifluoroacetic acid in 3 ml of dichloromethane to give 100 mg (93%) of 2-(4-{[(1-{[(4-methoxy-2,5-dimethylphenyl)amino]carbonyl}propyl)amino]methyl}phenoxy)-2-methylpropionic acid.

$^1$H-NMR (300 MHz, CDCl$_3$): δ=1.05 (t, 3H); 1.55 (d, 6H); 1.97 (m, 2H); 2.10 (s, 6H); 3.75 (s, 3H); 3.78 (m, 1H); 4.08 (m, 2H); 4.50 (m, 2H); 6.50 (s, 1H); 6.64 (d, 2H); 6.94 (s, 1H); 7.14 (d, 2H); 7.65 (s, 1H); 9.38 (broad s, 1H).

STARTING MATERIALS II

Example II-1

1,1-Dimethylethyl 2-[(4-bromophenyl)thio]-2-
methyl-propanoate

4-Bromothiophenol (100 g) and tert-butyl 2-bromoisobutyrate (118 g) are dissolved in 1 l of ethanol and treated with 29 g of KOH. The mixture is stirred under reflux for 2 h and cooled, and the KBr is filtered off. The filtrate is concentrated and the residue is recrystallized from n-hexane. This gives 93.6 g of a colourless solid.

$^1$H-NMR (200 MHz, CDCl$_3$): 1.48 (s, 15H); 7.38 (m, 4H).

Example II-2

1,1-Dimethylethyl 2-[(4-formylphenyl)thio]-2-
methyl-propanoate 1.0 g of 1,1-dimethylethyl 2-[(4-bromophenyl)thio]-2-methyl-propanoate is dissolved in 20 ml of THF and treated with 189 ml (3.02 mmol, 1 eq) of n-butyllithium solution in hexane. Directly afterwards, 0.46 ml of dimethylformamide are added and the mixture is warmed to room temperature and stirred for 1 hour. The reaction is quenched by addition of 1 ml 1 N HCl, the mixture is concentrated and the residue is taken up in ethyl acetate. The mixture is extracted with sat. NaHCO$_3$ solution and with NaCl solution and dried (MgSO$_4$). Chromatographic purification (dichloromethane) gives 550 mg of a pale yellow oil.

LC-MS: Acetonitrile/30% aqueous HCl/water (gradient): R$_t$=4.86 min ([M+H]$^+$=281).

Example II-3

1,1-Dimethylethyl 2-[[4-[[(2-furanylmethyl)amino]
methyl]phenyl]thio]-2-methyl-propanoate 550 mg of 1,1-dimethylethyl 2-[(4-formylphenyl)thio]-2-methyl-propanoate and 381 mg of furfurylamine are initially charged in 100 ml of methanol and treated with 1 ml of glacial acetic acid. The mixture is stirred at room temperature for 15 min, briefly brought to the boil and then, at 0° C., admixed a little at a time with 493 mg of sodium cyanoborohydride. The mixture is stirred overnight at room temperature and then treated with 1 N HCl and stirred for 30 min. The mixture is then made basic using Na$_2$CO$_3$ solution and extracted 2× with ethyl acetate. The organic phase is washed (sat. NaCl solution) and dried (MgSO$_4$). Concentration and chromatographic purification (dichloromethane/ethyl acetate 10+1) gives 430 mg of a colourless oil.

$^1$H-NMR (300 MHz, CDCl$_3$): 1.42 (s, 15H); 3.79 (s, 2H); 3.80 (s, 2H); 6.15 (m, 1H); 6.28 (m, 1H); 7.25–7.45 (m, 5H).

Example II-4

1,1-Dimethylethyl 2-[[(4-[2-[(2-ethoxy-2-oxoethyl)
(2-furanylmethyl)amino]methyl]-phenyl]thio]-2-
methyl-propanoate 5.4 g of 1,1-dimethylethyl 2-[[4-[[(2-furanylmethyl)amino]methyl]phenyl]thio]-2-methyl-propanoate are dissolved in 270 ml of tetrahydrofuran and treated with 2.27 g of triethylamine and 3.74 g of ethyl bromoacetate and 14.85 g of tetra-n-butylammonium iodide. The mixture is stirred at 90° C. for 48 h, cooled and mixed with water and ethyl acetate. The organic phase is separated off and washed twice with sat. NaCl solution. The mixture is dried (MgSO$_4$) and concentrated and the residue is purified chromatographically (cyclohexane/ethyl acetate 5+1), giving 6.4 g of a colourless oil.

$^1$H-NMR (CDCl$_3$, 200 MHz): 1.28 (t, 3H, J=8.7 Hz); 1.40 (s, 9H); 1.42 (s, 6H); 3.32 (s, 2H); 3.78 (s, 2H); 3.84 (s, 2H); 4.15 (q, J=8.7 Hz); 6.17 (m, 1H); 6.30 (m, 1H); 7.25–7.45 (m, 5H).

Example II-5

2-[[4-[2-[(Carboxymethyl)(2-furanylmethyl)amino]
methyl]phenyl]thio]-2-methyl-1,1-dimethylethyl
propanoate 192 mg of 1,1-dimethylethyl 2-[[4-[2-[(2-ethoxy-2-oxoethyl)(2-furanylmethyl)-amino]methyl]phenyl]-thio]-2- methyl-propanoate are initially charged in 5 ml of ethanol and treated with 0.4 ml 1 N NaOH. The mixture is stirred at 80° C. for 1 h. The mixture is checked by TLC ($CH_2Cl_2$/methanol=10+1) and then cooled and concentrated, and the residue is dissolved in a little water. The mixture is acidified using 1 N HCl and extracted three times with ethyl acetate. The combined organic phases are washed 2× with water and 2× with sat. NaCl solution and dried over $MgSO_4$. The mixture is concentrated, applied to silica gel and purified by flash chromatography using $CH_2Cl_2 \rightarrow CH_2Cl_2$/methanol 50+1→25+1. This gives 132 of a colourless oil which solidifies under high vacuum.

$^1$H-NMR (DMSO, 200 MHz): 1.32 (s, 9H); 1.39 (s, 6H); 3.18 (s, 2H); 3.22 (s, 2H); 3.23 (s, 2H); 6.27 (m, 1H); 6.40 (m, 1H); 7.34 (d, 2H, J=9.0 Hz); 7.50 (d, 2H, J=9.0 Hz); 7.59 (m, 1H); 12.38 (broad s, 1H).

Example II-6

1,1-Dimethylethyl 2-[[4-[2-[(2-furanylmethyl) amino]ethyl]phenyl]thio]-2-methyl-propanoate 4.0 g of 1,1-dimethylethyl 2-[[4-(2-aminoethyl)phenyl]thio]-2-methyl-propanoate [(P. J. Brown et al., *J. Med. Chem.* 42, 3785–88 (1999)] are dissolved in 100 ml of methanol and treated with 2.6 g of furfural. 9.3 ml of glacial acetic acid are added and the mixture is boiled briefly (10 min). The mixture is then cooled to 0° C., and 4.25 g of sodium cyanoborohydride are added a little at a time. The mixture is then stirred at room temperature overnight. 1 N HCl is added until the mixture is acidic, and the mixture is stirred for 30 min. The mixture is concentrated slightly and made basic using sat. $NaHCO_3$ solution. The mixture is then extracted twice with ethyl acetate and the extracts are washed (sat. NaCl solution) and dried and concentrated. Chromatographic purification (dichloromethane/methanol 15+1) gives 2.4 g of the title compound as a colourless oil.

$R_f$ (Dichloromethane/methanol 10+1)=0.57.

Example II-7

1,1-Dimethylethyl 2-[[4-[2-[(2-ethoxy-2-oxoethyl)(2-furanylmethyl)amino]ethyl]-phenyl]thio]-2-methyl-propanoate 2.4 g of 1,1-dimethylethyl 2-[[4-[2-[(2-furanylmethyl) amino]ethyl]phenyl]thio]-2-methyl-propanoate, 1.5 g of ethyl bromoacetate, 0.97 g of triethylamine and 7.08 g of tetra-n-butylammonium iodide are dissolved in 100 ml of tetrahydrofuran and heated at reflux overnight. Ethyl acetate and water are added, and the mixture is extracted with water and sat. NaCl solution. Concentration and chromatography (petroleum ether/ethyl acetate 10+1) gives 1.38 g of the title compound.

$^1$H-NMR (DMSO, 200 MHz): 1.18 (t, 3H, J=7.8 Hz); 1.37 (s, 15H); 2.77 (m 4H); 3.32 (s, 2H); 3.81 (s, 2H); 4.06 (q, 2H, J=7.8 Hz); 6.21 (m, 1H); 6.34 (m, 1H); 7.16 (d, 2H, J=9.6 Hz); 7.32 (d, 2H, J=9.6 Hz); 7.58 (m, 1H).

Example II-8

1,1-Dimethylethyl 2-[[4-[2-[(carboxymethyl)(2-furanylmethyl)amino]ethyl]phenyl]-thio]-2-methyl-propanoate 1.0 g of 1,1-dimethylethyl 2-[[4-[2-[(2-ethoxy-2-oxoethyl)(2-furanylmethyl)amino]-ethyl]phenyl]-thio]-2-methyl-propanoate is treated with 6.5 ml of 1 N NaOH in 10 ml of ethanol. The mixture is stirred at 80° C. for 1 h, concentrated, dissolved in water and acidified with 1 N HCl. Three extractions with ethyl acetate and chromatography (dichloromethane/methanol 5+1) gives 744 mg as a colourless oil.

$^1$H-NMR (DMSO, 200 MHz): 1.36 (s, 15H); 2.75 (m, 4H); 3.20 (s, 2H); 3.72 (s, 2H); 6.18 (m, 1H); 6.88 (m, 1H); 7.12 (d, 2H, J=9.5 Hz); 7.32 (d, 2H, J=9.5 Hz); 7.56 (m, 1H).

Example II-9

1,1-Dimethylethyl 2-[[4-[[(2-methoxyethyl)amino] methyl]phenyl]thio]-2-methyl-propanoate 7.9 g of 1,1-dimethylethyl 2-[(4-formylphenyl)thio]-2-methyl-propanoate and 4.23 g of methoxyethylamine are initially charged in 100 ml of methanol and admixed with 19 ml of acetic acid. The mixture is stirred at RT for 15 min, boiled briefly and then, at 0° C., admixed a little at a time with 8.9 g of sodium cyanoborohydride. The mixture is stirred at room temperature overnight and then admixed with 1 N HCl and stirred for 30 min. The mixture is then made basic using sodium carbonate solution and extracted 2× with ethyl acetate. The organic phase is washed with sat. sodium chloride solution and dried over magnesium sulphate. Concentration and chromatographic purification give 5.6 g (58%) of a colourless oil.

$^1$H-NMR (200 MHz, $CDCl_3$): δ=1.38 (s, 6H), 1.42 (s, 9H), 2.45 (m, 3H, $CH_2$+NH), 3.37 (s, 3H), 3.88 (s, 2H), 7.25–7.52 (m, 4H).

Example II-10

1,1-Dimethylethyl 2-[[4-[[(2-(5-methylfuranmethyl))amino]methyl]phenyl]thio]-2-methyl-propanoate 8.0 g 1,1-dimethylethyl 2-[(4-formylphenyl)thio]-2-methyl-propanoate and 6.3 g of 5-methyl-2-furanmethanamine are initially charged in 100 ml of methanol and treated with 16 ml of acetic acid. The mixture is stirred at RT for 15 min, boiled briefly and then, at 0° C., admixed a little at a time with 5.7 g of sodium cyanoborohydride. The mixture is stirred at room temperature overnight and then admixed with 1 N HCl and stirred for 30 min. The mixture is then made basic using sodium carbonate solution and extracted 2× with ethyl acetate. The organic phase is washed with sat. sodium chloride solution and dried over magnesium sulphate. Concentration and chromatographic purification gives 4.8 g (45%) of a colourless oil which tends to decompose and is stored at −25° C.

$^1$H-NMR (200 MHz, $CDCl_3$): δ=1.42 (s, 15H), 1.72 (s, 1H, NH), 2.28 (s, 3H), 3.79 (s, 2H), 3.78 (s, 2H), 5.88 (m, 1H), 6.03 (m, 1H), 7.28 (dd, 2H, J=11 Hz), 7.45 (m, 2H, J=11 Hz).

Example II-11

2-Bromo-N-(2,4-dimethylphenyl)-acetamide 117 g of triethylamine and 140 g of 2,4-dimethylaniline are dissolved in 2 l of methylene chloride, and a solution of 233 g of alpha-bromoacetyl bromide in 400 ml of methylene chloride is added with ice-cooling, at at most 15° C., within 30 min. After a reaction time of 30 min, the precipitate is filtered off with suction, the residue is dissolved in 3 l of methylene chloride and combined with the filtrate and washed twice with 2 l of water and 2 l of sat. sodium chloride solution. The mixture is dried over sodium sulphate, filtered off with suction and concentrated, and the residue is recrystallized from ethanol. This gives 193 g of the title compound.

Example II-12

2-Bromo-N-(2,4-dichlorophenyl)-acetamide

This compound was prepared similarly to Example II-11 from 4.2 g of 2,4-dichloroaniline and 5.76 g of bromoacetyl bromide and 2.89 g of triethylamine in methylene chloride. This gave 5.9 g (80.4%) of the title compound.

$R_f$ (Dichloromethane): 0.38
MS (EI pos.): $M^+$=283.

WORKING EXAMPLES 2

Example 2-1 tert-Butyl 2-[[4-[[[2-[(2,4-dimethylphenyl)amino]-2-oxoethyl](2-furanylmethyl)-amino]-methyl]phenyl]thio]-2-methyl-propanoate Method a)

250 mg of 2-[[4-[2-[(carboxymethyl)(2-furanylmethyl)amino]methyl]-phenyl]thio]-2-methyl-1,1-dimethylethyl propanoate, 89 mg of hydroxybenzotriazole, 249 ml of triethylamine, 82 mg of 2,4-dimethylaniline and 131 mg of N'-(3-dimethylaminopropyl)-N-ethylcarbodiimide hydrochloride are dissolved in 5 ml of dichloromethane. The mixture is stirred at room temperature for 20 h and extracted with 1 N NaOH, 1 N HCl, water and sat. NaCl solution. The combined organic phases are dried (MgSO$_4$) and purified chromatographically (dichloromethane/ethyl acetate 25+1). This gives 200 mg of a viscous oil.

LC-MS: Acetonitrile/30% aqueous HCl/water (gradient): $R_t$=4.87 min ([M+H]$^+$=523).

Method b)

1.5 g of 1,1-dimethylethyl 2-[[4-[[[(2-furanylmethyl)amino]methyl]phenyl]thio]-2-methyl-propanoate (Example II-3) and 1.1 g of 2-bromo-N-(2,4-dimethylphenyl)-acetamide (Example II-9) are dissolved in 20 ml of DMF and treated with 0.4 g of sodium bicarbonate. The mixture is heated at 90° C. overnight, concentrated and purified chromatographically (dichloromethane/ethyl acetate 10:1 and 5:1). This gives 2.1 g of the title compound.

Example 2-2 tert-Butyl 2-[[4-[[[2-[(2,4,6-trimethylphenyl)amino]-2-oxoethyl](2-furanylmethyl)-amino]-methyl]phenyl]thio]-2-methyl-propanoate 250 mg of 2-[[4-[2-[(carboxymethyl)(2-furanylmethyl)amino]methyl]-phenyl]thio]-2-methyl-1,1-dimethylethyl propanoate, 90 mg of hydroxybenzotriazole, 250 ml of triethylamine, 80 mg of 2,4,6-trimethylaniline and 130 mg of N'-(3-dimethylaminopropyl)-N-ethylcarbodiimide hydrochloride are dissolved in 5 ml of dichloromethane. The mixture is stirred at room temperature for 20 h and extracted with 1 N NaOH, 1 N HCl, water and sat. NaCl solution. The combined organic phases are dried (MgSO$_4$) and purified chromatographically (dichloromethane/ethyl acetate 25+1). This gives 210 mg of a viscous oil.

LC-MS: Acetonitrile/30% aqueous HCl/water (gradient): $R_t$=5.32 min ([M+H]$^+$=537).

Example 2-3 tert-Butyl 2-[[4-[[[2-[(2,5-dimethyl4-methoxyphenyl)amino]-2-oxoethyl](2-furanylmethyl)-amino]methyl]phenyl]thio]-2-methyl-propanoate 250 mg of 2-[[4-[2-[(carboxymethyl)(2-furanylmethyl)amino]-ethyl]-phenyl]thio]-2-methyl-1,1-dimethylethyl propanoate, 90 mg of hydroxybenzotriazole, 250 ml of triethylamine, 80 mg of 2,5-dimethyl-4-methoxyaniline and 130 mg of N'-(3-dimethylaminopropyl)-N-ethylcarbodiimide hydrochloride are dissolved in 5 ml of dichloromethane. The mixture is stirred at room temperature for 20 h and extracted with 1 N NaOH, 1 N HCl, water and sat. NaCl solution. The combined organic phases are dried (MgSO$_4$) and purified chromatographically (dichloromethane/ethyl acetate 25+1). This gives 190 mg of a viscous oil.

LC-MS: Acetonitrile/30% aqueous HCl/water (Gradient): $R_t$=4.90 min ([M+H]$^+$=552).

Example 2-4 tert-Butyl 2-[[4-[[[2-[(2-methyl4-methoxyphenyl)amino]-2-oxoethyl](2-furanylmethyl)amino]-methyl]phenyl]thio]-2-methyl-propanoate 250 mg of 2-[[4-[2-[(carboxymethyl)(2-furanylmethyl)amino]-ethyl]-phenyl]thio]-2-methyl-1,1-dimethylethyl propanoate, 90 mg of hydroxybenzotriazole, 250 ml of triethylamine, 80 mg of 2-methyl-4-methoxylaniline and 130 mg of N'-(3-dimethylaminopropyl)-N-ethylcarbodiimide hydrochloride are dissolved in 5 ml of dichloromethane. The mixture is stirred at room temperature for 20 h and extracted with 1 N NaOH, 1 N HCl, water and sat. NaCl solution. The combined organic phases are dried (MgSO$_4$) and purified chromatographically (dichloromethane/ethyl acetate 25+1). This gives 190 mg of a viscous oil.

LC-MS: Acetonitrile/30% aqueous HCl/water (gradient): $R_t$=4.69 min ([M+H]$^+$=538).

Example 2-5

2-[[4-[[[2-[(2,4-Dimethylphenyl)amino]-2-oxoethyl](2-furanylmethyl)amino]-methyl]phenyl]thio]-2-methyl-propanoic acid

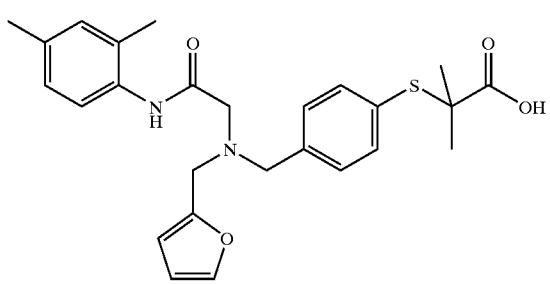

90 mg of tert-butyl 2-[[4-[[[2-[(2,4-dimethylphenyl)amino]-2-oxoethyl](2-furanylmethyl)amino]-methyl]phenyl]thio]-2-methyl-propanoate are dissolved in 5 ml of dichloromethane and reacted with 0.1 ml of trifluoroacetic acid. The mixture is stirred at room temperature for 4 h and then concentrated and purified chromatographically (dichloromethane/methanol 100+1). This gives 80 mg of the title compound as a solid foam.

$R_f$ (Dichloromethane/methanol 10+1)=0.3
$^1$H-NMR (400 MHz, D$_6$-DMSO): δ=1.34 (s, 6H, CH$_3$), 2.16 (s, 3H, CH$_3$), 2.23 (s, 3H, CH$_3$), 3.24 (s, 2H, CH$_2$), 3.76 (s, 2H, CH$_2$), 3.78 (s, 2H, CH$_2$), 6.38–6.40 (m, 2H, 2× furanyl-H), 6.93–6.95 (d, 2H, Ar—H), 7.0 (s, 1H, Ar—H), 7.38–7.51 (m, 4H, Ar—H), 7.60–7.61 (m, 1H, furanyl-H), 9.14 (s, 1H, NH).

MS (ESI pos.): m/z=467 ([M+H]⁺), m/z=489 ([M+Na]⁺)

LC-MS: Acetonitrile/30% aqueous HCl/water (gradient): $R_t$=3.76 min ([M+H]⁺=467).

Example 2-5a

2-[[4-[[[2-[(2,4-Dimethylphenyl)amino]-2-oxoethyl](2-furanylmethyl)amino]-methyl]phenyl]thio]-2-methyl-propanoic acid dicyclohexylammonium salt

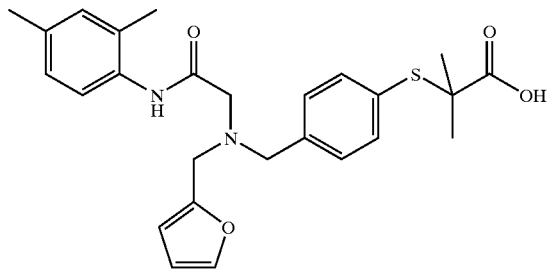

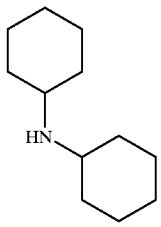

500 mg of 2-[[4-[[[2-[(2,4-dimethylphenyl)amino]-2-oxoethyl](2-furanylmethyl)amino]methyl]phenyl]thio]-2-methyl-propanoic acid (Example 2-5) are dissolved in 500 mg of acetonitrile, and 194 mg of dicyclohexylamine are added. Water is added, some of the acetonitrile is distilled off until the mixture becomes turbid and the mixture is lyophilized. This gives 445 mg of a powder.

LC-MS: Acetonitrile/30% aqueous HCl/water (gradient): $R_t$=3.76 min ([M+H]⁺=467).

Example 2-5b

2-[[4-[[[2-[(2,4-Dimethylphenyl)amino]-2-oxoethyl](2-furanylmethyl)amino]-methyl]phenyl]thio]-2-methyl-propanoic acid hydrochloride

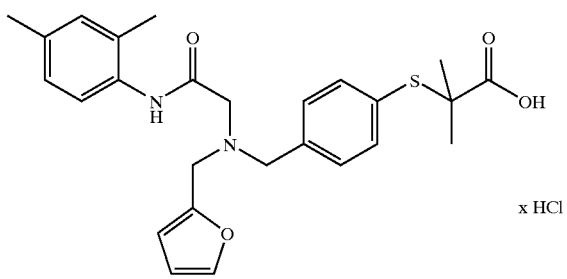

1.20 g of 2-[[4-[[[2-[(2,4-dimethylphenyl)amino]-2-oxoethyl](2-furanylmethyl)amino]-methyl]phenyl]thio]-2-methyl-propanoic acid (Example 2-5) are dissolved in 100 ml of ethyl acetate and admixed with 1 N HCl/diethyl ether until the mixture becomes turbid. The resulting crystals are filtered off with suction and washed with dry ether. This gives 1 g of the title compound.

M.p.: 158° C. (from ethanol/diethyl ether).

Example 2-6

2-[[4-[[[2-[(2,4,6-Trimethylphenyl)amino]-2-oxoethyl](2-furanylmethyl)amino]-methyl]phenyl]thio]-2-methyl-propanoic acid

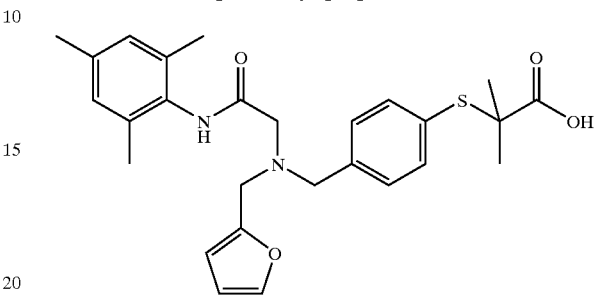

210 mg of tert-butyl 2-[[4-[[[2-[(2,4,6-trimethylphenyl)amino]-2-oxoethyl](2-furanylmethyl)-amino]methyl]phenyl]thio]-2-methyl-propanoate are dissolved in 5 ml of dichloromethane and reacted with 1 ml of trifluoroacetic acid. The mixture is stirred at room temperature for 4 h and then concentrated and purified chromatographically (dichloromethane/ethyl acetate 50+1). This gives 187 mg of the title compound as a solid foam.

¹H-NMR (DMSO, 200 MHz): 1.42 (s, 6H); 2.04 (s, 6H); 2.23 (s, 3H); 3.58 (broad s, 2H); 4.05 (s, 2H); 4.12 (s, 2H); 6.55 (m, 2H); 6.87 (s, 2H); 7.48 (d, 2H, J=9.0 Hz. 7.51 (d, 2H, J=9.0 Hz); 7.72 (m, 1H); 9.40 (broad s, 1H).

Example 2-7

2-[[4-[[[2-[(2,5-Dimethyl-4-methoxyphenyl)amino]-2-oxoethyl](2-furanylmethyl)amino]methyl]phenyl]thio]-2-methyl-propanoic acid

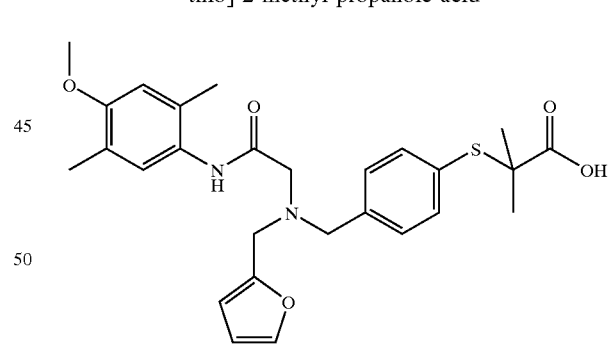

190 mg of tert-butyl 2-[[4-[[[2-[(2,5-dimethyl-4-methoxyphenyl)amino]-2-oxoethyl]-(2-furanyl-methyl)amino]methyl]phenyl]thio]-2-methyl-propanoate are dissolved in 5 ml of dichloromethane and reacted with 1 ml of trifluoroacetic acid. The mixture is stirred at room temperature for 20 h and then concentrated and purified chromatographically (dichloromethane/methanol 50+1). This gives 166 mg of the title compound as a solid foam.

¹H-NMR (DMSO, 200 MHz): 1.39 (s, 6H); 2.08 (s, 3H); 2.11 (s, 3H); 3.7 (s, 3H); 4.00 (broad s, 4H); 6.48 (m, 1H); 6.51 (m, 1H); 6.76 (s, 1H); 7.08 (s, 1H); 7.48 (m, 4H); 7.72 (m, 1H); 9.35, (broad s, 1H); 12.65 (broad s, 1H).

Example 2-8

2-[[4-[[[2-[(2-Methyl4-methoxyphenyl)amino]-2-oxoethyl](2-furanylmethyl)amino]methyl]phenyl)thio]-2-methyl-propanoic acid

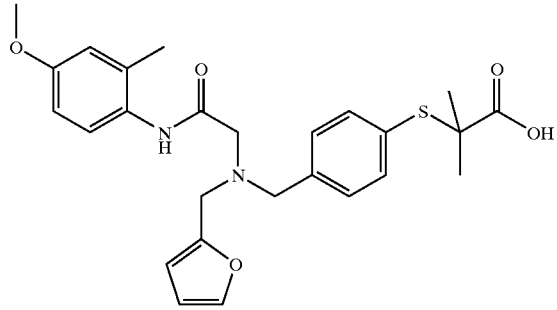

200 mg of tert-butyl 2-[[4-[[[2-[(2-methyl-4-methoxyphenyl)amino]-2-oxoethyl](2-furanyl-methyl)amino]methyl]phenyl]thio]-2-methyl-propanoate are dissolved in 5 ml of dichloromethane and reacted with I ml of trifluoroacetic acid. The mixture is stirred at room temperature for 20 h and then concentrated and purified chromatographically (dichloromethane/methanol 50+1). This gives 174 mg of the title compound as a solid foam.

$^1$H-NMR (DMSO, 200 MHz): 1.38 (s, 6H); 2.12 (s, 3H); 3.7 (s, 3H); 3.80 (broad s, 2H); 4.00 (broad s, 2H); 6.45 (m, 1H); 6.55 (m, 1H); 6.65 (m, 1H); 6.78 (m, 1H); 7.25 (m, 1H); 7.48 (m, 4H); 7.71 (m, 1H); 9.37 (broad s, 1H); 12.65 (broad s, 1H).

Example 2-9 tert-Butyl 2-[[4-[2-[[2-[(2,4-di methylphenyl)amino]-2-oxoethyl](2-furanylmethyl)amino]-ethyl]phenyl]thio]-2-methyl-propanoate 104 mg of 1,1-dimethylethyl 2-[[4-[2-[(carboxymethyl)(2-furanylmethyl)amino]-ethyl]phenyl]thio]-2-methyl-propanoate, 36 mg of hydroxybenzotriazole, 0.1 ml of triethylamine, 29 mg of 2,4-dimethylaniline and 53 mg of N'-(3-dimethylaminopropyl)-N-ethylcarbodiimide hydrochloride are dissolved in 5 ml of dichloromethane. The mixture is stirred at room temperature for 20 h and extracted with 1 N NaOH, 1 N HCl, water and sat. NaCl solution. The combined organic phases are dried (MgSO$_4$) and purified chromatographically (dichloromethane/ethyl acetate 5+1). This gives 190 mg of a viscous oil.

LC-MS: Acetonitrile/30% aqueous HCl/water (gradient): $R_t$=5.3 min ([M+H]$^+$=537).

$^1$H-NMR (CDCl$_3$, 200 MHz): 1.38 (s, 9H); 1.40 (s, 6H); 2.08 (s, 3H); 2.82 (m, 4H); 3.32 (s, 2H); 3.78 (s, 2H); 6.22 (m, 1H); 6.95 (m, 1H); 7.00 (m, 1H); 7.05 (d, 2H, J=10.0 Hz); 7.35 (d, 2H, J=10.0 Hz), including: (m, 1H); 7.79 (m, 1H); 8.95 (broad s, 1H); 12.60 (broad s, 1H).

Example 2-10 tert-Butyl 2-[[4-[2-[[2-[(2,5-dimethyl-4-methoxyphenyl )amino]-2-oxoethyl](2-furanylmethyl)-amino]ethyl]phenyl]thio]-2-methyl-propanoate 98 mg of 1,1-dimethylethyl 2-[[4-[2-[(carboxymethyl)(2-furanylmethyl)amino]ethyl]phenyl]thio]-2-methyl-propanoate, 33 mg of hydroxybenzotriazole, 0.09 ml of triethylamine, 34 mg of 2,5-dimethyl-4-methoxyaniline and 49 mg of N'-(3-dimethylaminopropyl)-N-ethylcarbodiimide hydrochloride are dissolved in 5 ml of dichloromethane. The mixture is stirred at room temperature for 20 h and extracted with 1 N NaOH, 1 N HCl, water and sat. NaCl solution. The combined organic phases are dried (MgSO$_4$) and purified chromatographically (dichloromethane/ethyl acetate 5+1). This gives 48 mg of a viscous oil.

TLC: $R_f$=0.65 (dichloromethane/ethyl acetate=10+1).

Example 2-11

2-[[4-[2-[[2-[(2,4-Dimethylphenyl)amino]-2-oxoethyl](2-furanylmethyl)amino]ethyl]phenyl]thio]-2-methyl-propanoic acid

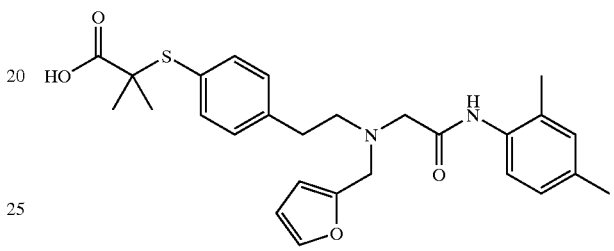

38 mg of tert-butyl 2-[[4-[2-[[2-[(2,4-dimethylphenyl)amino]-2-oxoethyl]2-furanylmethyl)-amino]ethyl]phenyl]thio]-2-methyl-propanoate are dissolved in 5 ml of dichloromethane and treated with 0.27 ml of trifluoroacetic acid. The mixture is stirred at room temperature for 24 h and co-evaporated with toluene, and the residue is chromatographed (dichloromethane/methanol 10+1). This gives 33 mg of a colourless oil.

LC-MS: Acetonitrile/30% aqueous HCl/water (gradient): $R_t$=3.38 min ([M+H]$^+$=481).

Example 2-12

2-[[4-[2-[[2-[(2,5-Dimethyl -4-methoxyphenyl)amino]-2-oxoethyl](2-furanylmethyl)-amino]ethyl]phenyl]thio]-2-methyl-propanoic acid

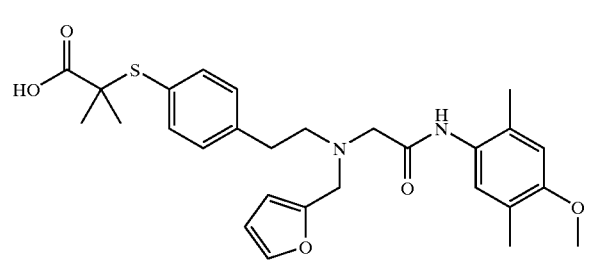

30 mg of tert-butyl 2-[[4-[2-[[2-[(2,5-dimethyl-4-methoxyphenyl)amino]-2-oxoethyl](2-furanyl-methyl)amino]ethyl]phenyl]thio]-2-methyl-propanoate are dissolved in 5 ml of dichloromethane and treated with 0.20 ml of trifluoroacetic acid. The mixture is stirred at room temperature for 24 h and co-evaporated with toluene, and the residue is chromatographed (dichloromethane/methanol 10+1). This gives 27 mg of an oil which turns dark when exposed to the atmosphere.

LC-MS: Acetonitrile/30% aqueous HCl/water (gradient): $R_t$=3.78 min ([M+H]$^+$=511).

¹H-NMR (DMSO, 200 MHz): 1.35 (s, 9H); 2.05 (s, 3H); 2.10 (s, 3H); 2.82 (m, 4H); 3.25 (s, 2H); 3.72 (s, 3H); 3.82 (s, 2H); 6.33 (m, 2H); 6.72 (m, 1H); 7.15 (d, 2H, J=9.8 Hz); 7.24 (d, 2H, J=9.8 Hz), including: (m, 1H); 7.62 (m, 1H); 8.88 (broad s, 1H); 12.55 (broad s, 1H).

The following exemplary compounds were prepared in a similar manner:

Example 2-13

2-Methyl-2-[[4-[[[(5-methyl-2-furanyl)methyl][2-oxo-2-[(2,4-dichlorophenyl)-amino]ethyl]amino]methyl]phenyl]thio]-propanoic acid

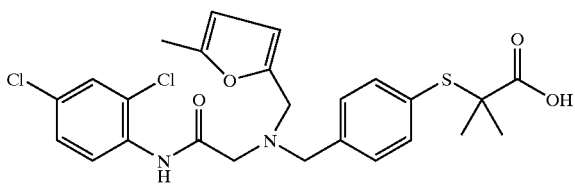

Yield: 343 mg (68%).

¹H-NMR: (200 MHz, CDCl₃): δ=1.50 (s, 6H, 2×CH₃), 2.19 (s, 3H, CH₃), 3.38 (s, 2H, CH₂), 3.78 (s, 2H, CH₂), 3.83 (s, 2H, CH₂), 4.30 (s, br, 1H, COOH), 5.85 (m, 1H, furanyl-H), 6.16 (m, 1H, furanyl-H), 7.18–7.49 (m, 6H, Ar—H), 8.30 (m, 1H, Ar—H), 9.68 (s, 1H, NH).

LC-MS: Acetonitrile/30% aqueous HCl/water (gradient): $R_t$=3.42 min ([M+H]⁺=521)

Example 2-14

2-Methyl-2-[[4-[[[(5-methyl-2-furanyl)methyl][2-oxo-2-[(2,4,6-trichlorophenyl)-amino]ethyl]amino]methyl]phenyl]thio]-propanoic acid

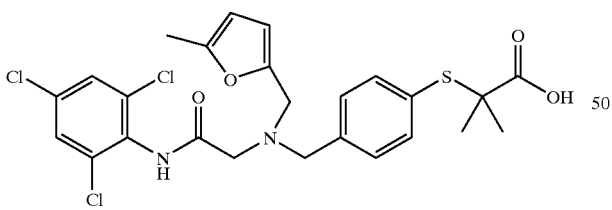

Yield: 90 mg (36%)

¹H-NMR (200 MHz, CDCl₃): δ=1.53 (s, 6H, 2×CH₃), 2.29 (s, 3H, CH₃ ), 3.75 (s, 2H, CH₂), 4.25 (s, 2H, CH₂), 4.28 (s, 2H, CH₂), 5.95 (m, 1H, furanyl-H), 6.49 (m, 1H, furanyl-H), 7.35 (s, 2H, Ar—H), 7.38–7.51 (m, 4H, Ar—H), 9.51 (s, 1H, NH).

LC-MS: Acetonitrile/30% aqueous HCl/water (gradient): $R_t$=3.05 min ([M+H]⁺=555)

Example 2-15

2-Methyl-2-[[4-[[[(5-methyl-2-furanyl)methyl][2-oxo-2-[(2,4,6-trimethylphenyl)amino]ethyl]amino]methyl]phenyl]thio]-propanoic acid

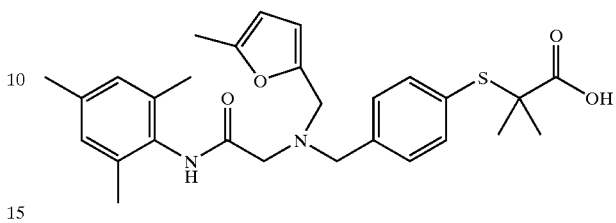

Yield: 46 mg (26%)

LC-MS: Acetonitrile/30% aqueous HCl/water (gradient): $R_t$=4.18 min ([M+H]⁺=494)

Example 2-16

2-Methyl-2-[[4-[[[(5-methyl-2-furanyl)methyl][2-oxo-2-[(2,4-dimethylphenyl)-amino]ethyl]amino]methyl]phenyl]thio]-propanoic acid

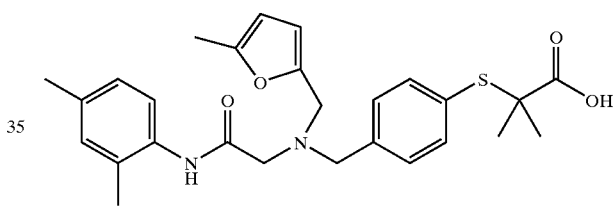

Yield: 183 mg (41%)

LC-MS: Acetonitrile/30% aqueous HCl/water (gradient): $R_t$=2.80 min ([M+H]⁺=481)

Example 2-17

2-Methyl-2-[[4-[[[(5-methyl-2-furanyl)methyl][2-oxo-2-[(2,5-dimethyl-4-methoxyphenyl)amino]ethyl]amino]methyl]phenyl]thio]-propanoic acid

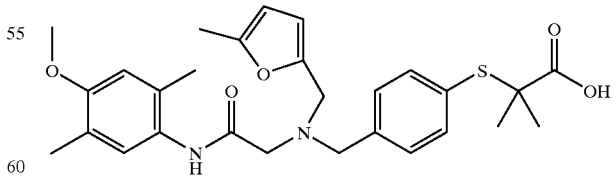

Yield: 149 mg (67%)

LC-MS: Acetonitrile/30% aqueous HCl/water (gradient): $R_t$=4.10 min ([M+H]⁺=511)

Example 2-18

2-Methyl-2-[[4-[[[(5-methyl-2-furanyl)methyl][2-oxo-2-[(4-chloro-2-trifluoromethylphenyl)amino]ethyl]amino]methyl]phenyl]thio]-propanoic acid

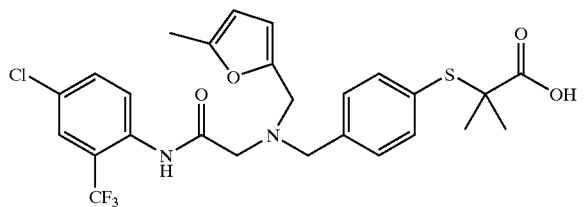

Yield: 63 mg (22%)

LC-MS: Acetonitrile/30% aqueous HCl/water (gradient): $R_t$=3.48 min ([M+H]$^+$=555)

Example 2-19

2-Methyl-2-[[4-[[[(5-methyl-2-furanyl)methyl][2-oxo-2-[(4-methoxy-2-methylphenyl)amino]ethyl]amino]methyl]phenyl]thio]-propanoic acid

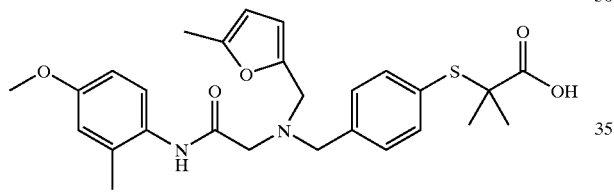

Yield: 24 mg (18%)

LC-MS: Acetonitrile/30% aqueous HCl/water (gradient): $R_t$=2.59 min ([M+H]$^+$=497)

Example 2-20

2-[[4-[[[2-[(2,5-Dimethyl-4-methoxy-phenyl)amino]-2-oxoethyl](2-methoxyethyl)-amino]methyl]phenyl]thio]-2-methyl-propionic acid

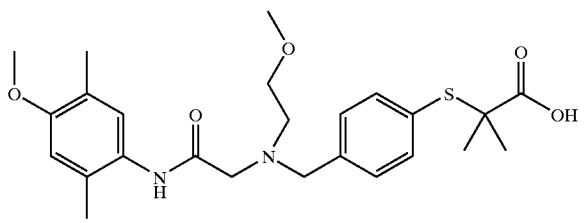

Yield: 60 mg (60%)

LC-MS: Acetonitrile/30% aqueous HCl/water (gradient): $R_t$=2.15 min ([M+H]$^{+=475}$).

Example 2-21

2-Methyl-2-[[4-[[[(5-methyl-2-furanyl)methyl][2-oxo-2-[(2,4-bistrifluoromethylphenyl)amino]ethyl]amino]methyl]phenyl]thio]-propanoic acid Yield: 16 mg (20%)

LC-MS: Acetonitrile/30% aqueous HCl/water (gradient): $R_t$=3.59 min ([M+H]$^+$=589)

Example 2-22

2-Methyl-2-[[4-[[[(5-methyl-2-furanyl)methyl][2-oxo-2-[(2-methyl-4-trifluoromethoxy-5-chlorophenyl)amino]ethyl]amino]methyl]phenyl]thio]-propanoic acid Yield: 89 mg (81%)

LC-MS: Acetonitrile/30% aqueous HCl/water (gradient): $R_t$=3.36 min ([M+H]$^+$=585)

Example 2-23

2-Methyl-2-[[4-[[[(5-methyl-2-furanyl)methyl][2-oxo-2-[(2-trifluoromethyl-4-trifluoromethoxyphenyl)amino]ethyl]amino]methyl]phenyl]thio]-propanoic acid Yield: 22 mg (34%)

LC-MS: Acetonitrile/30% aqueous HCl/water (gradient): $R_t$=3.52 min ([M+H]$^+$=605)

Example 2-24

2-[[4-[[[2-[[2,4-Bis(trifluoromethyl)phenyl]amino]-2-oxoethyl](2-methoxyethyl)-amino]methyl]phenyl]thio]-2-methyl-propanoic acid

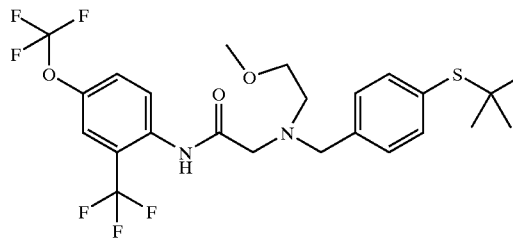

Yield: 26 mg (20%)
LC-MS: Acetonitrile/30% aqueous HCl/water (gradient): $R_t$=3.05 min ([M+H]$^+$=553).

Example 2-25

2-[[4-[[[2-[[2,4-Dichlorophenyl]amino]-2-oxoethyl](2-methoxyethyl)amino]methyl]phenyl]thio]-2-methyl-propanoic acid

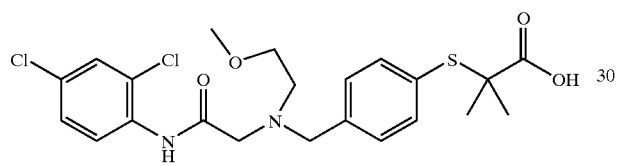

Yield: 61 mg (27%).
$^1$H-NMR (300 MHz, CDCl$_3$): δ=1.38 (s, 6H, 2×CH$_3$), 2.82 (m, 2H, CH$_2$), 3.23 (s, 3H, OMe), 3.32 (s, 2H, CH$_2$), 3.50 (m, 2H, CH$_2$), 3.73 (s, 2H, CH$_2$), 5.28 (s, 1H, COOH), 7.15–7.48 (m, 6H, Ar—H), 8.35 (m, 1H, Ar—H), 9.90 (s, 1H, NH).
LC-MS: Acetonitrile/30% aqueous HCl/water (gradient): $R_t$=2.76 min ([M+H]$^+$=485).

Example 2-26

2-[[4-[[[2-[[2,4-Dimethylphenyl]amino]-2-oxoethyl](2-methoxyethyl)amino]methyl]phenyl]thio]-2-methyl-propanoic acid

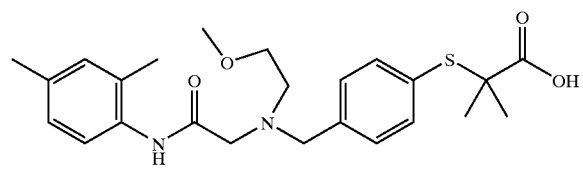

Yield: 50 mg (75%)
$^1$H-NMR (200 MHz, CDCl$_3$): δ=1.50 (s, 6H, 2×CH$_3$), 2.15 (s, 3H, Me), 2.28 (s, 3H, Me), 3.34 (s, 3H, OMe), 3.40 (m, 2H, CH$_2$), 3.68 (m, 2H, CH$_2$), 3.83 (s, 2H, CH$_2$), 4.32 (s, 2H, CH$_2$), 5.40 (s, 1H, COOH), 7.00 (m, 2H, Ar—H), 7.32–7.52 (m, 7H, Ar—H), 9.00 (s, 1H, NH).
LC-MS: Acetonitrile/30% aqueous HCl/water (gradient): $R_t$=2.22 min ([M+H]$^+$=445).

Example 2-27

2-Methyl-2-[[4-[[[(2-thiophenyl)methyl][2-oxo-2-[(2-methyl-4-trifluoromethoxy-5-chlorophenyl)amino]ethyl]amino]methyl]phenyl]thio]-propanoic acid

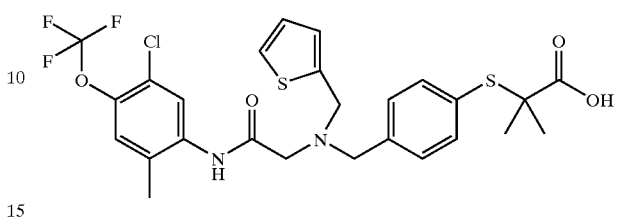

Yield: 200 mg (99%)
$^1$H-NMR (300 MHz, CDCl$_3$): δ=1.50 (s, 6H, 2×CH$_3$), 2.20 (s, 3H, Me), 3.61 (s, 2H, CH$_2$), 4.20 (s, 2H, CH$_2$), 4.48 (s, 2H, CH$_2$), 5.60 (s, 1H, COOH), 7.00 (m, 2H, Ar—H), 7.02–7.17 (m, 3H, Ar—H and thienyl-H), 7.36 (m, 3H, Ar—H), 7.50 (m, 2H, Ar—H), 8.00 (s, 1H, Ar H), 8.88 (s, 1H, NH).
LC-MS: Acetonitrile/30% aqueous HCl/water (gradient): $R_t$=3.40 min ([M+H]$^{30}$=587).

Example 2-28

2-Methyl-2-[[4-[[[(2-thiophenyl)methyl][2-oxo-2-[(2-trifluoromethyl-4-trifluoromethoxy-phenyl)amino]ethyl]amino]methyl]phenyl]thio]-propanoic acid

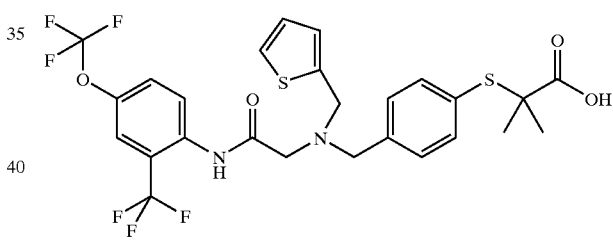

Yield: 80 mg (98%)
LC-MS: Acetonitrile/30% aqueous HCl/water (gradient): $R_t$=3.56 min ([M+H]$^+$=606).

Example 2-29

2-Methyl-2-[[4-[[[(2-thiophenyl)methyl][2-oxo-2-[(2-methyl-4-methoxy-phenyl)-amino]ethyl]amino]methyl]phenyl]thio]-propanoic acid

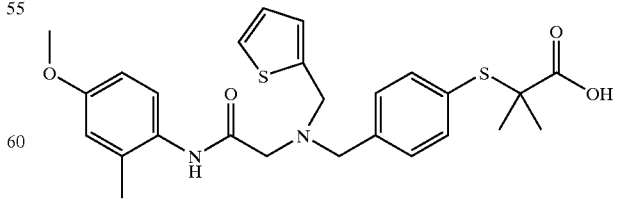

Yield: 83 mg (83%)
LC-MS: Acetonitrile/30% aqueous HCl/water (gradient): $R_t$=2.74 min ([M+H]$^+$=498).

Example 2-30

2-Methyl-2-[[4-[[[(2-furanyl)methyl][2-oxo-2-[(2,4-dimethoxyphenyl)amino]ethyl]amino]methyl]phenyl]thio]-propanoic acid

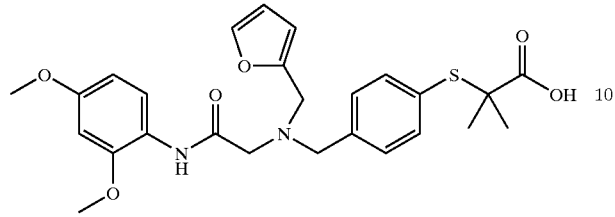

Yield: 75 mg (60%)

LC-MS: Acetonitrile/30% aqueous HCl/water (gradient): $R_t$ 4.19 min ([M+H]$^+$=499).

Example 2-31

2-[[4-[[[2-[(2-Methyl-4-methoxyphenyl)amino]-2-oxoethyl](2-methoxyethyl)amino]methyl]phenyl]thio]-2-methyl-propanoic acid

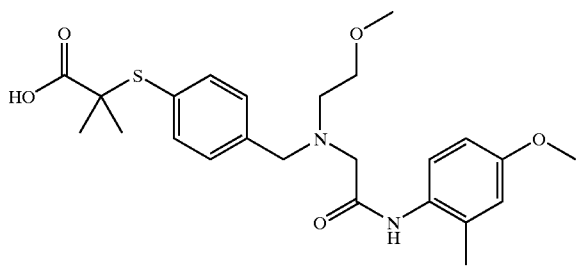

Yield: 65% of theory $^1$H-NMR (300 MHz, CDCl$_3$): δ=1.51 (s, 6H); 2.18 (s, 3H); 3.34 (s, 3H); 3.37–3.45 (m, 2H); 3.65–3.75 (m, 2H); 3.77 (s, 3H); 3.89 (s, 2H); 4.34 (s, 2H); 6.67–6.78 (m, 2H); 7.35–7.44 (m, 3H); 7.52 (d, 2H); 9.05 (s, 1H).

Example 2-32

2-[[4-[[[2-[(2,4,6-Trimethylphenyl)amino]-2-oxoethyl](2-methoxyethyl)amino]methyl]phenyl]thio]-2-methyl-propanoic acid

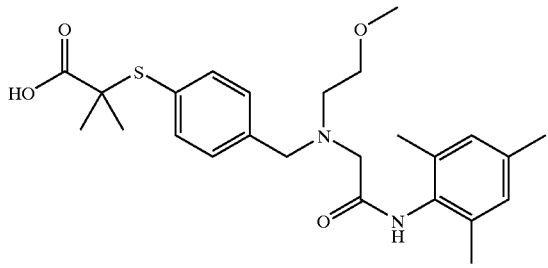

Yield: 89% of theory $^1$H-NMR (300 MHz, CDCl$_3$): δ=1.51 (s, 6H); 2.12 (s, 6H); 2.25 (s, 3H); 3.35 (s, 3H); 3.38–3.54 (m, 2H); 3.65–3.77 (m, 2H); 3.85–3.94 (m, 2H); 4.30–4.45 (m, 2H); 6.87 (s, 2H); 7.39 (d, 2H); 7.53 (d, 2H); 8.82 (br s, 1H).

STARTING MATERIALS III

Example III-1 tert-Butyl (4-formylphenoxy)acetate

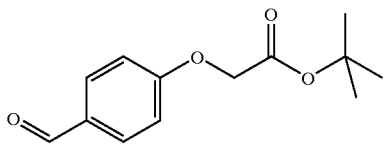

At room temperature, 31.60 g (281.48 mmol) of potassium tert-butoxide and 52.70 g (270.22 mmol) of tert-butyl bromoacetate are added to a solution of 27.50 g (225.18 mmol) of 4-hydroxybenzaldehyde in 200 ml of dioxane, and the mixture is heated at the boil overnight. 1 l of water is added, and the mixture is then extracted with diethyl ether, washed with 1 N sodium hydroxide solution, water and saturated sodium chloride solution and dried over magnesium sulphate, and the solvent is distilled off. Flash chromatography on silica gel (cyclohexane→cyclohexane/ethyl acetate 20:1→10:1→5:1) gives, after recrystallization from pentane, the target compound.

Yield: 31%

Melting point: 58–60° C.

Example III-2 tert-Butyl 2-(4-formylphenoxy)-2-methylpropanoate

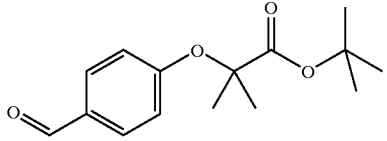

24.42 g (200 mmol) of 4-hydroxybenzaldehyde are dissolved in 250 ml of N,N-dimethylformamide and treated with 27.64 g (200 mmol) of potassium carbonate. At 100° C., 53.55 g (240 mmol) of tert-butyl α-bromoisobutyrate are added dropwise. The mixture is stirred for another hour, a further 200 mmol of potassium carbonate and 240 mmol of tert-butyl (α-bromoisobutyrate are added and, after 4 hours at 100° C., 1 l of water is added. Following extraction with diethyl ether, washing with 1 N aqeuous sodium hydroxide solution and saturated sodium chloride solution and drying over magnesium sulphate, the solvent is distilled off and the residue is purified by flash chromatography on silica gel (cyclohexane→cyclohexane/ethyl acetate 20:1→10:1→5:1) and dried under reduced pressure. The target compound is obtained in the form of colourless crystals in a yield of 42%.

$^1$H-NMR (200 MHz, CDCl$_3$): δ=1.40 (s, 9H), 1.62 (s, 6H), 6.91 (d, 2H), 7.79 (d, 2H), 9.88 (s, 1H).

MS (ESI): 265 [M+H]$^+$.

The following compounds are obtained similarly to the procedure of Example III-2:

Example III-3

Ethyl 2-(4-formylphenoxy)-2-methylbutanoate

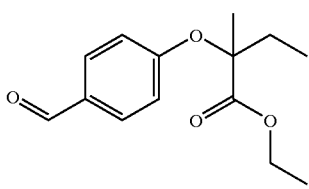

Yield: 11.71%

$^1$H-NMR (200 MHz, CDCl$_3$): δ=1.00 (t, 3H), 1.22 (t, 3H), 1.61 (s, 3H), 1.90–2.20 (m, 2H), 4.24 (q, 2H), 6.90 (d, 2H), 7.80 (d, 2H), 9.85 (s, 1H).

MS (ESI): 251 [M+H]$^+$, 273 [M+Na]$^+$.

Example III-4 tert-Butyl 2-[(3-bromophenyl)sulphanyl]-2-methylpropanoat

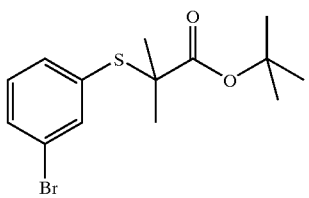

Yield: 87%

$^1$H-NMR (200 MHz, CDCl$_3$): δ=1.43 (s, 9H), 1.45 (s, 6H), 7.14–7.28 (m, 1H), 7.39–7.53 (m, 2H), 7.67 (t, 1H).

MS (DCI/NH$_3$): 348 [M+N$_4$$^+$].

Example III-5 tert-Butyl 2-(3-formylphenoxy)-2-methylpropanoate

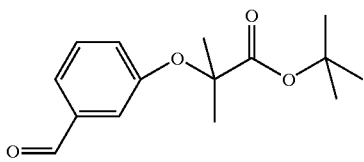

Yield: 35%

$^1$H-NMR (300 MHz, CDCl$_3$): δ=1.44 (s, 9H), 1.61 (s, 6H), 7.14 (dd, 1H), 7.31–7.35 (m, 1H), 7.41 (t, 1H), 7.45–7.52 (m, 1H).

MS (DCI/NH$_3$): 282 [M+NH$_4$$^+$].

Example III-6 tert-Butyl 2-(3-bromophenoxy)-2-methylpropanoate

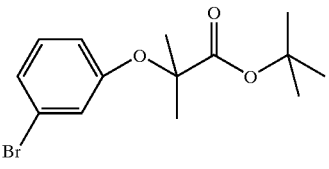

Yield: 21%

$^1$H-NMR (300 MHz, CDCl$_3$): δ=1.44 (s, 9H), 1.56 (s, 6H), 6.74–6.83 (m, 1H) 7.00–7.04 (m, 1H), 7.06–7.11 (m, 2H).

MS (DCI/NH$_3$): 332 [M+NH$_4$$^+$].

Example III-7 tert-Butyl 2-[4-(1,3-dioxo-1,3-dihydro-2H-isoindol-2-yl)phenoxy]-2-methyl-propanoate

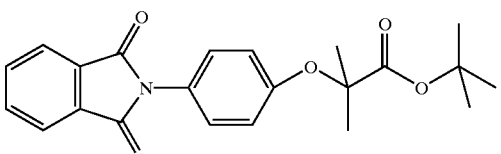

Yield: 24%
Melting point: 142–143° C.

Example III-8 tert-Butyl 2-[(3-formylphenyl)sulphanyl]-2-methylpropanoate

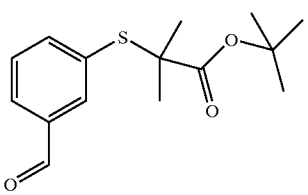

At −78° C., 30.00 g (90.56 mmol) of the compound from Example III-4 are dissolved in tetrahydrofuran and treated with 36.2 ml of a 2.5 M n-butyllithium solution in hexane. 13.94 ml (181.12 mmol) of N,N-dimethylformamide are then added. After 30 min, the mixture is warmed to room temperature and stirred for 1 hour. 30 ml of 1 N hydrochloric acid are added, the solvent is distilled off, the residue is extracted with ethyl acetate and the extract is washed with saturated sodium bicarbonate solution and sodium chloride solution and then dried over magnesium sulphate. Following flash chromatography on silica gel (dichloromethane), the target compound is purified by NP-HPLC (cyclohexane/ethyl acetate) and obtained in a yield of 10%.

$^1$H-NMR (300 MHz, CDCl$_3$): δ=1.43 (s, 9H), 1.46 (s, 6H), 7.50 (t, 1H), 7.77–7.80 (m, 1H), 7.87 (d, 1H), 7.98–8.05 (m, 1H), 10.00 (s, 1H).

MS (DCI/NH$_3$): 298 [M+NH$_4$$^+$].

Example III-9 tert-Butyl 2-{3-[2-(1,3-dioxo-1,3-dihydro-2H-isoindol-2-yl)ethenyl]phenoxy}-2-methyl-propanoate

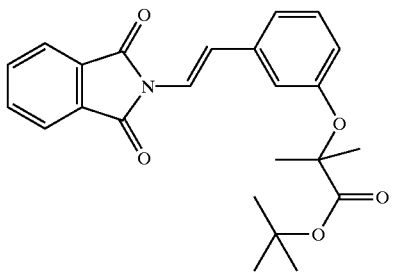

In an autoclave, 14.93 g (47.37 mmol) of the compound from Example III-6, 10.25 g (59.21 mmol) of vinylphthalimide, 0.39 g (1.27 mmol) of tris-o-tolylphosphine, 0.07 g (0.32 mmol) [lacuna] and 21.78 g (215.23 mmol) of triethylamine are heated at 130° C. Water/methanol is added, and the precipitate is then filtered off with suction and recrystallized from cyclohexane/ethyl acetate.

Yield: 66%.

$^1$H-NMR (200 MHz, CDCl$_3$): δ=1.40 (s, 9H), 1.50 (s, 6H), 6.73 (dd, 1H), 6.86–6.93 (m, 1H), 7.16 (t, 1H), 7.21–7.34 (m, 2H), 7.43 (d, 1H), 7.80–8.00 (m, 4H).

MS (DCI/NH$_3$): 425 [M+NH$_4^+$].

Example III-10 tert-Butyl 2-{3-[2-(1,3-dioxo-1,3-dihydro-2H-isoindol-2-yl)ethyl]phenoxy}-2-methyl-propanoate

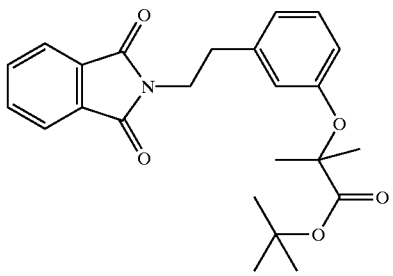

15.00 g (36.81 mmol) of the compound from Example III-9 are dissolved in 200 ml of tetrahydrofuran and stirred overnight in a hydrogen atmosphere under atmospheric pressure in the presence of a suspension of 2.00 g (2.16 mmol) of Wilkinson's catalyst in 40 ml of ethanol. Two flash chromatographies on silica gel (cyclohexane/dichloromethane 10:1→cyclohexane/ethyl acetate 10:1→5:1 and cyclohexane→cyclohexane/dichloromethane→dichloromethane) give the title compound in a yield of 64%.

$^1$H-NMR (200 MHz, CDCl$_3$): δ=1.45 (s, 9H), 1.52 (s, 6H), 2.85–3.00 (m, 2H), 3.82–3.95 (m, 2H), 6.65–6.80 (m, 2H), 6.88 (d, 1H), 7.15 (t, 1H), 7.62–7.76 (m, 2H), 7.77–7.89 (m, 2H).

MS (ESI): 432 [M+Na$^+$], 841 [2M+Na$^+$].

Example III-11 tert-Butyl 2-(4-aminophenoxy)-2-methylpropanoate

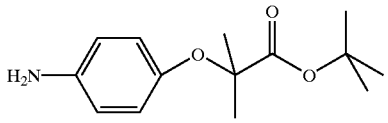

18.88 g (49.50 mmol) of the compound from Example III-7 are dissolved in 25 ml of ethanol and, with 12.04 ml (247.49 mmol) of hydrazine hydrate, heated at the boil for 2 h and then stirred at room temperature for 12 hours. The precipitate is separated off and washed with ethanol and the filtrate is concentrated and then diluted with 1 l of diethyl ether. This solution is washed with 1 N sodium hydroxide solution and saturated sodium chloride solution and dried over magnesium sulphate. The solvent is removed, giving the title compound in a yield of 87%.

Melting point: 87–88° C.

The following compound is obtained similarly to the procedure of Example III-11:

Example III-12 tert-Butyl 2-[3-(2-aminoethyl)phenoxy]-2-methylpropanoate

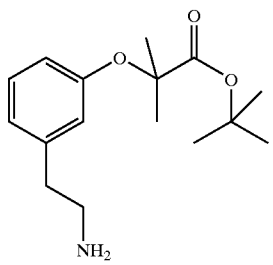

Yield: 70%

$^1$H-NMR (200 MHz, CDCl$_3$): δ=1.31 (broad s, 2H), 1.44 (s, 9H), 1.56 (s, 6H), 2.69 (t, 2H), 2.94 (t, 2H), 6.64–6.75 (m, 2H), 6.81 (d, 1H), 7.15 (t, 1H).

MS (EI): 279 [M$^+$].

Example III-13 tert-Butyl 2-(4-{[(2-furylmethyl)amino]methyl}phenoxy)-2-methylpropanoate

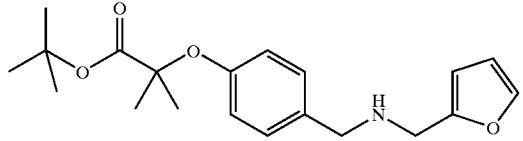

20.00 g (75.67 mmol) of the compound from Example III-2 and 7.35 g (75.67 mmol) of 2-furfurylamine are stirred at room temperature with 24.06 g (113.50 mmol) of sodium triacetoxyborohydride in 350 ml of 1,2-dichloroethane for 5 hours. Saturated sodium bicarbonate solution and ethyl acetate are added to the reaction mixture. The organic phase is dried over magnesium sulphate and the solvent is distilled off, and the residue is then purified by flash chromatography on silica gel (cyclohexane→cyclohexane/ethyl acetate 10:1→2:1). The target compound is obtained in a yield of 72%.

¹H-NMR (200 MHz, CDCl₃): δ=1.61 (broad s, 1H), 1.44 (s, 9H), 1.55 (s, 6H), 3.71 (s, 2H), 3.77 (s, 2H), 6.17 (d, 1H), 6.26–6.36 (m, 2H), 6.70–6.88 (m, 2H), 7.18 (d, 2H), 7.32–7.40 (m, 1H).

MS (ESI): 346 [M+H]⁺.

Example III-14 tert-Butyl 2-{4-[(2-furylmethyl)amino]phenoxy}-2-methylpropanoate

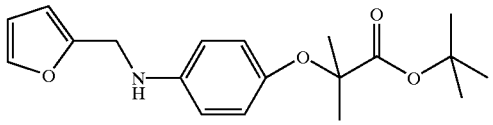

4.79 g (19.06 mmol) of the compound from Example III-11 and 1.83 g (19.06 mmol) of furfural are dissolved in 80 ml of 1,2-dichloroethane and, in the presence of 6.06 g (28.59 mmol) of sodium triacetoxyborohydride, stirred at room temperature for 5 hours. Saturated sodium bicarbonate solution and ethyl acetate are added to the reaction solution. The organic phase is dried over magnesium sulphate and the solvent is distilled off, and the residue is then purified by flash chromatography on silica gel (cyclohexane→cyclohexane/ethyl acetate 10:1→2:1) and by NP-HPLC (cyclohexane/ethyl acetate 10:1). The target compound is obtained in a yield of 79%.

¹H-NMR (200 MHz, CDCl₃): δ=1.46 (s, 9H), 1.48 (s, 6H), 3.80 (broad s, 1H), 4.26 (s, 2H), 6.21 (d, 1H), 6.25–6.35 (m, 1H), 6.50–6.61 (m, 2H), 6.72–6.85 (m, 2H), 7.30–7.39 (m, 1H).

MS (DCI/NH₃): 332 [M+H⁺], 349 [M+NH₄⁺].

Example III-15 tert-Butyl 2-[4-[[(2-ethoxy-2-oxoethyl)(2-furanylmethyl)amino]methyl]phenoxy]-2-methyl-propanoate

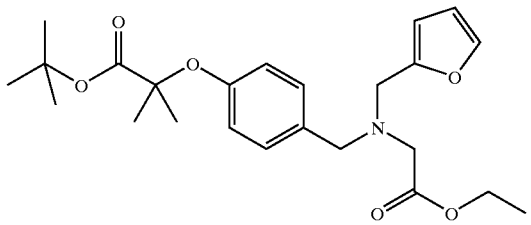

18.14 g (52.50 mmol) of the compound from Example III-13, 11 ml of triethylamine and 1.10 g (2.97 mmol) of tetra-n-butylammonium iodide are initially charged in 200 ml of tetrahydrofuran and treated with 8.77 ml (78.75 mmol) of ethyl bromoacetate, and the mixture is stirred at room temperature for 1 hour and at 60° C. for 2 hours. Water and ethyl acetate are then added to the mixture and the mixture is washed with saturated sodium chloride solution and dried over magnesium sulphate, and, after removal of the solvent, the residue is purified by flash chromatography on silica gel (cyclohexane/dichloromethane 4:1→cyclohexane/ethyl acetate 10:1→5:1). The yield of target compound is quantitative.

¹H-NMR (300 MHz, CDCl₃): δ=1.26 (t, 3H), 1.43 (s, 9H), 1.55 (s, 6H), 3.30 (s, 2H), 3.71 (s, 2H), 3.83 (s, 2H), 4.15 (q, 2H), 6.19 (d, 1H), 6.28–6.34 (m, 1H), 6.77–6.85 (m, 2H), 7.22 (d, 2H), 7.35–7.41 (m, 1H).

MS (ESI): 432 [M+H]⁺.

Example III-16 tert-Butyl 2-[4-[[(carboxymethyl)(2-furanylmethyl)amino]methyl]phenoxy]-2-methyl-propanoate

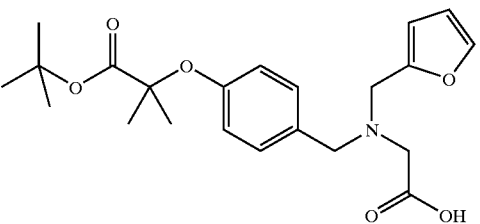

22.01 g (51.00 mmol) of the compound from Example III-15 are stirred at 80° C. in 785 ml of ethanol in the presence of 6.12 g (153.00 mmol) of sodium hydroxide for 1 hour. The solvent is distilled off and water is added, and the mixture is then acidified using 1 N hydrochloric acid and extracted with ethyl acetate. The extract is then washed with water and saturated sodium chloride solution and dried over magnesium sulphate. The amount of solvent is reduced and the product is then filtered off with suction and dried, giving the target compound in a yield of 74%.

Melting point: 152–155° C.

Example III-17

2-Bromo-N-[4-isopropyl-2-(trifluoromethyl)phenyl] acetamide

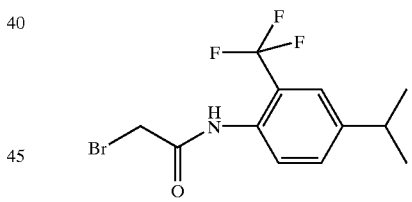

50 g (246.06 mmol) of 4-isopropyl-2-(trifluoromethyl) aniline and 27.39 g (270.66 mmol) of triethylamine are initially charged in 1000 ml of dichloromethane.

At 0°–5° C., 54.63 g (270.66 mmol) of bromoacetyl bromide, dissolved in 200 ml of dichloromethane, are added dropwise. The mixture is stirred at room temperature for 20 hours. The reaction mixture is then extracted successively with water, 1 N hydrochloric acid, water, saturated sodium bicarbonate solution and water. The organic phase is dried over sodium sulphate and the solvent is removed under reduced pressure. The residue is purified chromatographically. The product is recrystallized from cyclohexane/n-pentane, filtered off with suction and dried under reduced pressure at 40° C. for 20 hours. This gives 32.45 g (41% of theory) of the title compound.

¹H-NMR (300 MHz, CDCl₃): δ=1.25 (d, 6H); 2.95 (sept., 1H); 4.05 (s, 2H); 7.45 (d, 1H); 7.49 (s, 1H); 8.02 (d, 1H); 8.50 (br s, 1H).

Example III-18

2-Bromo-N-(4-tert-butyl-2-methylphenyl)acetamide

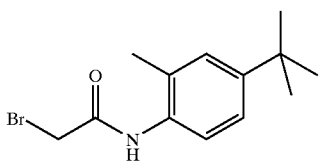

5.5 g (33.69 mmol) of 4-tert-butyl-2-methylaniline and 3.75 g (37.06 mmol) of triethylamine are initially charged in 150 ml of dichloromethane. At 0°–5° C., 7.48 g (37.06 mmol) of bromoacetyl bromide, dissolved in 90 ml of dichloromethane, are added dropwise, and a light-brown precipitate is formed. The mixture is stirred at room temperature overnight. 150 ml of ethyl acetate are then added to the reaction mixture, which is extracted successively with water, 1 N hydrochloric acid, water, saturated sodium bicarbonate soluton and water. The organic phase is dried over magnesium sulphate and freed from the solvent under reduced pressure. The residue is purified chromatographically. The product is recrystallized from ethyl acetate and n-pentane, filtered off with suction and dried under reduced pressure at 40° C. This gives 6.53 g (68% of theory) of the title compound.

$^1$H-NMR (400 MHz, CDCl$_3$): δ=1.3 (s, 9H); 2.3 (s, 3H); 4.06 (s, 2H); 7.20–7.23 (m, 1H); 7.25 (d, 1H); 7.7 (d, 1H); 8.05 (br s, 1H).

Example III-19

2-Bromo-N-(4-cyclohexyl-2-methylphenyl) acetamide

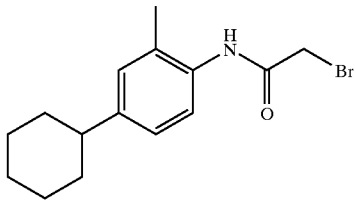

Yield: 41.0% of theory $^1$H-NMR (200 MHz, CDCl$_3$): δ=1.20–1.50 (m, 5H); 1.65–1.95 (m, 5H); 2.28 (s, 3H); 2.35–2.55 (m, 1H); 4.07 (s, 2H); 7.00–7.13 (m, 2H); 7.69 (d, 1H); 8.05 (br s, 1H).

Example III-20

2-Bromo-N-(5,6,7,8-tetrahydro-1-naphthalenyl) acetamide

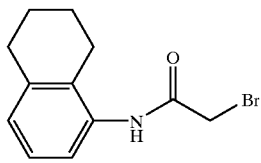

Yield: 95.6% of theory $^1$H-NMR (200 MHz, CDCl$_3$): δ=1.70–1.90 (m, 4H); 2.55–2.70 (m, 2H); 2.75–2.85 (m, 2H); 4.08 (s, 2H); 6.95 (d, 1H); 7.14 (t, 1H); 7.69 (d, 1H); 8.09 (br s, 1H).

Example III-21

2-Bromo-N-[4-(1-naphthyloxy)-2-(trifluoromethyl) phenyl]acetamide

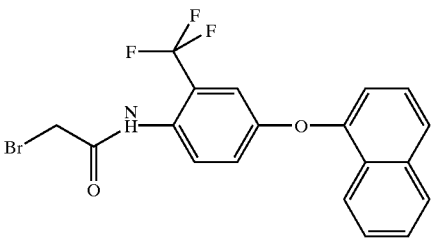

Yield: 80.5% of theory $^1$H-NMR (200 MHz, CDCl$_3$): δ=4.08 (s, 2H); 7.01 (d, 1H); 7.18 (dd, 1H); 7.30–7.62 (m, 4H); 7.70 (d, 1H); 7.85–8.17 (m, 3H); 8.47 (br s, 1H).

Example III-22

2-Bromo-N-[5-chloro-2-(2-naphthyloxy)phenyl] acetamide

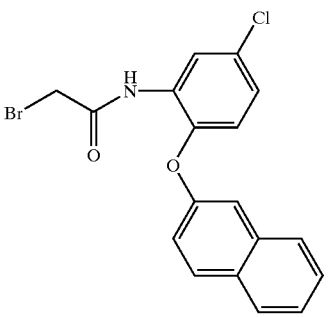

Yield: 77.9% of theory $^1$H-NMR (200 MHz, CDCl$_3$): δ=3.99 (s, 2H); 6.88 (d, 1H); 7.06 (dd, 1H); 7.21–7.36 (m, 2H); 7.38–7.57 (m, 2H); 7.68–7.79 (m, 1H); 7.80–7.95 (m, 2H); 8.51 (d, 1H); 8.85 (br s, 1H).

Example III-23

N-[2,4-Bis(trifluoromethyl)phenyl]-2-bromoacetamide

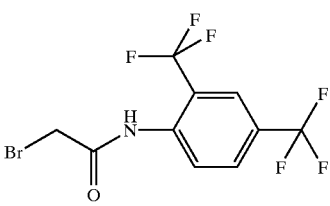

Yield: 28% of theory $^1$H-NMR (200 MHz, CDCl$_3$): δ=4.10 (s, 2H); 7.80–7.91 (m, 2H); 8.50 (d, 1H); 8.80 (br s, 1H).

Example III-24

2-Bromo-N-(2-ethoxy-1-naphthyl)acetamide

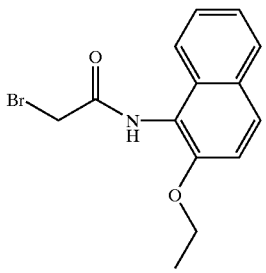

Yield: 24% of theory $^1$H-NMR (300 MHz, CDCl$_3$): δ=1.46 (t, 3H); 4.10–4.30 (m, 4H); 7.26–7.30 (d, 1H); 7.36 (t, 1H); 7.50 (t, 1H); 7.70–7.87 (m, 3H); 8.07 (br s, 1H).

Example III-25

2-Bromo-N-{5-[(ethylsulphonyl)methyl]-1-naphthyl}acetamide

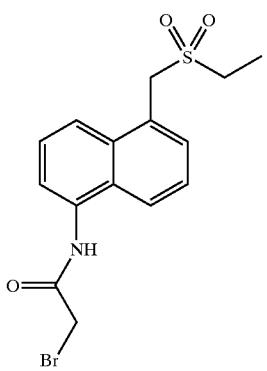

Yield: 16% of theory $^1$H-NMR (200 MHz, CDCl$_3$): δ=1.37 (t, 3H); 1.54 (s, 1H); 2.91 (q, 2H); 4.20 (s, 2H); 4.72 (s, 2H); 7.53–7.70 (m, 3H); 7.90–8.11 (m, 3H); 8.65 (br s, 1H).

Example III-26

2-Bromo-N-[5-chloro-2-methyl-4-(trifluoromethoxy)phenyl]acetamide

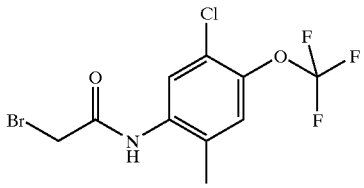

Yield: 84.0% of theory $^1$H-NMR (200 MHz, CDCl$_3$): δ=2.35 (s, 3H); 4.08 (s, 2H); 7.18 (s, 1H); 8.05–8.20 (m, 2H).

Example III-27

4-Methyl-1,3-oxazole-5-carbaldehyde oxime

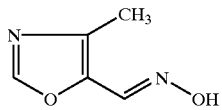

0.50 g (4.50 mmol) of 4-methyl-1,3-oxazole-5-carbaldehyde [prepared from the corresponding alcohol (Chem. Ber. 1961, 1248) by Swern oxidation (Tetrahedron 34, 1651 (1978))] is initially charged in 3 ml of water and treated with 0.66 g (9.45 mmol) of hydroxylamine hydrochloride in 2 ml of water. 0.68 g (4.95 mmol) of potassium carbonate is then added. After 2 h, the mixture is filtered off with suction and the product is washed with water and dried at room temperature. The yield is 0.41 g (72.2% of theory).

$^1$H-NMR (200 MHz, DMSO): δ=2.21 (s, 3H); 8.20 (s, 1H); 8.33 (s, 1H); 11.48 (s, 1H).

Example III-28

(4-Methyl-1,3-oxazol-5-yl)methylamine

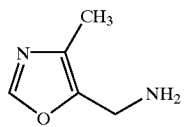

4.00 g (31.72 mmol) of 4-methyl-1,3-oxazole-5-carbaldehyde oxime are initially charged in 70 ml of acetic acid. At room temperature, 47.70 g (729.50 mmol) of zinc dust are added in small portions. The mixture is stirred at room temperature for 2 hours and the zinc dust is then filtered off with suction and washed twice with 50 ml of acetic acid. Under reduced pressure, the filtrate is freed from the solvent. The residue is treated with 20% strength aqueous sodium hydroxide solution until a pH of 11 is reached. During the addition, white crystals precipitate out. These are triturated with ethyl acetate and filtered off with suction. Under reduced pressure, the combined filtrates are freed from the solvent, and the residue is then purified chromatographically. This gives 1.34 g (38% of theory) of the title compound.

$^1$H-NMR (300 MHz, CDCl$_3$): δ=1.5 (s, 2H); 2.15 (s, 3H); 3.83 (s, 2H); 7.73 (s, 1H).

Example III-29

1,1-Dimethylethyl 2-[(4-bromophenyl)thio]-2-ethyl-butanoate

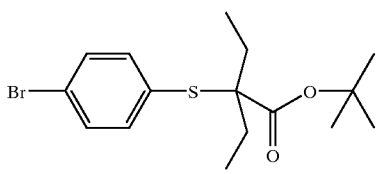

The synthesis was carried out similarly to Example II-1 from 4-bromothiophenol and 1,1-dimethylethyl 2-bromo-2-ethyl-butanoate [preparation, for example, similarly to Liebigs Ann. Chem. 725, 106–115 (1969); J. Am. Chem. Soc. 77, 946–947 (1955), and bromination with N-bromosuccinimide or bromine, for example similarly to Tetrahedron Lett. 1970, 3431; J. Org. Chem. 40, 3420 (1975)].

Yield: 15.9% of theory

¹H-NMR (300 MHz, CDCl₃): δ=0.96 (t, 6H); 1.58–1.74 (m, 4H); 7.28–7.35 (m, 2H); 7.39–7.46 (m, 2H).

Example III-30

1,1-Dimethylethyl 2-ethyl-2-[(4-formylphenyl)thio]-butanoate

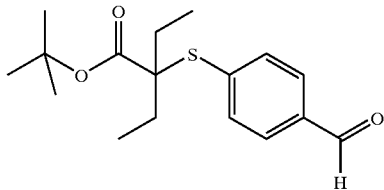

The synthesis was carried out similarly to Example II-2 using the compound from Example III-29 as starting material.

Yield: 70.4% of theory

¹H-NMR (300 MHz, CDCl₃): δ=0.96 (t, 6H); 1.64–1.87 (m, 4H); 7.60 (d, 2H); 7.78 (d, 2H); 10.1 (s, 1H).

Example III-31 tert-Butyl 2-ethyl-2-[(4-{[(2-furylmethyl)amino]methyl}phenyl)-sulphanyl]butanoate

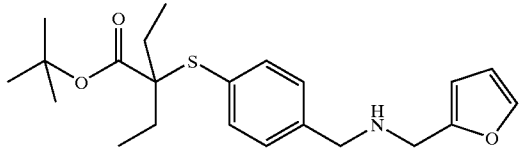

The synthesis was carried out similarly to Example III-13, using the compound from Example III-30 and furfurylamine as starting materials.

Yield: 83.1% of theory

¹H-NMR (300 MHz, CDCl₃): δ=0.93 (t, 6H); 1.43 (s, 9H); 1.60–1.75 (m, 4H); 3.78 (s, 4H); 6.18 (d, 1H); 6.28–6.35 (m, 1H); 7.25 (d, 2H); 7.35–7.38 (m, 1H); 7.43 (d, 2H).

Example III-32 tert-Butyl 2-methyl-2-[4-({[(4-methyl-1,3-oxazol-5-yl)methyl]amino}methyl)-phenoxy]-propanoate

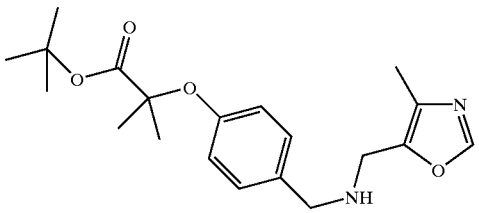

1.25 g (4.73 mmol) of tert-butyl 2-(4-formylphenoxy)-2-methylpropanoate (Example I-4) and 0.64 g (5.67 mmol) of (4-methyl-1,3-oxazol-5-yl)methylamine (Example III-28) are together initially charged in 1,2-dichloroethane. At room temperature, 1.50 g (7.09 mmol) of sodium triacetoxyborohydride are added. The reaction mixture is stirred at room temperature for 4 hours and then admixed with saturated sodium bicarbonate solution and extracted with ethyl acetate. The organic phase is dried over magnesium sulphate and freed from the solvent under reduced pressure. The residue is purified chromatographically on silica gel (dichloromethane/methanol 30:1) and then dried under reduced pressure. This gives 1.104 g (65% of theory) of the title compound.

¹H-NMR (200 MHz, CDCl₃): δ=1.45 (s, 9H); 1.55 (s, 6H); 2.11 (s, 3H); 3.70 (s, 2H); 3.77 (s, 2H); 6.70–6.90 (m, 2H); 7.10–7.20 (m, 2H); 7.29 (s, 1H); 7.75 (br s, 1H).

The following compounds were obtained similarly to the procedure of Example III-32:

Example III-33 tert-Butyl 2-(4-{[(2-methoxyethyl)amino]methyl}phenoxy)-2-methylpropanoate

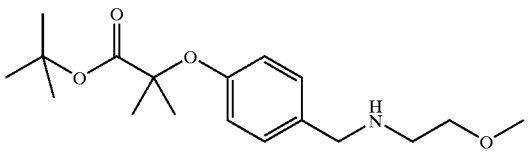

Yield: 92.8% of theory

¹H-NMR (300 MHz, CDCl₃): δ=1.44 (s, 9H); 1.55 (s, 6H); 2.48 (br s, 1H); 2.83 (t, 2H); 3.35 (s, 3H); 3.54 (t, 2H); 3.77 (s, 2H); 6.75–6.86 (m, 2H); 7.19 (d, 2H).

Example III-34 tert-Butyl 2-methyl-2-[4-({[(5-methyl-2-furyl)methyl]amino}methyl)-phenoxy]-propanoate

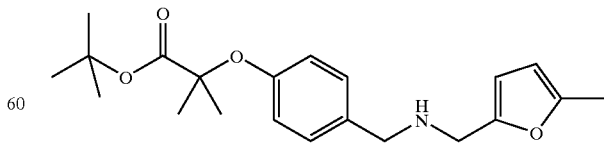

Yield: 55.1% of theory

¹H-NMR (300 MHz, CDCl₃): δ=1.44 (s, 9H); 1.55 (s, 6H); 2.27 (s, 3H); 3.71 (s, 4H); 5.83–5.92 (m, 1H); 6.00–6.08 (m, 1H); 6.75–6.88 (m, 2H); 7.12–7.24 (m, 2H).

Example III-35 tert-Butyl 2-[(4-{[(2-methoxyethyl)amino]methyl}phenyl)-sulphanyl]-2-methyl-propanoate

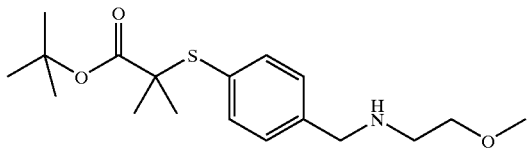

4.00 g (14.27 mmol) of tert-butyl 2-[(4-formylphenyl)sulphanyl]-2-methylpropanoate (Example II-2) and 1.07 g (14.27 mmol) of 2-methoxyethylamine are dissolved in 80 ml of 1,2-dichloroethane and, after 30 min and after 10 hours, admixed with 4.54 g (21.40 mmol) of sodium triacetoxyborohydride. The reaction is checked by TLC, and ethyl acetate and saturated sodium bicarbonate solution are then added and the product is extracted with ethyl acetate. The organic phase is washed with 1 N HCl and dried over magnesium sulphate, and the product is, after distillative removal of the solvent, purified by silica gel chromatography (ethyl acetate/cyclohexane 1:1).

Yield: 2.69 g (55.6% of theory)

$^1$H-NMR (300 MHz, CDCl$_3$): δ=1.45 (s, 15H); 2.96 (t, 2H); 3.37 (s, 3H); 3.72 (t, 2H); 4.13 (s, 2H); 7.52 (s, 4H).

The following compound was obtained similarly to the procedure of Example III-35:

Example III-36 tert-Butyl 2-methyl-2-{[4-({[(4-methyl-1,3-oxazol-5-yl)methyl]amino}methyl)-phenyl]-sulphanyl}propanoate

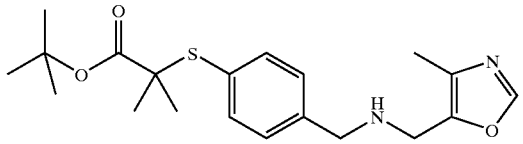

Yield: 68.8% of theory $^1$H-NMR (200 MHz, CDCl$_3$): δ=1.43 (s, 15H); 2.12 (s, 3H); 3.77 (s, 2H); 3.78 (s, 2H); 7.22–7.33 (m, 2H); 7.46 (d, 2H); 7.75 (s, 1H).

WORKING EXAMPLES 3

Example 3-1 tert-Butyl 2-[4-[[[2-[(2,4-dimethylphenyl)amino]-2-oxoethyl](2-furanylmethyl)-amino]methyl]phenoxy]-2-methyl-propanoate

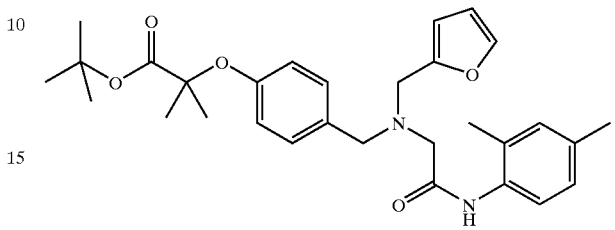

0.50 g (1.25 mmol) of the compound from Example III-16, 0.23 g (1.88 mmol) of 2,4-dimethylaniline, 0.22 g (1.63 mmol) of 1-hydroxy-1H-benzotriazole, 0.31 g (1.63 mmol) of EDC×HCl, 0.38 g (3.75 mmol) of 4-methylmorpholine and 0.01 g (0.08 mmol) of 4-dimethylaminopyridine are stirred in 30 ml of N,N-dimethylformamide at 0° C. for 2 hours and then at room temperature overnight. Water is added and the mixture is extracted with ethyl acetate, and the organic phases are then washed with 1 N hydrochloric acid, water, saturated sodium bicarbonate solution and saturated sodium chloride solution and then dried over magnesium sulphate. The solvent is distilled off and the residue is purified by flash chromatography on silica gel (cyclohexane/dichloroethane 2:1→cyclohexane/ethyl acetate 10:1→4:1). Recrystallization from n-heptane gives the target compound in a yield of 78%.

Melting point: 90–91° C.

Example 3-2 tert-Butyl 2-[4-[[[2-[(2,4-dimethylphenyl)methylamino]-2-oxoethyl](2-furanyl-methyl)amino]methyl]phenoxy]-2-methyl-propanoate

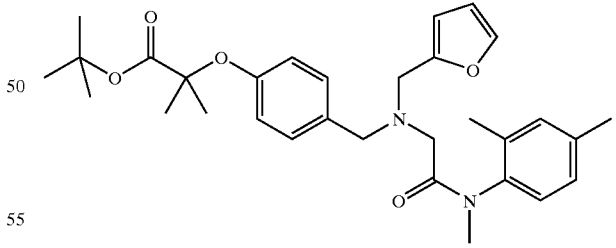

At 0° C., 0.51 g (1.00 mmol) of the compound from Example 3-1 and 0.04 g (1.10 mmol) of sodium hydride are stirred for 30 min and then admixed with 0.07 ml (1.10 mmol) of iodomethane and then with water. The mixture is extracted with ethyl acetate, the extract is washed with water and saturated sodium chloride solution and dried over magnesium sulphate, the solvent is distilled off and the residue is purified by flash chromatography on silica gel (cyclohexane/dichloromethane 3:1→dichloromethane→dichloromethane/ethyl acetate 15:1). Recrystallization from n-pentane gives the target compound in a yield of 51%.

Melting point: 80–81° C.

Example 3-3 tert-Butyl 2-[4-[[[2-[(2,4-dimethylphenyl)amino]ethyl](2-furanylmethyl)-amino]-methyl]phenoxy]-2-methyl-propanoate

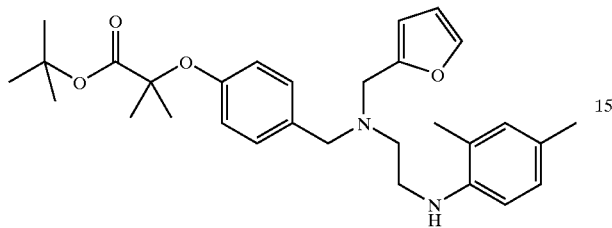

In 5 ml toluene, 0.25 g (0.50 mmol) of the compound from Example 3-1 is treated with 0.30 ml of 2 M borane-dimethyl sulphide solution in tetrahydrofuran, and the mixture is heated at the boil for 2 hours. The mixture is then stirred in the presence of 5 ml of 2 N sodium carbonate solution for 1 hour and the organic phase is washed with water and with saturated sodium chloride solution. The organic phase is dried over magnesium sulphate and the solvent is distilled off, and the residue is then purified using silica gel flash chromatography (cyclohexane/dichloromethane 3:1→cyclohexane/ethyl acetate 10:1). This gives the target compound in a yield of 37%.

$^1$H-NMR (200 MHz, CDCl$_3$): δ=1.43 (s, 9H), 1.55 (s, 6H), 2.15 (s, 3H), 2.22 (s, 3H), 2.73–2.87 (m, 2H), 3.09–3.22 (m, 2H); 3.57 (s, 2H), 3.63 (s, 2H), 6.12–6.19 (m, 2H), 6.28–6.35 (m, 1H), 6.47 (d, 1H), 6.73–6.95 (m, 4H), 7.20 (d, 1H), 7.34–7.40 (m, 1H).

MS (ESI): 493 [M+H]$^+$, 985 [M+H]$^+$.

Example 3-4

2-[4-[[[2-[(2,4-Dimethylphenyl)amino]-2-oxoethyl](2-furanylmethyl)amino]-methyl]phenoxy]-2-methyl-propionic acid

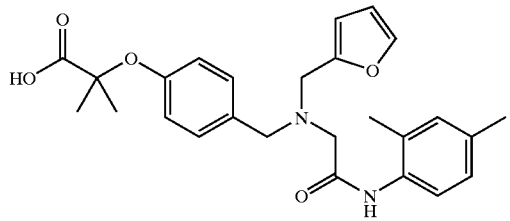

7.09 g (14.00 mmol) of the compound from Example 3-1 and 35 ml of trifluoroacetic acid are stirred at room temperature in 35 ml of dichloromethane for 2 hours. The solvent is distilled off and the residue is then dissolved in ethyl acetate, washed with water, 20 per cent strength sodium acetate solution and saturated sodium chloride solution and then dried over magnesium sulphate. The solvent is removed and the residue is then purified by flash chromatography on silica gel (dichloromethane→dichloromethane/ethyl acetate 5:1→2:1→1:1). The gives the target compound in a yield of 82%.

$^1$H-NMR (200 MHz, CDCl$_3$): δ=1.57 (s, 6H), 2.24 (s, 3H), 2.27 (s, 3H), 3.31 (s, 2H), 3.67 (s, 2H), 3.75 (s, 2H), 6.22–6.36 (m, 2H), 6.88 (d, 2H), 6.93–7.03 (m, 2H), 7.23 (d, 2H), 7.34–7.40 (m, 1H), 7.78 (d, 1H), 8.00 (broad s, 1H), 9,09 (s, 1H).

MS (ESI): 451 [M+H]$^+$, 901 [2M+H]$^+$.

The following compounds are obtained similarly to the procedure of Example 3-4:

Example 3-5

2-[4-[[[2-[(2,4-Dimethylphenyl)methylamino]-2-oxoethyl](2-furanylmethyl)amino]-methyl]phenoxy]-2-methyl-propionic acid

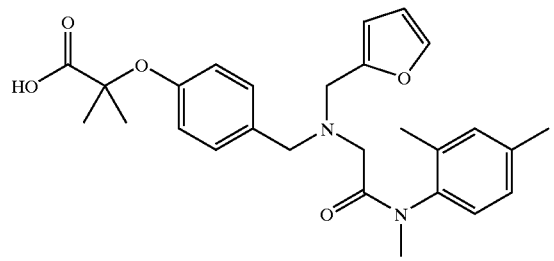

Yield: 85%

$^1$H-NMR (200 MHz, CDCl$_3$): δ=1.46 (s, 6H), 1.92 (s, 3H), 2.24 (s, 3H), 2.73 (q, 2H), 3.00 (s, 3H), 3.30 (broad s, 1H), 3.63 (d, 2H), 3.78 (d, 2H), 6.19 (d, 1H), 6.30–6.40 (m, 1H), 6.74 (d, 2H), 6.80–7.10 (m, 5H), 7.52–7.57 (m, 1H).

MS (ESI): 465 [M+H]$^+$, 487 [M+Na]$^+$.

Example 3-6

2-[4-[[[2-[(2,4-Dimethylphenyl)amino]ethyl](2-furanylmethyl)amino]-methyl]phen-oxy]-2-methyl-propionic acid

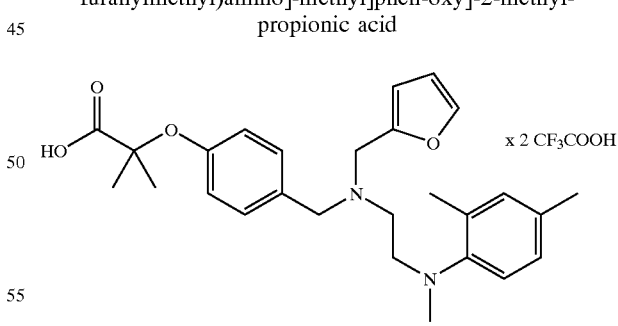

Yield: 60%

$^1$H-NMR (200 MHz, DMSO-d$_6$): δ=1.49 (s, 6H), 2.01 (s, 3H), 2.12 (s, 3H), 2.55–2.72 (broad m, 2H), 2.97–3.20 (broad m, 2H), 3.46–3.78 (m, 4H), 4.40 (broad s, 1H), 6.20–6.50 (m, 3H), 6.68–6.88 (m, 4H), 7.12–7.30 (m, 2H), 7.56–7.68 (m, 1H), 13.00 (broad s, 1H).

MS (ESI): 437 [M+H]$^+$, 873 [2M+H]$^+$.

Example 3-7

1,1-Dimethylethyl 2-[4-[[[(2-methoxyethyl)[2-[[4-(1-methylethyl)-2-(trifluoro-methyl)phenyl]amino]-2-oxoethyl]amino]methyl]phenoxy]-2-methyl-propionate

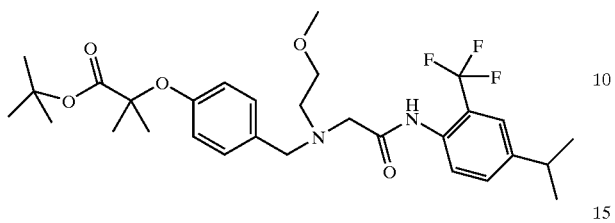

0.533 g (1.65 mmol) of tert-butyl 2-(4-{[(2-methoxyethyl)amino]methyl}phenoxy)-2-methylpropanoate (Example III-33) is initially charged in 6 ml of dimethylformamide. At room temperature, 0.588 g (1.81 mmol) of 2-bromo-N-[4-isopropyl-2-(trifluoromethyl)phenyl]acetamide (Example III-17) and 0.152 g (1.81 mmol) of sodium bicarbonate are added. The mixture is set at 90° C. for 2 hours. The reaction mixture is then allowed to cool, and water is added. The mixture is extracted once with ethyl acetate and the organic phase is washed three times with water and once with saturated sodium chloride solution. The organic phase is dried over sodium sulphate and freed from the solvent under reduced pressure. The residue is purified chromatographically on silica gel (cyclohexane/ethyl acetate 4:1) and the product is then dried under reduced pressure. This gives 0.885 g (95% of theory) of the title compound.

$^1$H-NMR (400 MHz, CDCl$_3$): δ=1.25 (d, 6H); 1.42 (s, 9H); 1.55 (s, 6H); 2.80 (t, 2H); 2.93 (sept., 1H); 3.28 (s, 3H); 3.30 (s, 2H); 3.54 (t, 2H); 3.70 (s, 2H); 6.80 (d, 2H); 7.20 (d, 2H); 7.39 (dd, 1H); 7.45 (d, 1H); 8.17 (d, 1H); 9.65 (br s, 1H).

Example 3-8

2-[4-[[(2-Methoxyethyl)[2-[[4-(1-methylethyl)-2-(trifluoromethyl)phenyl]amino]-2-oxoethyl]amino]methyl]phenoxy]-2-methyl-propionic acid

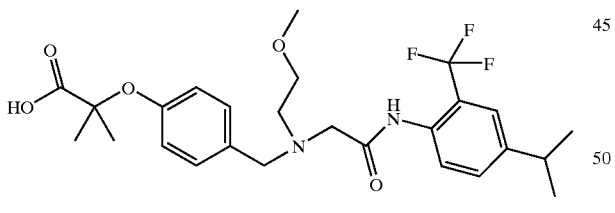

0.842 g (1.49 mmol) of the compound from Example 3-7 is initially charged in 10 ml of dichloromethane. At room temperature, 10 ml of trifluoroacetic acid are added. The reaction mixture is stirred at room temperature for 2 hours. The mixture is then concentrated under reduced pressure using a rotary evaporator. The residue is taken up in ethyl acetate and washed with water, 20% strength sodium acetate solution, water and saturated sodium chloride solution. The organic phase is dried over magnesium sulphate and freed from the solvent under reduced pressure. The product is purified chromatographically on silica gel (dichloromethane/methanol 30:1) and then dried under reduced pressure. This gives 0.648 g (85% of theory) of the title compound.

$^1$H-NMR (200 MHz, CDCl$_3$): δ=1.26 (d, 6H); 1.55 (s, 6H); 2.81 (t, 2H); 2.91 (sept., 1H); 3.28 (s, 3H); 3.31 (s, 2H); 3.55 (t, 2H); 3.72 (s, 2H); 6.90 (d, 2H); 7.25 (d, 2H); 7.35–7.49 (m, 2H); 8.12 (d, 1H); 9.62 (br s, 1H).

Example 3-9

2-[4-[[(2-Methoxyethyl)[2-[[4-(1-methylethyl)-2-(trifluoromethyl)phenyl]amino]-2-oxoethyl]amino]methyl]phenoxy]-2-methyl-propionic acid hydrochloride

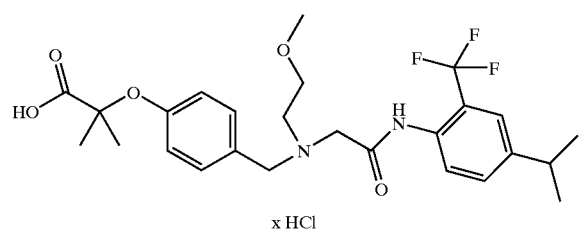

x HCl 0.4 g (0.78 mmol) of the compound from Example 3-7 are dissolved in 4 ml of ethyl acetate. At 40° C., first 8 ml of 1N hydrochloric acid (in diethyl ether) and then 12 ml of diethyl ether are added. The mixture is allowed to stand at 4° C. for one hour. The precipitated crystals are filtered off with suction, washed with a mixture of ethyl acetate and diethyl ether (ratio 1: 1) and then dried at 40° C. under reduced pressure for 20 hours. This gives 0.362 g (84.5% of theory) of the title compound.

$^1$H-NMR (200 MHz, DMSO): δ=1.22 (d, 6H); 1.55 (s, 6H); 2.94–3.08 (m, 1H); 3.28 (s, 3H); 3.30–3.40 (m, 2H); 3.60–3.80 (m, 2H); 4.00–4.20 (m, 2H); 4.30–4.50 (m, 2H); 6.86 (d, 2H); 7.20–7.70 (m, 5H); 10.25 (br s, 1H); 13.18 (br s, 1H).

Example 3-10

1,1-Dimethylethyl 2-[4-[[[2-[(4-cyclohexyl-2-methylphenyl)amino]-2-oxoethyl](2-methoxyethyl)-amino]methyl]phenoxy]-2-methyl-propionate

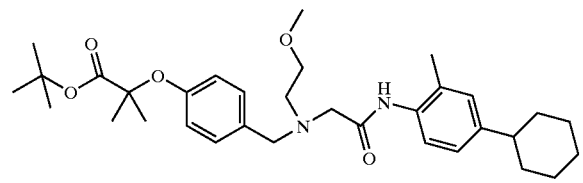

0.303 g (0.94 mmol) of tert-butyl 2-(4-{[(2-methoxyethyl)amino]methyl}phenoxy)-2-methylpropanoate (Example III-33) is initially charged in 5 ml of dimethylformamide. At room temperature, 0.319 g (1.03 mmol) of 2-bromo-N-(4-cyclohexyl-2-methylphenyl)acetamide (Example III-19) and 0.086 g (1.03 mmol) of sodium bicarbonate are added. The mixture is stirred at 90° C. for 2 hours. The reaction mixture is then allowed to cool, and water is added. The mixture is extracted with ethyl acetate and the organic phase is washed with water and saturated sodium chloride solution. The organic phase is dried over sodium sulphate and freed from the solvent under reduced pressure. The residue is purified chromatographically on silica gel (cyclohexane/ethyl acetate 3:1) and the product is dried under reduced pressure. This gives 0.464 g (90% of theory) of the title compound.

$^1$H-NMR (300 MHz, CDCl$_3$): δ=1.20–1.45 (m, 14H); 1.50 (s, 6H); 1.70–1.90 (m, 5H); 2.25 (s, 3H); 2.36–2.48 (m, 1H); 2.80 (t, 2H); 3.25 (s, 5H); 3.5 (t, 2H) 3.69 (s, 2H); 6.80 (d, 2H); 6.98–7.06 (m, 2H); 7.15–7.25 (m, 2H); 7.85 (d, 1H); 9.25 (br s, 1H).

Example 3-11

2-[4-[[[2-[(4-Cyclohexyl-2-methylphenyl)amino]-2-oxoethyl](2-methoxyethyl)-amino]methyl]phenoxy]-2-methyl-propionic acid hydrochloride

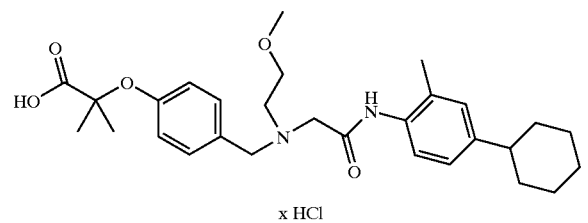

x HCl 0.398 g (0.72 mmol) of the compound from Example 3-10 is initially charged in 5 ml of dichloromethane. At room temperature, 5 ml of trifluoroacetic acid are added. The reaction mixture. is stirred at room temperature for 2 hours. The mixture is then concentrated under reduced pressure using a rotary evaporator. The residue is taken up in ethyl acetate and washed with water, 20% strength sodium acetate solution, water and saturated sodium chloride solution. The organic phase is dried over magnesium sulphate and freed from the solvent under reduced pressure. The product is purified chromatographically on silica gel (dichloromethane/methanol 30:1). With heating, the residue is dissolved in dichloromethane, 1N hydrochloric acid in diethyl ether is added and n-heptane is added dropwise until the mixture becomes slightly turbid. The product is filtered off with suction, washed with diethyl ether and dried at 40° C. under reduced pressure. This gives 0.187 g (49% of theory) of the title compound.

$^1$H-NMR (300 MHz, CDCl$_3$): δ=1.15–1.47 (m, 5H); 1.55 (s, 6H); 1.68–1.90 (m, 5H); 2.25 (s, 3H); 2.36–2.49 (m, 1H); 2.85 (t, 2H); 3.28 (s, 3H); 3.30 (s, 2H); 3.52 (t, 2H); 3.72 (s, 2H); 6.87 (d, 2H); 6.99–7.10 (m, 2H); 7.25 (d, 2H); 7.80 (d, 1H); 9.25 (br s, 1H).

The following compounds were obtained similarly to the procedure of Examples 3-7 and 3-10:

Example 3-12

1,1-Dimethylethyl 2-[4-[[[2-[[2,4-bis(trifluoromethyl)phenyl]amino]-2-oxoethyl][(5-methyl-2-furanyl)-methyl]amino]methyl]phenoxy]-2-methyl-propionate

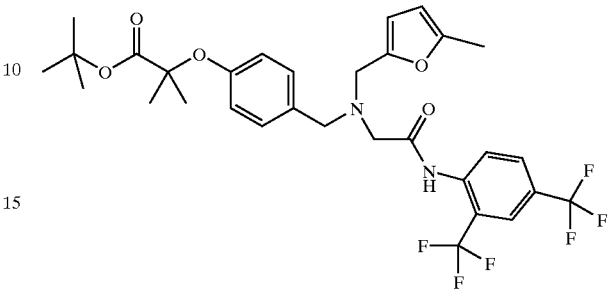

Yield: 88% of theory $^1$H-NMR (300 MHz, CDCl$_3$): δ=1.40 (s, 9H); 1.55 (s, 6H); 2.15 (s, 3H); 3.30 (s, 2H); 3.65 (s, 4H); 5.85 (m, 1H); 6.12 (d, 1H); 6.81 (m, 2H); 7.20 (m, 2H); 7.25 (m, 1H); 7.35 (s, 1H); 8.57 (d, 1H); 9.85 (br s, 1H).

Example 3-13

1,1-Dimethylethyl 2-[[4-[[[2-[[5-chloro-2-methyl4-(trifluoromethoxy)phenyl]-amino]-2-oxoethyl][(4-methyl-5-oxazolyl)methyl]amino]methyl]phenyl]thio]-2-methyl-propionoate

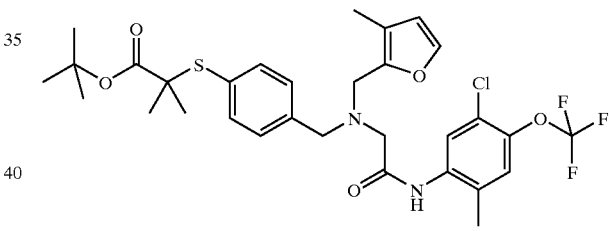

Yield: 80.2% of theory $^1$H-NMR (300 MHz, CDCl$_3$): δ=1.40 (s, 9H); 1.41 (s, 6H); 2.14 (s, 3H); 2.29 (s, 3H); 3.32 (s, 2H); 3.73 (s, 2H); 3.77 (s, 2H); 7.13 (s, 1H); 7.23–7.31 (m, 2H); 7.49 (d, 2H); 7.78 (s, 1H); 8.30 (s, 1H); 9.05 (s, 1H).

Example 3-14

1,1-Dimethyl-ethyl 2-[[4-[[[2-[[5-chloro-2-methyl-4-(trifluoromethoxy)phenyl]-amino]-2-oxoethyl](2-furanylmethyl)amino]methyl]phenyl]thio]-2-methyl-propionate

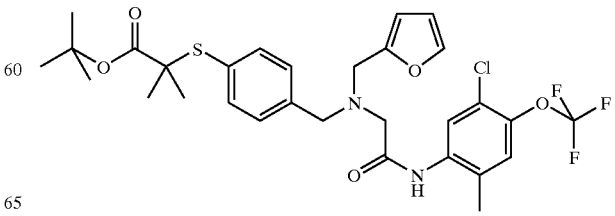

Yield: 85.1% of theory

¹H-NMR (300 MHz, CDCl₃): δ=1.39 (s, 9H); 1.41 (s, 6H); 2.30 (s, 3H); 3.31 (s, 2H); 3.74 (s, 4H); 6.28 (d, 1H); 6.31–6.35 (m, 1H); 7.12 (s, 1H); 7.27 (d, 2H); 7.35–7.38 (m, 1H); 7.48 (d, 2H); 8.31 (s, 1H); 9.19 (s, 1H).

Example 3-15

1,1-Dimethylethyl 2-[[4-[[[2-[(2,4-dimethylphenyl)amino]-2-oxoethyl](2-furanyl-methyl)amino]-methyl]phenyl]thio]-2-ethyl-butanoate

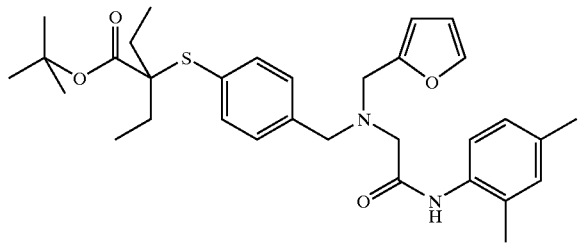

Yield: 73.4% of theory

¹H-NMR (200 MHz, CDCl₃): δ=0.95 (t, 6H); 1.41 (s, 9H); 1.55–1.78 (m, 4H); 2.26 (s, 3H); 2.28 (s, 3H); 3.30 (s, 2H); 3.73 (s, 2H); 3.74 (s, 2H); 6.20–6.38 (m, 2H); 6.90–7.08 (m, 2H); 7.28 (d, 2H); 7.35–7.50 (m, 3H); 7.75–7.88 (m, 1H); 9.05 (s, 1H).

Example 3-16

1,1-Dimethylethyl 2-[[4-[[[2-[(4-cyclohexyl-2-methylphenyl)amino]-2-oxoethyl](2-methoxyethyl)-amino]methyl]phenyl]thio]-2-methyl-propionoate

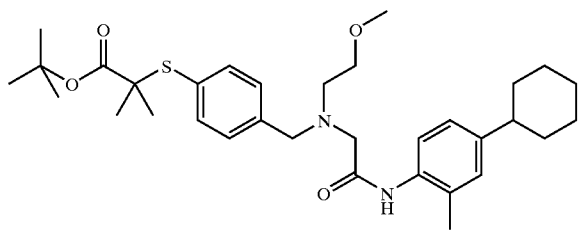

Yield: 81.9% of theory

¹H-NMR (200 MHz, CDCl₃): δ=1.31–1.47 (m, 18H); 1.70–1.95 (m, 6H); 2.20–2.31 (m, 4H); 2.35–2.51 (m, 1H); 2.82 (t, 2H); 3.28 (s, 5H); 3.51 (t, 2H); 3.77 (s, 2H); 7.03 (d, 2H); 7.31 (d, 2H); 7.46 (d, 2H); 7.83 (d, 1H); 9.24 (s, 1H).

Example 3-17

1,1-Dimethylethyl 2-[[4-[[[2-[[4-(1,1-dimethylethyl)-2-methylphenyl]amino]-2-oxoethyl](2-methoxy-ethyl)amino]methyl]phenyl]thio]-2-methyl-propionate

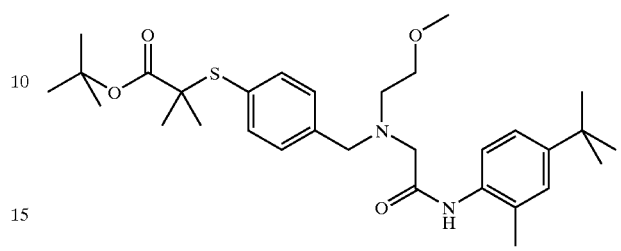

Yield: 82.9% of theory

¹H-NMR (300 MHz, CDCl₃): δ=1.29 (s, 12H); 1.40 (s, 9H); 1.42 (s, 6H); 2.82 (t, 2H); 3.29 (s, 5H); 3.51 (t, 2H); 3.77 (s, 2H); 7.13–7.40 (m, 4H); 7.40–7.53 (m, 2H); 7.86 (d, 1H); 9.26 (br s, 1H).

Example 3-18

1,1-Dimethylethyl 2-[[4-[[[2-[[5-chloro-2-methyl-4-(trifluoromethoxy)phenyl]-amino]-2-oxoethyl](2-furanylmethyl)amino]methyl]phenyl]thio]-2-ethyl-butanoate

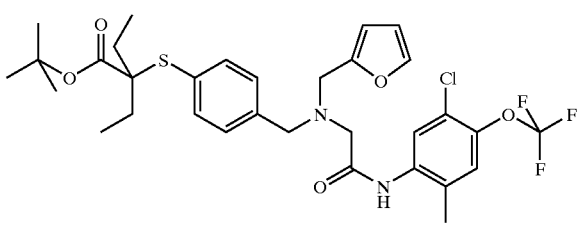

Yield: 86.8% of theory

¹H-NMR (200 MHz, CDCl₃): δ0.94 (t, 6H); 1.41 (s, 9H); 1.55–1.75 (m, 4H); 2.30 (s, 3H); (s, 2H); 3.73 (s, 2H); 3.75 (s, 2H); 6.24–6.38 (m, 2H); 7.12 (s, 1H); 7.26 (d, 2H); 7.36 (d, 1H); 7.44 (d, 2H); 8.31 (s, 1H); 9.19 (s, 1H).

Example 3-19

1,1-Dimethylethyl 2-[[4-[[[2-[[5-chloro-2-methyl-4-(trifluoromethoxy)phenyl]-amino]-2-oxoethyl](2-methoxyethyl)amino]methyl]phenyl]thio]-2-methyl-propionate

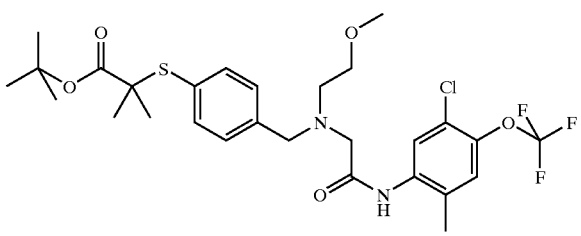

Yield: 57.4% of theory

¹H-NMR (300 MHz, CDCl₃): δ=1.40 (s, 9H); 1.41 (s, 6H); 2.29 (s, 3H); 2.83 (t, 2H); 3.27 (s, 3H); 3.29 (s, 2H);

3.51 (t, 2H); 3.77 (s, 2H); 7.11 (s, 1H); 7.30 (d, 2H); 7.46 (d, 2H); 8.29 (s, 1H); 9.44 (s, 1H).

Example 3-20

1,1-Dimethylethyl 2-methyl-2-[4-[[[2-[[4-(1-methylethyl)-2-(trifluoromethyl)-phenyl]amino]-2-oxoethyl][(5-methyl-2-furanyl)methyl]amino]methyl]phenoxy]-propionate

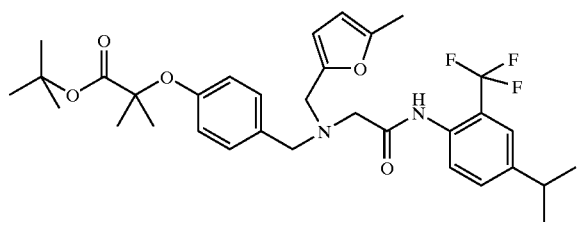

Yield: 94% of theory $^{1}$H-NMR (400 MHz, CDCl$_3$): δ=1.25 (d, 6H); 1.40 (s, 9H); 1.55 (s, 6H); 2.17 (s, 3H); 2.88 (sept., 1H); 3.25 (s, 2H); 3.15 (m, 4H); 5.85 (m, 1H); 6.10 (d, 1H); 6.81 (d, 2H); 7.21 (d, 2H); 7.35 (m, 1H); 7.43 (m, 1H); 8.15 (d, 1H); 9.67 (s, 1H).

Example 3-21

1,1-Dimethylethyl 2-[4-[[[2-[(2-ethoxy-1-naphthalenyl)amino]-2-oxoethyl][(5-methyl-2-furanyl)-methyl]amino]methyl]phenoxy]-2-methyl-propionate

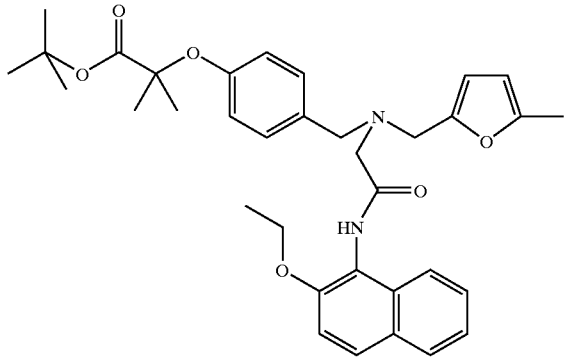

Yield: 95% of theory $^{1}$H-NMR (200 MHz, CDCl$_3$): δ=1.30 (t, 3H); 1.43 (s, 9H); 1.54 (s, 6H); 2.25 (s, 3H); 3.44 (s, 2H); 3.78–3.82 (m, 4H); 4.15 (q, 2H); 5.89–5.94 (m, 1H); 6.15–6.18 (m, 1H); 6.84 (d, 2H); 7.20–7.38 (m, 4H); 7.45 (t, 1H); 7.65 (d, 1H); 7.75–7.85 (m, 2H); 9.05 (br s, 1H).

Example 3-22

1,1-Dimethylethyl 2-methyl-2-[4-[[[(5-methyl-2-furanyl)methyl][2-oxo-2-[(5,6,7,8-tetrahydro-1-naphthalenyl)amino]ethyl]amino]methyl]phenoxy]-propionate

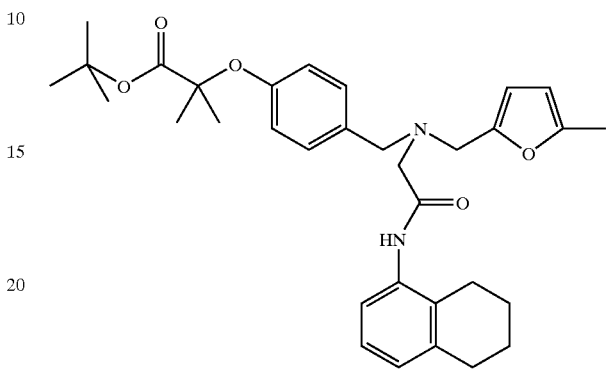

Yield: 91% of theory $^{1}$H-NMR (300 MHz, CDCl$_3$): δ=1.40 (s, 9H); 1.55 (s, 6H); 1.70–1.95 (m, 4H); 2.20 (s, 3H); 2.65–2.82 (m, 4H); 3.24 (s, 2H); 3.67 (s, 4H); 5.86–5.90 (m, 1H); 6.10–6.14 (d, 1H); 6.78–6.93 (m, 3H); 7.08 (t, 1H); 7.22 (d, 2H); 7.89 (d, 1H); 9.20 (br s, 1H).

Example 3-23

1,1-Dimethylethyl 2-[4-[[[2-[(2,4-dichlorophenyl)amino]-2-oxoethyl](2-methoxy-ethyl)amino]methyl]-phenoxy]-2-methyl-propionate

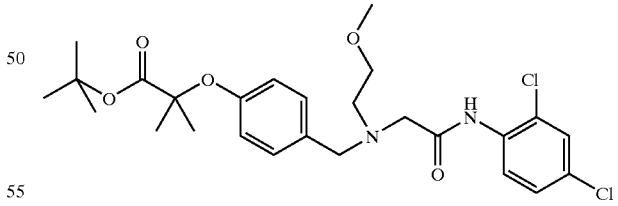

Yield: 87% of theory $^{1}$H-NMR (300 MHz, CDCl$_3$): δ=1.39 (s, 9H); 1.53 (s, 6H); 2.81 (t, 2H); 3.24 (s, 3H); 3.29 (s, 2H); 3.51 (t, 2H); 3.70 (s, 2H); 6.80 (m, 2H); 7.10–7.30 (m, 3H); 7.38 (d, 1H); 8.42 (d, 1H); 9.93 (br s, 1H).

Example 3-24

1,1-Dimethylethyl 2-[4-[[(2-methoxyethyl)[2-[[4-(1-naphthalenyloxy)-2-(trifluoro-methyl)phenyl]amino]-2-oxoethyl]amino]methyl]phenoxy]-2-methyl-propionate

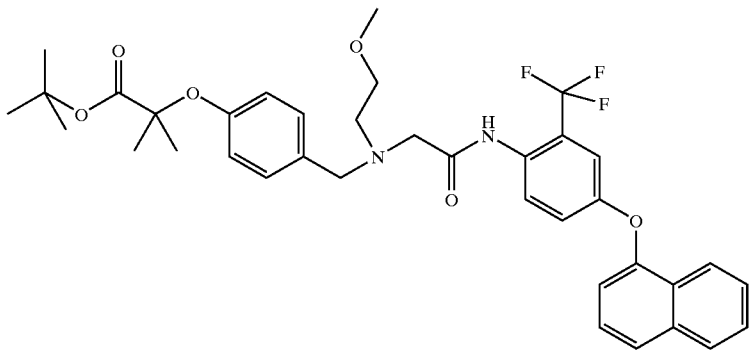

Yield: 95.5% of theory $^1$H-NMR (300 MHz, CDCl$_3$): δ=1.41 (s, 9H); 1.55 (s, 6H); 2.80 (t, 2H); 3.28 (s, 3H); 3.30 (s, 2H); 3.54 (t, 2H); 3.70 (s, 2H); 6.80 (d, 2H); 6.95 (d, 1H); 7.13–7.25 (m, 3H); 7.34 (d, 1H); 7.40 (t, 1H); 7.47–7.58 (m, 2H); 7.66 (d, 1H); 7.89 (dd, 1H); 8.07–8.21 (m, 2H); 9.68 (br s, 1H).

Example 3-25

1,1-Dimethylethyl 2-[4-[[[2-[[5-[(ethylsulphonyl)methyl]-1-naphthalenyl]amino]-2-oxoethyl](2-methoxyethyl)amino]methyl]phenoxy]-2-methyl-propionate

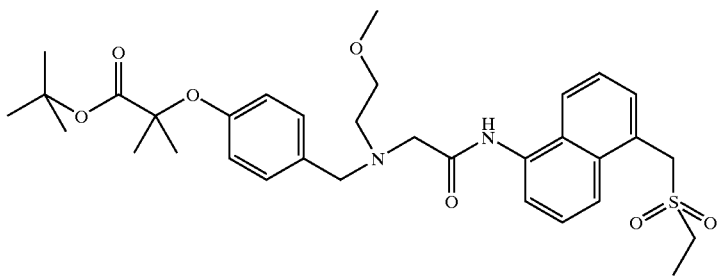

Yield: 91% of theory $^1$H-NMR (200 MHz, CDCl$_3$): δ=1.20–1.37 (m, 12H); 1.55 (s, 6H); 2.83–2.94 (m, 4H); 3.22 (s, 3H); 3.39 (s, 2H); 3.55 (t, 2H); 3.77 (s, 2H); 4.77 (s, 2H); 6.81 (d, 2H); 7.15–7.30 (m, 2H); 7.50–7.70 (m, 3H); 7.91 (d, 1H); 8.12 (d, 1H); 8.22 (d, 1H); 10.18 (br s, 1H).

Example 3-26

1,1-Dimethylethyl 2-methyl-2-[4-[[[2-[[4-(1-methylethyl)-2-(trifluoromethyl)-phenyl]amino]-2-oxoethyl][(4-methyl-5-oxazolyl)methyl]amino]methyl]phenoxy]-propionate

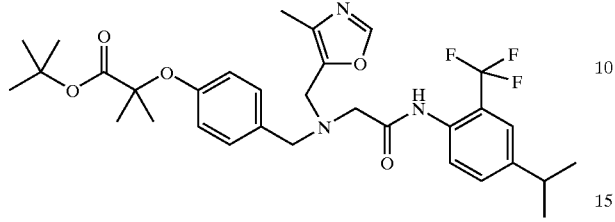

Yield: 83.5% of theory

¹H-NMR (300 MHz, CDCl₃): δ=1.25 (d, 6H); 1.40 (s, 9H); 1.55 (s, 6H); 2.10 (s, 3H); 2.85–3.00 (sept., 1H); 3.28 (s, 2H); 3.66 (s, 2H); 3.75 (s, 2H); 6.82 (d, 2H); 7.20 (d, 2H); 7.38 (dd, 1H); 7.40–7.45 (m, 1H); 7.75 (s, 1H); 8.14 (d, 1H); 9.45 (br s, 1H).

Example 3-27

1,1-Dimethylethyl 2-[4-[[[2-[[2,4-bis(trifluoromethyl)phenyl]amino]-2-oxoethyl][(4-methyl-5-oxazolyl)-methyl]amino]methyl]phenoxy]-2-methyl-propionate

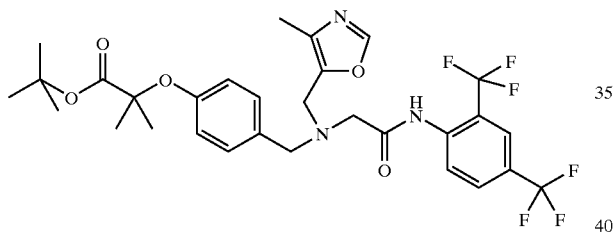

Yield: 79.5% of theory

¹H-NMR (300 MHz, CDCl₃): δ=1.40 (s, 9H); 1.55 (s, 6H); 2.11 (s, 3H); 3.30 (s, 2H); 3.68 (s, 2H); 3.76 (s, 2H); 6.81 (d, 2H); 7.18 (d, 2H); 7.70–7.80 (m, 2H); 7.86 (s, 1H); 8.56 (d, 1H); 9.71 (br s, 1H).

Example 3-28

1,1-Dimethylethyl 2-[4-[[[2-[[4-(1,1-dimethylethyl)-2-methylphenyl]amino]-2-oxoethyl](2-methoxy-ethyl)amino]methyl]phenoxy]-2-methyl-propionate

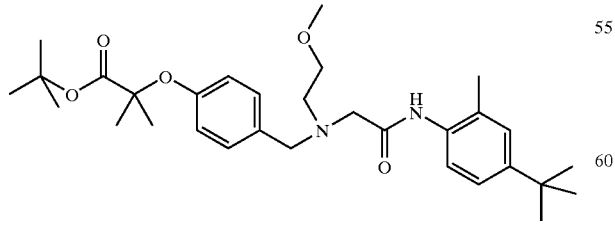

Yield: 81% of theory

¹H-NMR (300 MHz, CDCl₃): δ=1.30 (s, 9H); 1.40 (s, 9H); 1.55 (s, 6H); 2.38 (s, 3H); 2.80 (t, 2H); 3.29 (s, 5H); 3.50 (t, 2H); 3.70 (s, 2H); 6.80 (d, 2H); 7.15–7.25 (m, 4H); 7.78 (d, 1H); 9.30 (br s, 1H).

Example 3-29

1,1-Dimethylethyl 2-[4-[[[2-[[2,4-bis(trifluoromethyl)phenyl]amino]-2-oxoethyl](2-methoxyethyl)-amino]methyl]phenoxy]-2-methyl-propionate

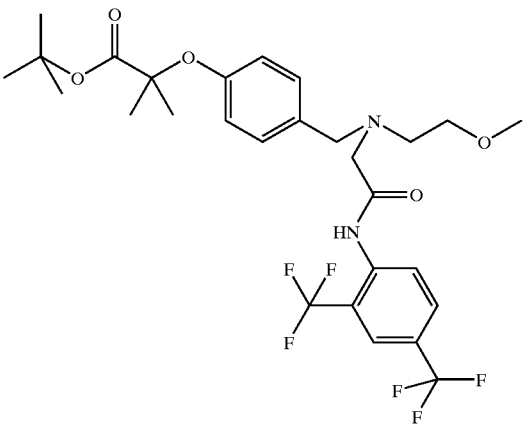

Yield: 80% of theory

¹H-NMR (300 MHz, CDCl₃): δ=1.39 (s, 9H); 1.55 (s, 6H); 2.82 (t, 2H); 3.28 (s, 3H); 3.33 (s, 2H); 3.52 (t, 2H); 3.71 (s, 2H); 6.80 (d, 2H); 7.18 (d, 2H); 7.78 (d, 1H); 7.84 (s, 1H); 8.60 (d, 1H); 9.98 (br s, 1H).

Example 3-30

1,1-Dimethylethyl 2-[4-[[[2-[[2,4-bis(trifluoromethyl)phenyl]amino]-2-oxoethyl](2-furanylmethyl)-amino]methyl]phenoxy]-2-methyl-propionate

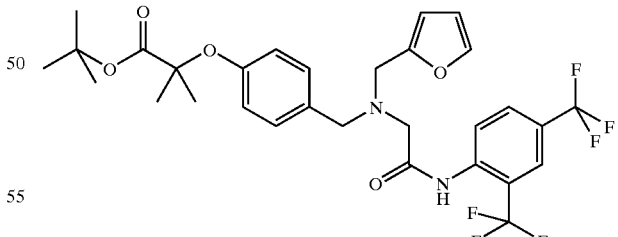

Yield: 84% of theory

¹H-NMR (300 MHz, CDCl₃): δ=1.40 (s, 9H); 1.55 (s, 6H); 3.30 (s, 2H); 3.65 (s, 2H); 3.75 (s, 2H); 6.20–6.30 (m, 1H); 6.30–6.38 (m, 1H); 6.82 (d, 2H); 7.18 (d, 2H); 7.36–7.39 (m, 1H); 7.75 (d, 1H); 7.90 (s, 1H); 8.60 (d, 1H); 9.82 (br s, 1H).

Example 3-31

1,1-Dimethylethyl 2-[[4-[[[2-[[2,4-bis(trifluoromethyl)phenyl]amino]-2-oxoethyl](2-furanylmethyl)-amino]methyl]phenyl]thio]-2-methyl-propionate

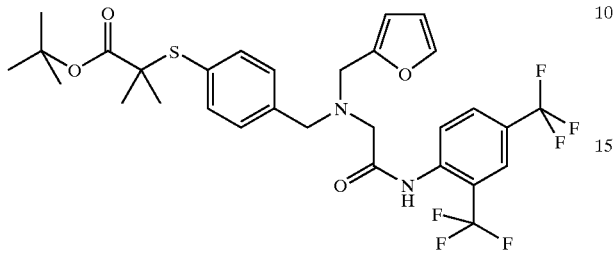

Yield: 92% of theory

¹H-NMR (300 MHz, CDCl₃): δ=1.40 (s, 9H); 1.45 (s, 6H); 3.31 (s, 2H); 3.74–3.80 (m, 4H); 6.25 (d, 1H); 6.30–6.38 (m, 1H); 7.22–7.40 (m, 3H); 7.50 (d, 2H); 7.78 (d, 1H); 7.90 (s, 1H); 8.61 (d, 1H); 9.78 (br s, 1H).

The following compounds were obtained similarly to the procedure of Example 3-8:

Example 3-32

2-[4-[[[2-[[2,4-Bis(trifluoromethyl)phenyl]amino]-2-oxoethyl][(5-methyl-2-furanyl)-methyl]amino]methyl]phenoxy]-2-methyl-propionic acid

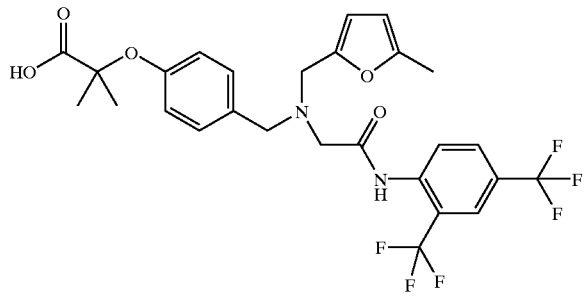

Yield: 83.4% of theory

¹H-NMR (300 MHz, CDCl₃): δ=1.56 (s, 6H); 2.15 (s, 3H); 3.29 (s, 2H); 3.69 (s, 2H); 3.71 (s, 2H); 5.80–5.88 (m, 1H); 6.13 (d, 1H); 6.89–6.98 (m, 2H); 7.20–7.35 (m, 2H); 7.74 (d, 1H); 7.86 (s, 1H); 8.56 (d, 1H); 9.79 (s, 1H).

Example 3-33

2-[[4-[[[2-[[5-Chloro-2-methyl-4-(trifluoromethoxy)phenyl]amino]-2-oxoethyl][(4-methyl-5-oxazolyl)methyl]amino]methyl]phenyl]thio]-2-methyl-propionic acid

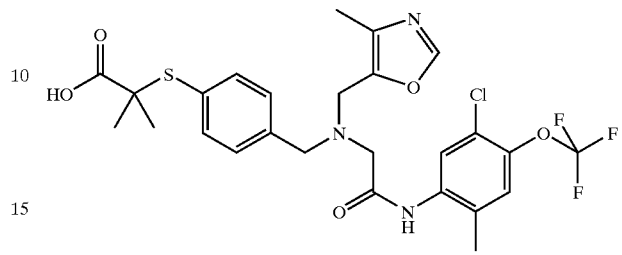

Yield: 62.8% of theory

¹H-NMR (200 MHz, CDCl₃): δ=1.47 (s, 6H); 2.11 (s, 3H); 2.28 (s, 3H); 3.35 (s, 2H); 3.74 (s, 2H); 3.77 (s, 2H); 7.11 (s, 1H); 7.20–7.30 (m, 2H); 7.49 (d, 2H); 7.80 (s, 1H); 8.28 (s, 1H); 9.04 (s, 1H).

Example 3-34

2-[[4-[[[2-[[5-Chloro-2-methyl-4-(trifluoromethoxy)phenyl]amino]-2-oxoethyl](2-furanylmethyl)amino]methyl]phenyl]thio]-2-methyl-propionic acid

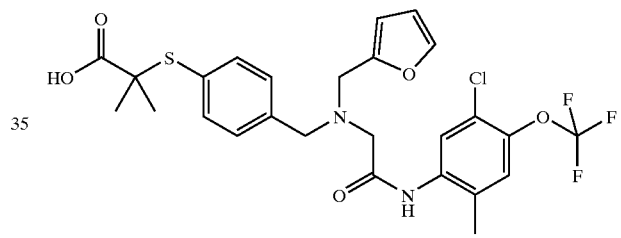

Yield: 90.9% of theory

¹H-NMR (300 MHz, CDCl₃): δ=1.46 (s, 6H); 2.28 (s, 3H); 3.32 (s, 2H); 3.75 (s, 4H); 6.30 (dd, 2H); 7.10 (s, 1H); 7.29 (d, 2H); 7.36 (d, 1H); 7.48 (d, 2H); 8.27 (s, 1H); 9.16 (s, 1H).

Example 3-35

2-[[4-[[[2-[(2,4-Dimethylphenyl)amino]-2-oxoethyl](2-furanylmethyl)amino]-methyl]phenyl]thio]-2-ethyl-butanoic acid

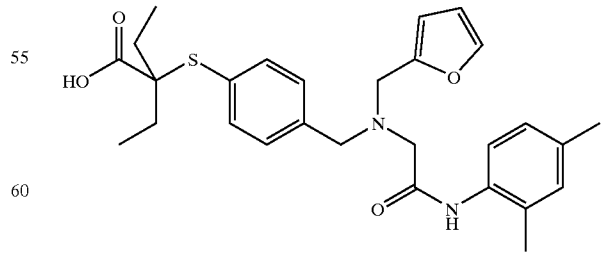

Yield: 96.6% of theory

¹H-NMR (300 MHz, CDCl₃): δ=0.97 (t, 6H); 1.60–1.90 (m, 4H); 2.25 (s, 3H); 2.28 (s, 3H); 3.31 (s, 2H); 3.73 (s,

Example 3-36

2-[[4-[[[2-[[5-Chloro-2-methyl-4-(trifluoromethoxy)phenyl]amino]-2-oxoethyl](2-furanylmethyl)amino]methyl]phenyl]thio]-2-ethyl-butanoic acid

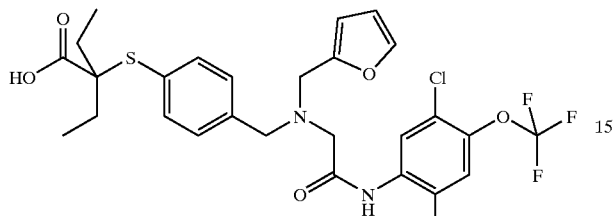

Yield: 90.9% of theory $^1$H-NMR (300 MHz, CDCl$_3$): δ=0.96 (t, 6H); 1.58–1.87 (m, 4H); 2.28 (s, 3H); 3.31 (s, 2H); 3.73 (s, 2H); 3.76 (s, 2H); 6.26 (d, 1H); 6.30–6.36 (m, 1H); 7.10 (s, 1H); 7.27 (d, 2H); 7.34–7.40 (m, 1H); 7.45 (d, 2H); 8.28 (s, 1H); 9.16 (s, 1H).

Example 3-37

2-[[4-[[[2-[[5-Chloro-2-methyl-4-(trifluoromethoxy)phenyl]amino]-2-oxoethyl](2-methoxyethyl)amino]methyl]phenyl]thio]-2-methyl-propionic acid

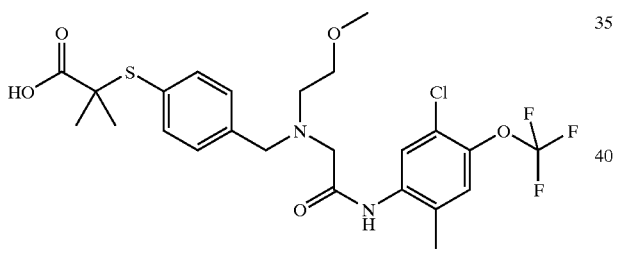

Yield: 83.9% of theory $^1$H-NMR (200 MHz, CDCl$_3$): δ=1.46 (s, 6H); 2.27 (s, 3H); 2.84 (t, 2H); 3.27 (s, 3H); 3.31 (s, 2H); 3.50 (t, 2H); 3.77 (s, 2H); 7.10 (br s, 1H); 7.31 (d, 2H); 7.48 (d, 2H); 8.24 (s, 1H); 9.43 (s, 1H).

Example 3-38

2-Methyl-2-[4-[[[2-[[4-(1-methylethyl)-2-(trifluoromethyl)phenyl]amino]-2-oxoethyl][(5-methyl-2-furanyl)methyl]amino]methyl]phenoxy]-propionic acid

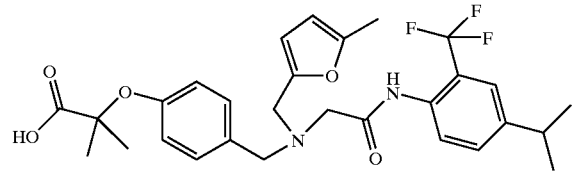

Yield: 91% of theory $^1$H-NMR (200 MHz, CDCl$_3$): δ=1.25 (d, 6H); 1.55 (s, 6H); 2.17 (s, 3H); 2.91 (sept., 1H); 3.28 (s, 2H); 3.7 (s, 4H); 5.80–5.90 (m, 1H); 6.13 (d, 1H); 6.90 (m, 2H); 7.17–7.30 (m, 2H); 7.32–7.47 (m, 2H); 8.12 (d, 1H); 9.55 (br s, 1H).

Example 3-39

2-[4-[[[2-[(2-Ethoxy-1-naphthalenyl)amino]-2-oxoethyl][(5-methyl-2-furanyl)-methyl]amino]methyl]phenoxy]-2-methyl-propionic acid

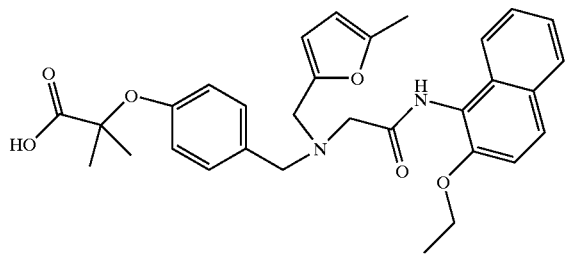

Yield: 64% of theory $^1$H-NMR (300 MHz, CDCl$_3$): δ=1.25–1.32 (t, 3H); 1.60 (s, 3H); 2.25 (s, 3H); 3.45 (s, 2H); 3.82 (s, 4H); 4.15 (quart., 2H); 5.94 (m, 1H); 6.17 (d, 1H); 6.90–7.00 (m, 2H); 7.23–7.46 (m, 5H); 7.60–7.70 (m, 1H); 7.75–7.80 (m, 2H); 9.05 (br s, 1H).

Example 3-40

2-Methyl-2-[4-[[[(5-methyl-2-furanyl)-methyl][2-oxo-2-[(5,6,7,8-tetrahydro-1-naphthalenyl)amino]ethyl]amino]methyl]phenoxy]-propionic acid

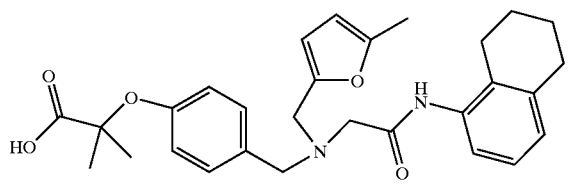

Yield: 76% of theory $^1$H-NMR (300 MHz, CDCl$_3$): δ=1.55 (s, 6H); 1.75–1.95 (m, 4H); 2.20 (s, 3H); 2.36 (t, 2H); 2.78 (t, 2H); 3.30 (s, 2H); 3.69 (s, 4H); 5.89 (m, 1H); 6.12 (d, 1H); 6.83–6.94 (m, 4H); 7.09 (t, 1H); 7.20–7.32 (m, 1H); 7.85 (d, 1H); 9.15 (s, 1H).

Example 3-41

2-[4-[[[2-[(2,4-Dichlorophenyl)amino]-2-oxoethyl](2-methoxyethyl)amino]methyl]-phenoxy]-2-methyl-propionic acid

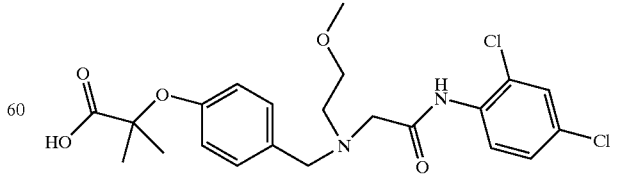

Yield: 69% of theory $^1$H-NMR (300 MHz, CDCl$_3$): δ=1.55 (s, 6H); 2.82 (t, 2H); 3.28 (s, 3H); 3.00 (s, 2H); 3.54 (t, 2H); 3.75 (s, 2H);

6.90 (m, 2H); 7.18–7.36 (m, 3H); 7.39 (d, 1H); 8.40 (d, 1H); 9.90 (br s, 1H).

Example 3-42

2-[4-[[(2-Methoxyethyl)[2-[[4-(1-naphthalenyloxy)-2-(trifluoromethyl)phenyl]-amino]-2-oxoethyl]amino]methyl]phenoxy]-2-methyl-propionic acid

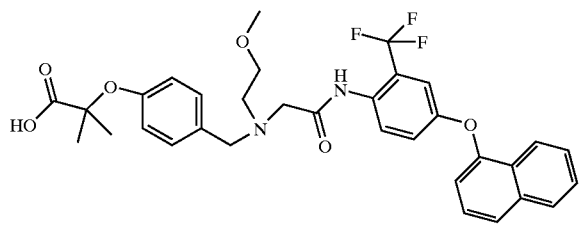

Yield: 74% of theory $^1$H-NMR (300 MHz, DMSO): δ=1.45 (s, 6H); 2.72 (t, 2H); 3.18 (s, 3H); 3.25 (s, 2H); 3.47 (t, 2H); 3.68 (s, 2H); 6.78 (d, 2H); 7.10 (d, 1H); 7.21 (d, 2H); 7.28 (dd, 1H); 7.40 (d, 1H); 7.48–7.66 (m, 3H); 7.80 (d, 1H); 7.90 (d, 1H); 8.05 (t, 2H); 9.60 (br s, 1H).

Example 3-43

2-[4-[[[2-[[5-[(Ethylsulphonyl)methyl]-1-naphthalenyl]amino]-2-oxoethyl](2-methoxyethyl)amino]methyl]phenoxy]-2-methyl-propionic acid

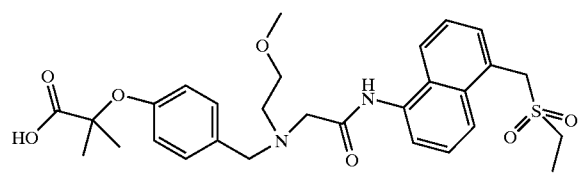

Yield: 40.5% of theory $^1$H-NMR (400 MHz, CD$_2$Cl$_2$): δ=1.34 (t, 3H); 1.46 (s, 6H); 2.83–3.04 (m, 4H); 3.24 (s, 3H); 3.37 (s, 2H); 3.32–3.64 (m, 2H); 3.78 (s, 2H); 4.72 (s, 2H); 6.83 (d, 2H); 7.31 (d, 2H); 7.46–7.65 (m, 3H); 7.90 (d, 1H); 8.04–8.20 (m, 2H); 10.10 (br s, 1H).

Example 3-44

2-Methyl-2-[4-[[[2-[[4-(1-methylethyl)-2-(trifluoromethyl)phenyl]amino]-2-oxoethyl][(4-methyl-5-oxazolyl)methyl]amino]methyl]phenoxy]-propionic acid

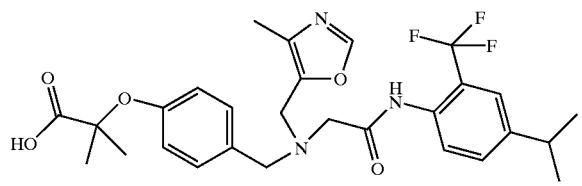

Yield: 69% of theory $^1$H-NMR (200 MHz, CDCl$_3$): δ=1.25 (d, 6H); 1.58 (s, 6H); 2.09 (s, 3H); 2.82–3.04 (sept., 1H); 3.30 (s, 2H); 3.66 (s, 2H); 3.76 (s, 2H); 6.90 (d, 2H); 7.25 (d, 2H); 7.35–7.48 (m, 2H); 7.80 (s, 1H); 8.11 (d, 1H); 9.40 (br s, 1H).

Example 3-45

2-[4-[[[2-[[2,4-Bis(trifluoromethyl)phenyl]amino]-2-oxoethyl][(4-methyl-5-oxazolyl)methyl]amino]methyl]phenoxy]-2-methyl-propionic acid

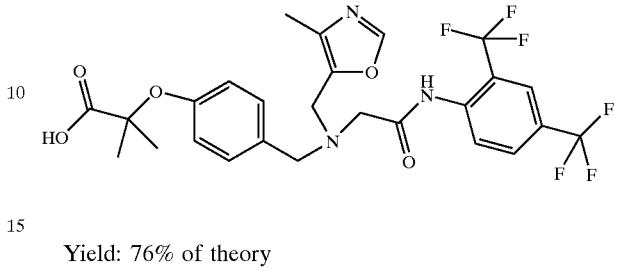

Yield: 76% of theory $^1$H-NMR (200 MHz, CDCl$_3$): δ=1.60 (s, 6H); 2.10 (s, 3H); 3.32 (s, 2H); 3.70 (s, 2H); 3.77 (s, 2H); 6.90 (d, 2H); 7.21 (d, 2H); 7.73–7.90 (m, 3H); 8.55 (d, 1H); 9.68 (br s, 1H).

Example 3-46

2-[4-[[[2-[[2,4-Bis(trifluoromethyl)phenyl]amino]-2-oxoethyl](2-methoxyethyl)-amino]methyl]phenoxy]-2-methyl-propionic acid

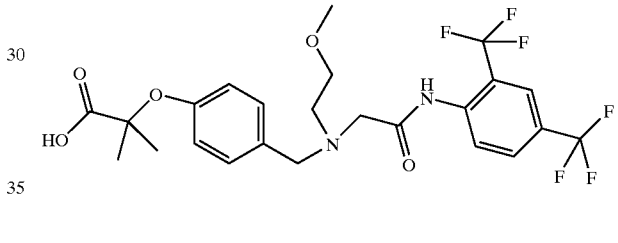

Yield: 77% of theory $^1$H-NMR (300 MHz, CDCl$_3$): δ=1.55 (s, 6H); 2.84 (t, 2H); 3.25 (s, 3H); 3.35 (s, 2H); 3.55 (t, 2H); 3.75 (s, 2H); 6.90 (d, 2H); 7.15–7.30 (m, 2H); 7.75 (d, 1H); 7.88 (s, 1H); 8.59 (d, 1H); 9.91 (br s, 1H).

Example 3-47

2-[4-[[[2-[[2,4-Bis(trifluoromethyl)phenyl]amino]-2-oxoethyl](2-furanylmethyl)]-amino]methyl]phenoxy]-2-methyl-propionic acid

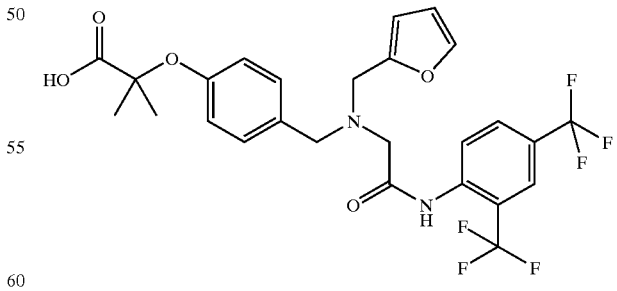

Yield: 91% of theory $^1$H-NMR (300 MHz, CDCl$_3$): δ=1.57 (s, 6H); 3.30 (s, 2H); 3.70 (s, 2H); 3.77 (s, 2H); 3.77 (s, 2H); 6.30 (dd, 2H); 6.88 (d, 2H); 7.20–7.35 (m, 2H); 7.37–7.42 (m, 1H); 7.75 (d, 1H); 7.86 (s, 1H); 8.56 (d, 1H); 9.80 (br s, 1H).

Example 3-48

2-[[4-[[[2-[[2,4-Bis(trifluoromethyl)phenyl]amino]-2-oxoethyl](2-furanylmethyl)-amino]methyl]phenyl]thio]-2-methyl-propionic acid

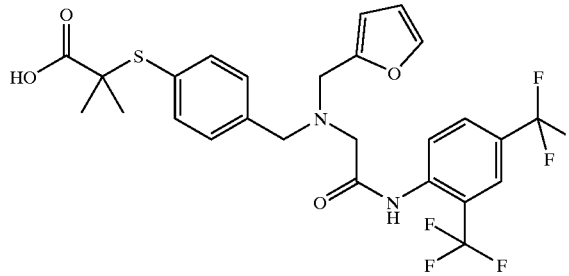

Yield: 91% of theory

¹H-NMR (300 MHz, CDCl₃): δ=1.46 (s, 6H); 3.32 (s, 2H); 3.75 (s, 4H); 6.25 (dd, 2H); 7.20–7.40 (m, 3H); 7.50 (d, 2H); 7.78 (d, 1H); 7.90 (s, 1H); 8.59 (d, 1H); 9.78 (br s, 1H).

The following compounds were obtained similarly to the procedure of Examples 3-9 and 3-11:

Example 3-49

2-[[4-[[[2-[(4-Cyclohexyl-2-methylphenyl)amino]-2-oxoethyl](2-methoxyethyl)-amino]methyl]phenyl]thio]-2-methyl-propionic acid hydrochloride

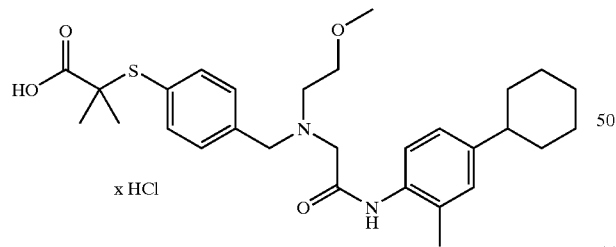

Yield: 53.3% of theory

¹H-NMR (300 MHz, DMSO): δ=1.20–1.48 (m, 12H); 1.62–1.87 (m, 5H); 2.14 (s, 3H); 3.27 (s, 3H); 3.51 (br s, 2H); 3.74 (br s, 2H); 4.12 (br s, 2H); 4.51 (br s, 2H); 7.02 (d, 2H); 7.16–7.30 (br s, 1H); 7.46–7.68 (m, 4H); 9.93 (br s, 1H); 10.36 (br s, 1H); 12.74 (br s, 1H).

Example 3-50

2-[[4-[[[2-[[4-(1,1-Dimethylethyl)-2-methylphenyl]amino]-2-oxoethyl](2-methoxyethyl)amino]methyl]phenyl]thio]-2-methyl-propionic acid hydrochloride

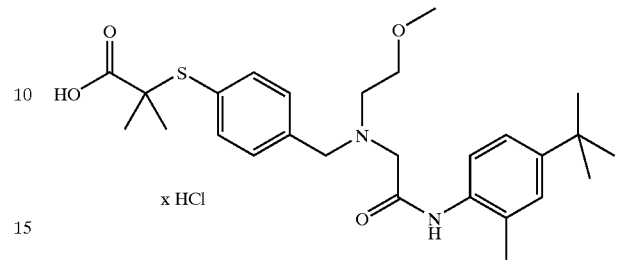

Yield: 85.3% of theory

¹H-NMR (300 MHz, CDCl₃): δ=1.29 (s, 9H); 1.56 (s, 6H); 2.26 (s, 3H); 2.86 (t, 2H); 3.29 (s, 3H); 3.35 (s, 2H); 3.53 (t, 2H); 3.74 (s, 2H); 6.88 (d, 2H); 7.15–7.26 (m, 4H); 7.79 (d, 1H); 9.26 (s, 1H).

Example 3-51

2-Methyl-2-[4-[[[2-[[4-(1-methylethyl)-2-(trifluoromethyl)phenyl]amino]-2-oxo-ethyl][(5-methyl-2-furanyl)methyl]amino]methyl]phenoxy]-propionic acid hydrochloride

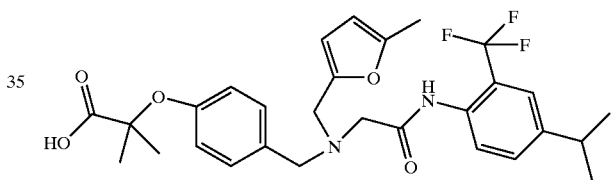

Yield: 99% of theory

¹H-NMR (300 MHz, DMSO): δ=1.20 (d, 6H); 1.50 (s, 6H); 2.27 (br s, 3H); 2.96–3.05 (sept., 1H); 3.95 (br s, 2H); 4.31 (br s, 4H); 6.17 (br s, 1H); 6.63 (br s, 1H); 6.85 (d, 2H); 7.46–7.57 (m, 5H); 10.23 (br s, 1H); 10.55 (br s, 1H); 13.15 (br s, 1H).

Example 3-52

2-[4-[[[2-[[4-(1,1-Dimethylethyl)-2-methylphenyl]amino]-2-oxoethyl](2-ethyl)amino]methyl]phenoxy]-2-methyl-propionic acid hydrochloride

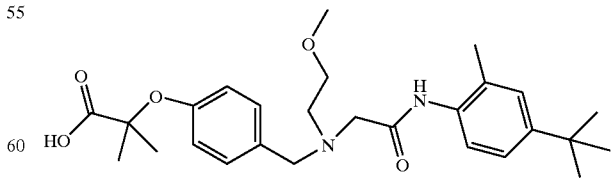

Yield: 54% of theory

LC-MS: 470 [M⁺]

Example 3-53

2-[4-[[[2-[(2,4-Dimethylphenyl)amino]-2-oxoethyl](2-furanylmethyl)amino]-methyl]phenoxy]-2-methyl-propionic acid sodium salt

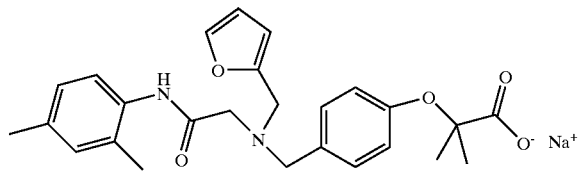

0.015 g (0.03 mmol) of the compound from Example 3-4 is dissolved in 0.5 ml of ethanol and treated with 0.3 ml of 1N aqueous sodium hydroxide solution. The reaction mixture is stirred for another 5 min and then concentrated using a rotary evaporator. The residue is taken up in a little toluene and the solvent is removed under reduced pressure. The product is then dried under reduced pressure for 20 hours. This gives 0.015 g (95.5% of theory) of the title compound.

1H-NMR (200 MHz, CDCl$_3$): δ=1.21 (s, 6H); 2.10–2.20 (m, 6H); 3.16 (s, 2H); 3.58–3.64 (m, 4H); 6.18–6.25 (m, 2H); 6.73–6.82 (m, 2H); 7.09–7.35 (m, 3H); 7.71 (d, 1H); 9.00 (br s, 1H).

The following compounds were obtained similarly to the procedure of Examples 3-7 and 3-10:

Example 3-54

1,1-Dimethylethyl 2-[[4-[[[2-[[4-(1-methylethyl)-2-(trifluoromethyl)phenyl]amino]-2-oxoethyl](2-methoxyethyl)amino]methyl]phenyl]thio]-2-methyl-propionate

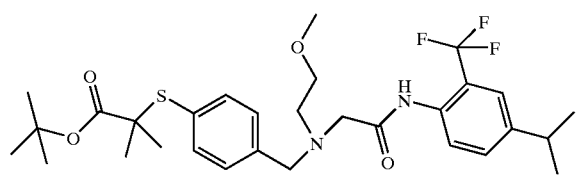

Yield: 61% of theory $^1$H-NMR (200 MHz, CDCl$_3$): δ=1.24 (d, 6H); 1.39 (s, 9H); 1.42 (s, 6H); 2.80 (t, 2H); 2.90–3.1 (m, 1H); 3.28 (s, 3H); 3.32 (s, 2H); 3.53 (t, 2H); 3.78 (s, 2H); 7.25–7.50 (m, 6H); 8.14 (d, 1H); 9.62 (br s, 1H).

Example 3-55

1,1-Dimethylethyl 2-methyl-2-[[4-[[[2-[[4-(1-methylethyl)-2-(trifluoromethyl)-phenyl]amino]-2-oxo-ethyl][(4-methyl-5-oxazolyl)methyl]amino]methyl]phenyl]-thio]propionate

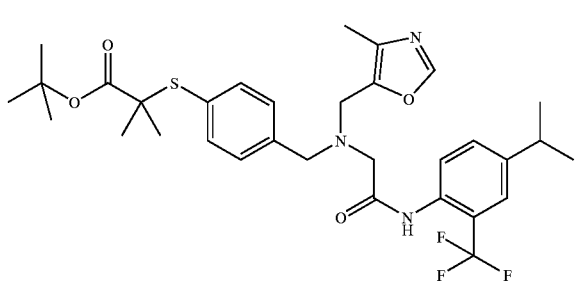

Yield: 66% of theory $^1$H-NMR (300 MHz, CDCl$_3$): δ=1.25 (d, 6H); 1.40 (s, 9H); 1.43 (s, 6H); 2.10 (s, 3H); 2.90–3.10 (m, 1H); 3.29 (s, 2H); 3.70–3.80 (m, 4H); 7.30–7.55 (m, 6H); 7.77 (s, 1H); 8.13 (d, 1H); 9.40 (br s, 1H).

Example 3-56

1,1-Dimethylethyl 2-[[4-[[[2-[(2-methyl-4-methoxyphenyl)amino]-2-oxoethyl][(4-methyl-5-oxazolyl)-methyl]amino]methyl]phenyl]thio]-2-methyl-propionate

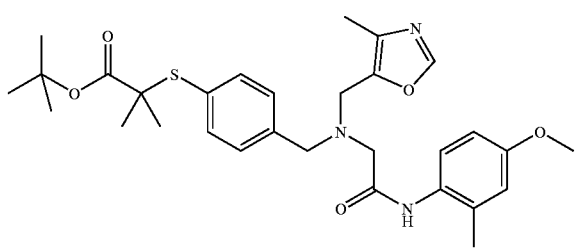

Yield: 86% of theory $^1$H-NMR (200 MHz, CDCl$_3$): δ=1.41 (s, 9H); 1.43 (s, 9H); 2.13 (s, 3H); 2.24 (s, 3H); 3.31 (s, 2H); 3.70–3.81 (m, 7H); 6.68–6.80 (m, 2H); 7.30 (d, 2H); 7.5 (d, 2H); 7.67–7.75 (m, 1H); 7.78 (s, 1H); 8.80 (br s, 1H).

Example 3-57

1,1-Dimethyl-ethyl 2-[[4-[[[2-[[2,4-bis(trifluoromethyl)phenyl]amino]-2-oxoethyl]-[(4-methyl-5-oxazolyl)methyl]amino]methyl]phenyl]thio]-2-methyl-propionate

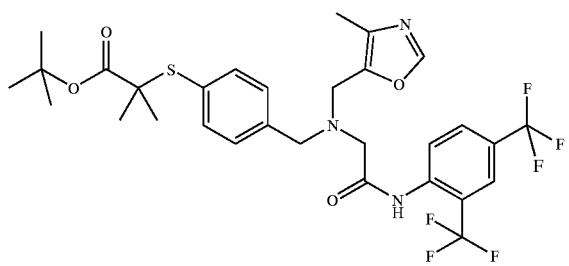

Yield: 84% of theory

¹H-NMR (200 MHz, CDCl₃): δ=1.40 (s, 9H); 1.42 (s, 6H); 2.11 (s, 3H); 3.32 (s, 2H); 3.74–3.82 (m, 4H); 7.29 (d, 2H); 7.49 (d, 2H); 7.70–7.85 (m, 2H); 7.87 (s, 1H); 8.57 (d, 1H); 9.67 (br s, 1H).

Example 3-58

1,1-Dimethylethyl 2-[4-[[[2-[(4-cyclohexyl-2-methylphenyl)amino]-2-oxoethyl][(4-methyl-5-oxazolyl)-methyl]amino]methyl]phenoxy]-2-methyl-propionate

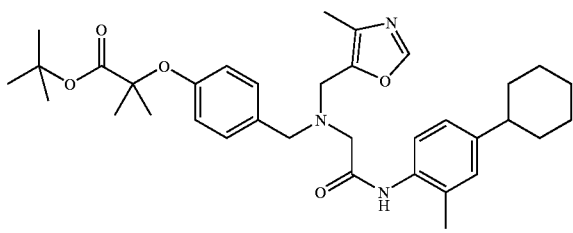

Yield: 54.8% of theory

¹H-NMR (200 MHz, CDCl₃): δ=1.30–1.46 (m, 14H); 1.55 (s, 6H); 1.62–1.94 (m, 6H); 2.12 (s, 3H); 2.26 (s, 3H); 3.29 (s, 2H); 3.65 (s, 2H); 3.74 (s, 2H); 6.82 (d, 2H); 6.98–7.08 (m, 2H); 7.18 (d, 2H); 7.77 (s, 1H); 7.83 (d, 1H); 8.96 (br s, 1H).

Example 3-59

1,1-Dimethyl-ethyl 2-[4-[[[2-[[4-(1,1-dimethylethyl)-2-methylphenyl]amino]-2-oxo-ethyl][(4-methyl-5-oxazolyl)methyl]amino]methyl]phenoxy]-2-methyl-propionate

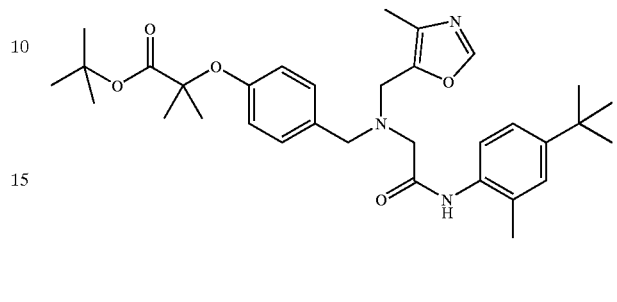

Yield: 64.7% of theory

¹H-NMR (200 MHz, CDCl₃): δ=1.29 (s, 9H); 1.41 (s, 9H); 1.55 (s, 6H); 2.12 (s, 3H); 2.28 (s, 3H); 3.29 (s, 2H); 3.65 (s, 2H); 3.75 (s, 2H); 6.82 (d, 2H); 7.10–7.30 (m, 4H); 7.77 (s, 1H); 7.85 (d, 1H); 8.98 (br s, 1H).

Example 3-60

2-[[4-[[[2-[[4-(1-Methylethyl)-2-(trifluoromethyl)phenyl]amino]-2-oxoethyl](2-methoxyethyl)amino]methyl]phenyl]thio]-2-methyl-propionic acid

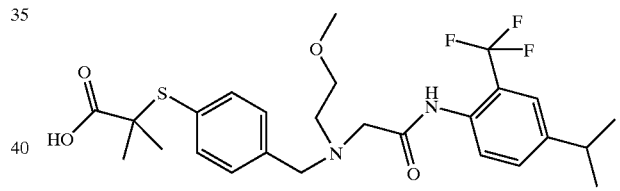

0.248 g (0.43 mmol) of the compound from Example 3-54 is initially charged in 5 ml of dichloromethane. At room temperature, 5 ml of trifluoroacetic acid are added. The reaction mixture is stirred at room temperature for 2 hours and then concentrated under reduced pressure using a rotary evaporator. The residue is taken up in ethyl acetate and extracted with water, 20% strength sodium acetate solution, water and saturated sodium chloride solution. The organic phase is dried over magnesium sulphate and freed from the solvent under reduced pressure. The product is purified chromatographically on silica gel (dichloromethane, dichloromethane/methanol 30:1) and then dried under reduced pressure. This gives 197 mg (88% of theory) of the title compound.

¹H-NMR (200 MHz, CDCl₃): δ=1.25 (d, 6H); 1.49 (s, 6H); 2.80 (t, 2H); 2.85–3.00 (m, 1H); 3.30 (s, 3H); 3.32 (s, 2H); 3.49–3.59 (m, 2H); 3.80 (s, 2H); 7.24–7.53 (m, 6H); 8.12 (d, 1H); 9.58 (br s, 1H).

The following compounds were obtained similarly to the procedure of Example 3-60:

Example 3-61

2-Methyl-2-[[4-[[[2-[[4(1-methylethyl)-2-(trifluoromethyl)phenyl]amino]-2-oxo-ethyl][(4-methyl-5-oxazolyl)methyl]amino]methyl]phenyl]thio]-propionic acid

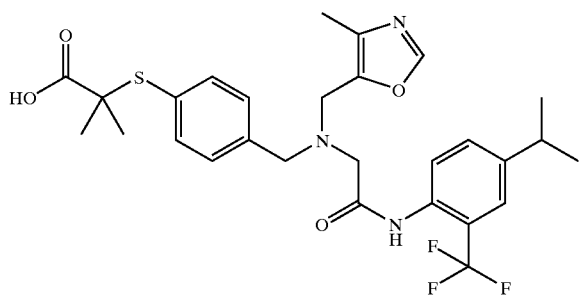

Yield: 81% of theory

¹H-NMR (300 MHz, CDCl₃): δ=1.25 (d, 6H); 1.50 (s, 6H); 2.07 (s, 3H); 2.85–3.00 (m, 1H); 3.39 (s, 2H); 3.74–3.78 (m, 4H); 7.30 (d, 2H); 7.36–7.53 (m, 4H); 7.79 (s, 1H); 8.11 (d, 1H); 9.39 (br s, 1H).

Example 3-62

2-[[4-[[[2-[(2-Methyl-4-methoxyphenyl)amino]-2-oxoethyl][(4-methyl-5-oxazolyl)-methyl]amino]methyl]phenyl]thio]-2-methyl-propionic acid

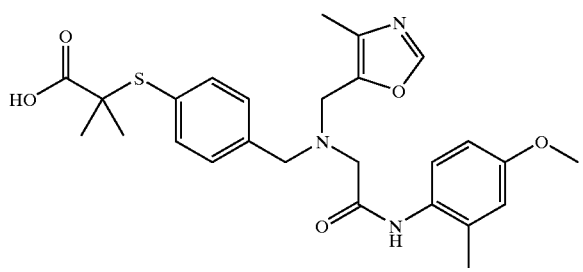

Yield: 84% of theory

¹H-NMR (200 MHz, CDCl₃): δ=1.51 (s, 6H); 2.08 (s, 3H); 2.23 (s, 3H); 3.35 (s, 2H); 3.70–3.82 (m, 7H); 6.70–6.80 (m, 2H); 7.28 (d, 2H); 7.48 (d, 2H); 7.63–7.73 (m, 1H); 7.80 (s, 1H); 8.81 (br s, 1H).

Example 3-63

2-[[4-[[[2-[[2,4-Bis(trifluoromethyl)phenyl]amino]-2-oxoethyl][(4-methyl-5-oxazolyl)methyl]amino]methyl]phenyl]thio]-2-methyl-propionic acid

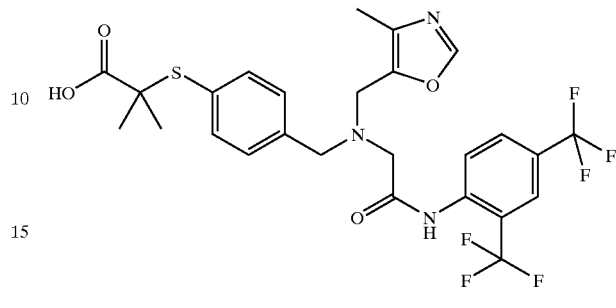

Yield: 76% of theory

¹H-NMR (300 MHz, CDCl₃): δ=1.49 (s, 6H); 2.09 (s, 3H); 3.35 (s, 2H); 3.74–3.80 (m, 4H); 7.29 (d, 2H); 7.49 (d, 2H); 7.75–7.82 (m, 2H); 7.87 (s, 1H); 8.56 (d, 1H); 9.66 (br s, 1H).

Example 3-64

2-[4-[[[2-[(4-Cyclohexyl-2-methylphenyl)amino]-2-oxoethyl][(4-methyl-5-oxazolyl)-methyl]amino]methyl]phenoxy]-2-methyl-propionic acid

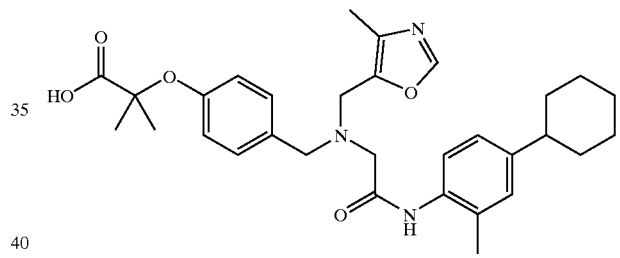

Yield: 80% of theory

LC-MS: Acetonitrile/30% aqueous HCl/water (gradient): R$_t$=2.64 min ([M+H]⁺=534).

Example 3-65

2-[4-[[[2-[[4-(1,1-Dimethylethyl)-2-methylphenyl]amino]-2-oxoethyl][(4-methyl-5-oxazolyl)methyl]amino]methyl]phenoxy]-2-methyl-propionic acid

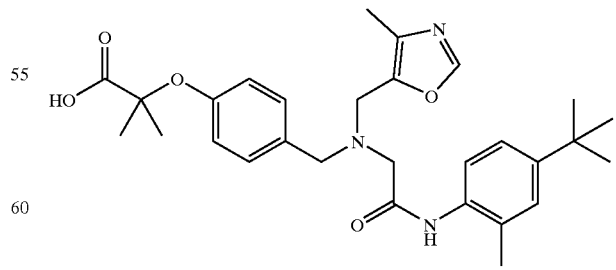

Yield: 80% of theory

LC-MS: Acetonitrile/30% aqueous HCl/water (gradient): R$_t$=2.43 min ([M+H]⁺=508).

WORKING EXAMPLES 4

Example 4-1

2-[4-[[[2-[(2,5-Dimethylphenyl)amino]-2-oxoethyl](2-furanylmethyl)amino]methyl]-phenoxy]-2-methyl-propanoic acid

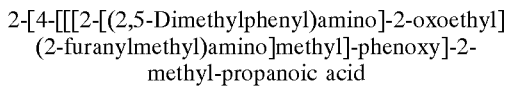
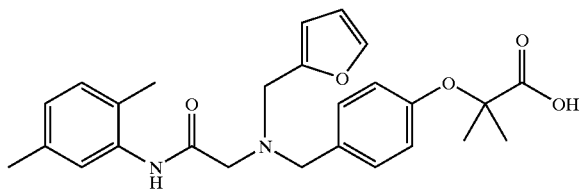

Step a)

Wang resin (from Rapp Polymere, Order No. H 1011) (48.0 g, 14.06 mmol of reactive groups) is suspended in dichloromethane. 2-(4-Formylphenoxy)-2-methyl-propionic acid [G. J. Ellymes, C. Glynis, *J. Chem. Soc. Perkin Trans.* 2, 1993, 43–48] (8.78 g, 42.18 mmol), diisopropylcarbodiimide (10.65 g, 84.35 mmol) and DMAP (3.44 g, 28.12 mmol) are added, and the mixture is then shaken at room temperature for 18 h. The mixture is then filtered and the resin is washed with dichloromethane, DMF and methanol, giving resin A.

Step b)

Resin A (2.50 g, 0.72 mmol of reactive groups) and 2-furfurylamine (352 mg, 3.62 mmol) are suspended in 20 ml of trimethyl orthoformate. The mixture is shaken at room temperature for 20 h and then filtered, and the resin is washed with DMF. The resin is then suspended in 20 ml of DMF, tetrabutylammonium borohydride (559 mg, 2.17 mmol) and acetic acid (0.42 ml, 7.25 mmol) are added and the mixture is shaken at room temperature for 7 h. The mixture is then filtered and the resin is washed with dichloromethane, DMF and methanol, giving resin B1.

Step c)

Resin B1 (2.5 g, 0.72 mmol of reactive groups) is suspended in 40 ml of dioxane and treated with triethylamine (3.03 ml, 21.75 mmol) and trimethylsilyl bromoacetate (2.38 ml, 14.5 mmol). The mixture is shaken at 60° C. overnight. The mixture is then filtered and the resin is washed with dichloromethane, DMF and methanol. The protective silyl group is removed by suspending the resin in 25 ml of dioxane and treating it with tetrabutylammonium fluoride solution (1 M in THF, 1 ml). The mixture is shaken at room temperature for 1 h and then filtered. The resin is then washed with dichloromethane, DMF and methanol, giving resin C1.

Step d)

Resin C1 (2.5 g, 0.72 mmol of reactive groups) is suspended in 20 ml of DMF and treated with diisopropylethylamine (656 mg, 5.08 mmol), HATU (1.38 g, 3.63 mmol) and 2,5-dimethylaniline (615 mg, 5.08 mmol). The mixture is shaken at room temperature for 18 h and then filtered, and the resin is washed with dichloromethane, DMF and methanol. The resin is then suspended in a mixture of dichloromethane and trifluoroacetic acid. The mixture is shaken at room temperature for 30 min and then filtered and evaporated. The target compound is obtained as a colourless film.

LC-MS: $R_t$=3.68 min; $[M+H]^+$=451.3 (100%), $[M-H]^+$=449.3 (100%) [Method: Symmetry C18 column (Waters), flow rate: 0.5 ml/min, oven temp 40° C., pressure 400 bar, gradient: t=0 min: 10% A, 90% B; t=4.0 min: 90% A, 10% B; t=6.0 min: 90% A, 10% B; t=6.1 min 10% A, 90% B; t=7.5 min 10% A, 90% B. A: $CH_3CN$+0.1% HCOOH; B: $H_2O$+0.1% HCOOH].

$^1$H-NMR ($d_6$-DMSO): δ=1.4 (s, 6H), 2.3 (s, 3H), 2.4 (s, 3H), 3.3 (s, 2H), 3.7 (s, 2H), 3.8 (s, 2H), 6.3 (d, 1H), 6.4 (d, 1H), 6.8 (d, 1H), 6.9 (d, 2H), 7.05 (d, 1H), 7.2 (m, 2H), 7.4 (s, 1H), 7.8 (s, 1H).

Example 4-2

2-[4-[[[2-[(4-Methoxy-2,5-dimethylphenyl)amino]-2-oxoethyl](2-furanylmethyl)-amino]-methyl]phenoxy]-2-methyl-propanoic acid

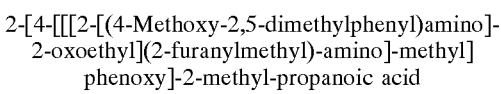
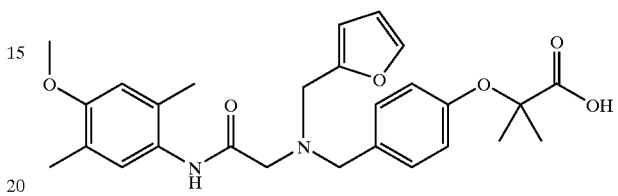

Resin C1 from Example 4-1 step c) (2.5 g, 0.72 mmol of reactive groups) is suspended in 20 ml of DMF and treated with diisopropylethylamine (656 mg, 5.08 mmol), HATU (1.38 g, 3.63 mmol) and 2,5-dimethyl-4-methoxyaniline (756 mg, 5.08 mmol). The mixture is shaken at room temperature for 18 h and then filtered, and the resin is washed with dichloromethane, DMF and methanol. The resin is then suspended in a mixture of dichloromethane and trifluoroacetic acid. The mixture is shaken at room temperature for 30 min and then filtered and evaporated. The target compound is obtained as a colourless film.

LC-MS: $R_t$=3.48 min; $[M+H]^+$=481.226 (100%), $[M-H]^+$=479.226 (100%) [Method: Symmetry C18 column (Waters), flow rate: 0.5 ml/min, oven temp. 40° C., pressure 400 bar, gradient: t=0 min: 10% A, 90% B; t=4.0 min: 90% A, 10% B; t=6.0 min: 90% A, 10% B; t=6.1 min 10% A, 90% B; t=7.5 min 10% A, 90% B. A: $CH_3CN$+0.1% HCOOH; B: $H_2O$+0.1% HCOOH].

Example 4-3

2-[4-[[[2-[(4-Methoxy-2,5-dimethylphenyl)amino]-2-oxoethyl](2-thienylmethyl)-amino]-methyl]phenoxy]-2-methyl-propanoic acid

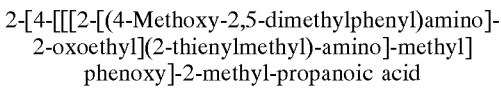
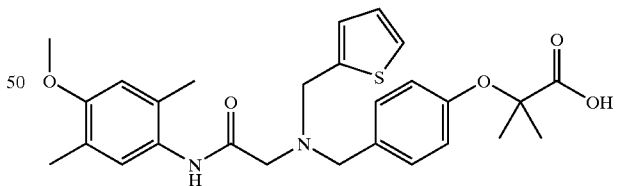

Step a)

Resin A from Example 4-1 step a) (2.50 g, 0.72 mmol of reactive groups) and 2-aminomethylthiophene (409 mg, 3.62 mmol) are suspended in 20 ml of trimethyl orthoformate. The mixture is shaken at room temperature overnight and then filtered, and the resin is washed with DMF. The resin is then suspended in 20 ml of DMF, treated with tetrabutylammonium borohydride (559 mg, 2.17 mmol) and acetic acid (0.42 ml, 7.25 mmol) and shaken at room temperature for 7 h. The mixture is then filtered and the resin is washed with dichloromethane, DMF and methanol, giving resin B2.

Step b)

Resin B2 (2.5 g, 0.72 mmol of reactive groups) is suspended in 40 ml of dioxane and treated with triethylamine (3.03 ml, 21.75 mmol) and trimethylsilyl bromoacetate (2.38 ml, 14.5 mmol). The mixture is shaken at 60° C. overnight. The mixture is then filtered and the resin is washed with dichloromethane, DMF and methanol. The protective silyl group is removed by suspending the resin in 25 ml of dioxane and treating it with tetrabutylammonium fluoride solution (1 M in THF, 1 ml). The mixture is shaken at room temperature for 1 h and then filtered. The resin is then washed with dichloromethane, DMF and methanol, giving resin C2.

Step c)

Resin C2 (2.5 g, 0.72 mmol of reactive groups) is suspended in 20 ml of DMF and treated with diisopropylethylamine (656 mg, 5.08 mmol), HATU (1.38 g, 3.63 mmol) and 2,5-dimethyl-4-methoxyaniline (657 mg, 5.08 mmol). The mixture is shaken at room temperature for 18 h and then filtered, and the resin is washed with dichloromethane, DMF and methanol. The resin is then suspended in a mixture of dichloromethane and trifluoroacetic acid. The mixture is shaken at room temperature for 30 min and then filtered and evaporated. The target compound is obtained as a colourless film.

LC-MS: $R_f$=3.90 min; $[M+H]^+$=497.4 (100%), $[M-H]^+$=495.4 (100%) [Method: Symmetry C18 column (Waters), flow rate: 0.5 ml/min, oven temp. 40° C., pressure 400 bar, gradient: t=0 min: 10% A, 90% B; t=4.0 min: 90% A, 10% B; t=6.0 min: 90% A, 10% B; t=6.1 min 10% A, 90% B; t=7.5 min 10% A, 90% B. A: $CH_3CN$+0.1% HCOOH; B: $H_2O$+0.1% HCOOH].

$^1$H-NMR ($d_6$-DMSO): δ=1.5 (s, 6H), 2.1 (s, 3H), 2.2 (s, 3H), 3.3 (s, 2H), 3.7 (s, 2H), 3.8 (s, 3H), 4.0 (s, 2H), 6.8–7.5 (m, 9H).

The following compound is obtained in a similar manner:

Example 4-4

2-[4-[[[2-[(4-Methoxy-2,5-dimethylphenyl)amino]-2-oxoethyl][(5-methyl-2-furanyl)-methyl]-amino]methyl]phenoxy]-2-methyl-propanoic acid

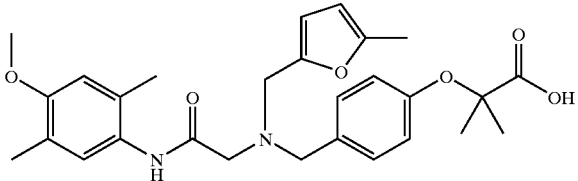

LC-MS: $R_f$=2.76 min; $[M+H]^+$=495 (100%), $[M-H]^+$=493 (100%) [Method: Symmetry C18 column (Waters), flow rate: 0.5 ml/min, oven temp. 40° C., pressure 400 bar, gradient: t=0 min: 10% A, 90% B; t=4.0 min: 90% A, 10% B; t=6.0 min: 90% A, 10% B; t=6.1 min 10% A, 90% B; t=7.5 min 10% A, 90% B. A: $CH_3CN$+0.1% HCOOH; B: $H_2O$+0.1% HCOOH].

EXAMPLE A

Cellular Transactivation Assay

Test Principle

A cellular assay is used to identify activators of the peroxisome proliferator-activated receptor alpha (PPAR-alpha).

Since mammalian cells contain different endogenous nuclear receptors which may complicate an unambiguous interpretation of the results, an established chimera system is used in which the ligand binding domain of the human PPARα receptor is fused to the DNA binding domain of the yeast transcription factor GAL4. The resulting GAL4-PPARα chimera is co-transfected and stably expressed in CHO cells having a reporter construct.

Cloning

The GAL4-PPARα expression construct contains the ligand binding domain of PPARα (amino acids 167–468), which is PCR-amplified and cloned into the vector pcDNA3.1. This vector already contains the GAL4 DNA binding domain (amino acids 1–147) of the vector pFC2-dbd (Stratagene). The reporter construct, which contains five copies of the GAL4 binding site upstream of a thymidine kinase promoter, expresses firefly luciferase (Photinus pyralis) following activation and binding of GAL4-PPARα.

Transactivation Assay (Luciferase Reporter)

CHO (chinese hamster ovary) cells are sown in DMEM/F12 medium (BioWhittaker), supplemented by 10% foetal calf serum, 1% penicillin/streptomycin (GIBCO), at a cell density of $2 \times 10^3$ cells per well in a 384 well plate (Greiner). The cells are cultivated at 37° C. for 48 h and then stimulated. To this end, the substances to be tested are taken up in CHO-A-SFM medium (GIBCO), supplemented by 10% foetal calf serum, 1% penicillin/streptomycin (GIBCO) and added to the cells. After a stimulation period of 24 hours, the luciferase activity is measured using a video camera. The relative light units measured give, as a function of the substrate concentration, a sigmoidal stimulation curve. The $EC_{50}$ values are calculated using the computer programme GraphPad PRISM (Version 3.02).

In this test, the compounds according to the invention of Examples 3-4, 3-6, 3-60, 1-9, 2-7 and 2-12 show $EC_{50}$ values of from 0.04 to 200 nM.

EXAMPLE B

Determination of Fibrinogen

To determine the effect on the plasma fibrinogen concentration, male Wistar rats are treated with the substance to be examined for a period of 4–9 days, by administration via a stomach tube or by mixing the substance with the feed. In terminal anaesthesia, citrated blood is then obtained by heart puncture. The plasma fibrinogen levels are determined using the Clauss method [Clauss A., *Acta Haematol.* 17, 237–46 (1957)] by measuring the thrombin time using human fibrinogen as standard. In some cases, parallel determinations are carried out using a turbidometric method [Becker U., Bartl K., Wahlefeld A. W., *Thrombosis Res.* 35, 475–84 (1984)] where batroxobin is used instead of thrombin.

EXAMPLE C

Description of the test for finding pharmacologically active substances which increase apoprotein A1 (ApoA1) and HDL cholesterol (HDL-C) concentrations in the serum of transgenic mice transfected with the human ApoA1 gene (hApoA1)

The substances to be examined in vivo for their HDL-C-increasing activity are administered orally to male transgenic hApoA1 mice. One day prior to the start of the experiment, the animals are randomized into groups with the same number of animals, generally n=7–10. During the entire experiment, the animals have drinking water and feed ad libitum. The substances are administered orally once a day for 7 days. To this end, the test substances are dissolved in a solution of Solutol HS 15+ethanol+saline (0.9%) in a ratio of 1+1+8 or in a solution of Solutol HS 15+saline (0.9%) in a ratio of 2+8. The dissolved substances are administered in a volume of 10 ml/kg of body weight using a stomach tube. Animals which have been treated in exactly the same manner but have only been given the solvent (10 ml/kg of body weight), without test substance, serve as control group.

Prior to the first administration of substance, a blood sample from each of the mice is taken by puncture of the retroorbital venous plexus, to determine ApoA1, serum cholesterol, HDL-C and serum triglycerides (TG) (zero value). Subsequently, using a stomach tube, the test substance is administered for the first time to the animals. 24 hours after the last administration of substance (on day 8 after the start of the treatment), another blood sample is taken from each animal by puncture of the retroorbital venous plexus, to determine the same parameters. The blood samples are centrifuged and, after the serum has been obtained, cholesterol and TG are determined photometrically using an EPOS Analyzer 5060 (Eppendorf-Gerätebau, Netheler & Hinz GmbH, Hamburg). The said determinations are carried out using commercial enzyme tests (Boehringer Mannheim, Mannheim).

To determine the HDL-C, the non-HDL-C fraction is precipitated using 20% PEG 8000 in 0.2 M glycine buffer pH 10. From the supernatant, the cholesterol is determined UV-photometrically (BIO-TEK Instruments Inc. USA) in a 96-well plate using a commercial reagent (Ecoline 25, Merck, Darmstadt).

Human mouse ApoA1 is determined with a Sandwich ELISA method using a polyclonal antihuman ApoA1 and a monoclonal antihuman ApoA1 antibody (Biodesign International, USA). Quantification is carried out UV-photometrically (BIO-TEK Instruments, USA) using peroxidase-coupled anti-mouse-IGG antibodies (KPL, USA) and peroxidase substrate (KPL, USA).

The effect of the test substances on the HDL-C concentration is determined by subtracting the value measured for the $1^{st}$ blood sample (zero value) from the value measured for the $2^{nd}$ blood sample (after the treatment). The mean of the differences of all HDL-C values of one group is determined and compared to the mean of the differences of the control group.

Statistical evaluation is carried out using student's t-test, after the variances have been checked for homogeneity.

Substances which increase the HDL-C of the treated animals in a statistically significant (p<0.05) manner by at least 20%, compared to the control group, are considered to be pharmacologically effective.

What is claimed is:

1. Compounds of the general formula (I)

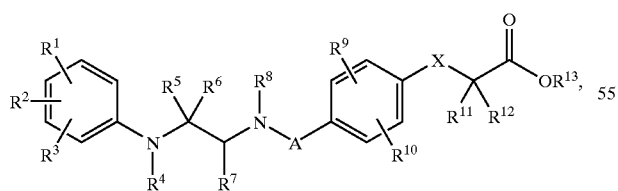

(I)

in which

A represents a bond or represents a —CH$_2$— or —CH$_2$CH$_2$— group,

X represents O, S or CH$_2$, $R^1$, $R^2$ and $R^3$ are identical or different and independently of one another each represents hydrogen, (C$_1$–C$_6$)-alkyl, (C$_3$–C$_7$)-cycloalkyl, hydroxyl, (C$_1$–C$_6$)-alkoxy, (C$_6$–C$_{10}$)-aryloxy, halogen, trifluoromethyl, trifluoromethoxy, (C$_1$–C$_6$)-alkylaminosulphonyl, nitro or cyano, or $R^1$ and $R^2$ are attached to two adjacent carbon atoms and together with these form a fused cyclohexane or benzene ring, the latter optionally being substituted by a (C$_1$–C$_4$)-alkylsulphonylmethyl group, and $R^3$ is as defined above, $R^4$ represents hydrogen or (C$_1$–C$_4$)-alkyl, $R^5$ and $R^6$ together with the carbon atom to which they are attached form a carbonyl group, $R^7$ represents hydrogen, (C$_1$–C$_6$)-alkyl, phenyl or benzyl, where the aromatic radicals mentioned for their part may in each case be mono- to trisubstituted by identical or different substituents from the group consisting of (C$_1$–C$_6$)-alkyl, (C$_1$–C$_6$)-alkoxy, hydroxyl and halogen, $R^8$ represents furanylmethyl which optionally may be mono- to trisubstituted by identical or different substituents from the group consisting of halogen, hydroxyl, (C$_1$–C$_6$)-alkyl, (C$_1$–C$_6$)-alkoxy, trifluoromethyl, trifluoromethoxy, cyano, nitro and amino, $R^9$ and $R^{10}$ are identical or different and independently of one another each represents hydrogen, (C$_1$–C$_6$)-alkyl, (C$_1$–C$_6$)-alkoxy, trifluoromethyl, trifluoromethoxy or halogen, $R^{11}$ and $R^{12}$ are identical or different and independently of one another each represents hydrogen or (C$_1$–C$_6$)-alkyl or together with the carbon atom to which they are attached form a (C$_4$–C$_7$)-cycloalkyl ring, and $R^{13}$ represents hydrogen, and their pharmaceutically acceptable salts, hydrates and solvates.

2. Compounds of the general formula (I) according to claim 1, in which

A represents a bond or represents a —CH$_2$— or —CH$_2$CH$_2$— group,

X represents O, S or CH$_2$, $R^1$, $R^2$ and $R^3$ are identical or different and independently of one another each represents hydrogen, (C$_1$–C$_6$)-alkyl, (C$_1$–C$_6$)-alkoxy, hydroxyl, halogen, trifluoromethyl, trifluoromethoxy, nitro or cyano, $R^4$ represents hydrogen or (C$_1$–C$_4$)-alkyl, $R^5$ and $R^6$ together with the carbon atom to which they are attached form a carbonyl group, $R^7$ represents hydrogen, (C$_1$–C$_6$)-alkyl, phenyl or benzyl, in which the aromatic radicals mentioned for their part may in each case be mono- to trisubstituted by identical or different substituents from the group consisting of (C$_1$–C$_6$)-alkyl, (C$_1$–C$_6$)-alkoxy, hydroxyl and halogen, $R^8$ represents furanylmethyl which optionally may be mono- to trisubstituted by identical or different substituents from the group consisting of halogen, hydroxyl, (C$_1$–C$_6$)-alkyl, (C$_1$–C$_6$)-alkoxy, trifluoromethyl, trifluoromethoxy, cyano, nitro and amino, $R^9$ and $R^{10}$ are identical or different and independently of one another each represents hydrogen, (C$_1$–C$_6$)-alkyl, (C$_1$–C$_6$)-alkoxy, trifluoromethyl, trifluoromethoxy or halogen, $R^{11}$ and $R^{12}$ are identical or different and independently of one another each represents hydrogen or $(C_1-C_6)$-alkyl, or together with the carbon atom to which they are attached form a $(C_4-C_7)$-cycloalkyl ring, and $R^{13}$ represents hydrogen, and their pharmaceutically acceptable salts, hydrates and solvates.

3. Compounds of the general formula (I) according to claim 1 or 2, in which

A represents a —$CH_2$— or —$CH_2CH_2$— group,

X represents O, S or $CH_2$, $R^1$, $R^2$ and $R^3$ are identical or different and independently of one another each represents hydrogen, $(C_1-C_4)$-alkyl, $(C_1-C_4)$-alkoxy, chlorine, fluorine, trifluoromethyl, trifluoromethoxy, nitro or cyano, $R^4$ represents hydrogen or methyl, $R^5$ and $R^6$ together with the carbon atom to which they are attached form a carbonyl group, $R^7$ represents hydrogen, $(C_1-C_4)$-alkyl or benzyl, $R^8$ represents furanylmethyl which optionally may be mono- to trisubstituted by identical or different substituents from the group consisting of chlorine, fluorine, bromine, hydroxyl, $(C_1-C_4)$-alkyl, $(C_1-C_4)$-alkoxy, trifluoromethyl and amino, $R^9$ and $R^{10}$ are identical or different and independently of one another each represents hydrogen, $(C_1-C_3)$-alkyl, $(C_1-C_3)$-alkoxy, trifluoromethyl, fluorine or chlorine, $R^{11}$ and $R^{12}$ are identical or different and independently of one another each represents hydrogen methyl or ethyl, or together with the carbon atom to which they are attached form a cyclopentyl or cyclohexyl ring, and $R^{13}$ represents hydrogen, and their pharmaceutically acceptable salts, hydrates and solvates.

4. Compounds of the general formula (I), according to claim 1 in which

A represents a —$CH_2$— or —$CH_2CH_2$— group,

X represents O, S or $CH_2$, $R^1$ represents hydrogen, methyl or methoxy, $R^2$ and $R^3$ are identical or different and independently of one another each represents methyl, trifluoromethyl, methoxy, trifluoromethoxy, chlorine or fluorine, $R^4$ represents hydrogen, $R^5$ and $R^6$ together with the carbon atom to which they are attached form a carbonyl group, $R^7$ represents methyl, ethyl, n-propyl or hydrogen, $R^8$ represents furanylmethyl which optionally may be mono- or disubstituted by identical or different substituents from the group consisting of methyl and ethyl, $R^9$ and $R^{10}$ are identical or different and each represents hydrogen or methyl, $R^{11}$ and $R^{12}$ are identical or different and each represents hydrogen or methyl, and $R^{13}$ represents hydrogen, and their pharmaceutically acceptable salts, hydrates and solvates.

5. Compounds of formula (IA)

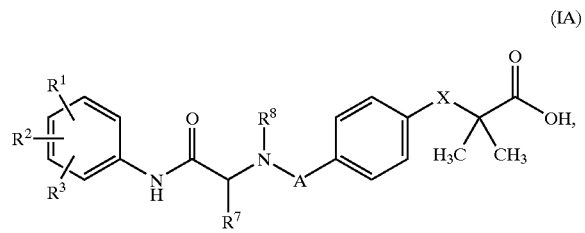

(IA)

in which

A represents a —$CH_2$— or —$CH_2CH_2$— group,

X represents O or S, $R^1$ represents hydrogen, methyl or methoxy, $R^2$ and $R^3$ are identical or different and independently of one another each represents methyl, isopropyl, tert-butyl, cyclohexyl, trifluoromethyl, methoxy, trifluoromethoxy, chlorine or fluorine, and $R^8$ represents furanylmethyl which optionally may be mono- or disubstituted by methyl.

6. Medicaments, comprising at least one compound of the formula (I) as defined in claim 1 and inert nontoxic, pharmaceutically suitable carriers, auxiliaries, solvents, vehicles, emulsifiers and/or dispersants.

7. A method of treating arteriosclerosis, comprising administering to a mammal an effective amount of a compound of the formula (I) as defined in claim 1.

8. Process for preparing medicaments, characterized in that at least one compound of the formula (I) as defined in claim 1 is converted into an administration form using auxiliaries and/or carriers.

9. Process for preparing compounds of the formula (I) as defined in claim 1, characterized in that

[A] compounds of the general formula (II)

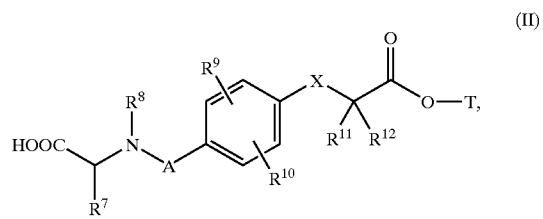

(II)

in which

A, X, $R^7$, $R^8$, $R^9$, $R^{10}$, $R^{11}$ and $R^{12}$ are as defined in claim 1 and T represents benzyl, $(C_1-C_6)$-alkyl or a polymeric support suitable for solid-phase synthesis, are initially, with activation of the carboxylic acid group in (II), reacted with compounds of the general formula (III)

(III)

in which
R¹, R² and R³ are each as defined in claim 1,
to give compounds of the general formula (Ia)

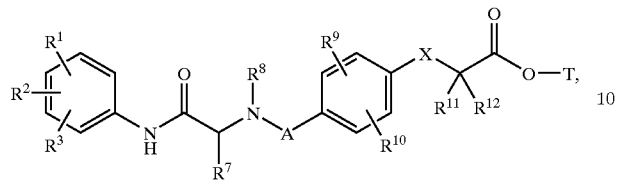
(Ia)

in which
A, X, T, R¹, R², R³, R⁷, R⁸, R⁹, R¹⁰, R¹¹ and R¹² are each as defined above, or

[B] compounds of the general formula (IV)

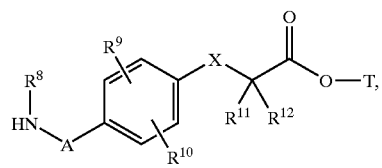
(IV)

in which
A, X, T, R⁸, R⁹, R¹⁰, R¹¹ and R¹² are each as defined above are, in the presence of a base, reacted with compounds of the general formula (V)

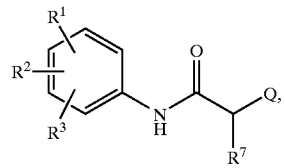
(V)

in which
R¹, R², R³ and R⁷ are each as defined above and
Q is a suitable leaving group, likewise to compounds of the general formula (Ia)
the compounds of the general formula (Ia) are, if appropriate according to known methods for amide alkylation or amide reduction, converted into compounds of the general formula (Ib)

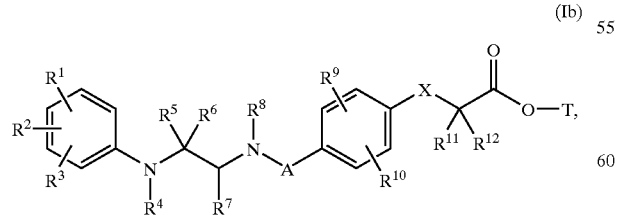
(Ib)

in which
A, X, T, R¹, R², R³, R⁴, R⁵, R⁶, R⁷, R⁸, R⁹, R¹⁰, R¹¹ and R¹² are each as defined above, then converted with acids or bases into the corresponding carboxylic acids of the general formula (Ic)

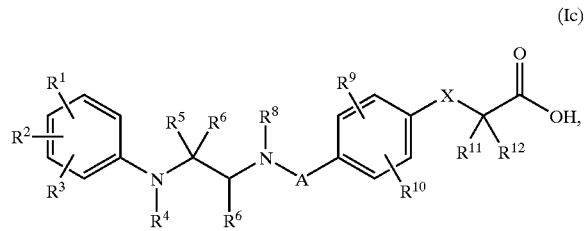
(Ic)

in which
A, X, R¹, R², R³, R⁴, R⁵, R⁶, R⁷, R⁸, R⁹, R¹⁰, R¹¹ and R¹² are each as defined above, and these are, if appropriate according to known methods for esterification, modified further by reaction with compounds of the general formula (VI)

R¹³—Z     (VI), in which
R¹³ is as defined above and
Z represents a suitable leaving group or represents a hydroxyl group.

10. A method of increasing pathologically low HDL levels and for reducing elevated triglyceride and LDL levels, comprising administering to a mammal an effective amount of a compound according to claim 1.

11. A method of treating or preventing a peroxisome-proliferator-activated receptor modulated disease or condition, comprising administering to a mammal an effective amount of a compound according to claim 1.

12. The compound of claim 1,

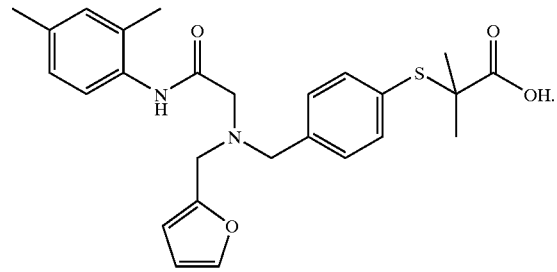

2-[[4-[[[2-[(2,4-dimethylphenyl)amino]-2-oxoethyl](2-furanylmethyl)amino]-methyl]phenyl]thio]-2-methyl-propanoic acid.

* * * * *